United States Patent
Chaudhari et al.

(10) Patent No.: US 8,623,880 B2
(45) Date of Patent: Jan. 7, 2014

(54) FUSED PYRIMIDINE-DIONE DERIVATIVES AS TRPA1 MODULATORS

(75) Inventors: Sachin Sundarlal Chaudhari, Navi Mumbai (IN); Sukeerthi Kumar, Navi Mumbai (IN); Abraham Thomas, Navi Mumbai (IN); Nisha Parag Patil, Mumbai (IN); Ashok Bhausaheb Kadam, Navi Mumbai (IN); Vishal Govindrao Deshmukh, Shrirampur (IN); Sachin Vasantrao Dhone, Usmanabad (IN); Rajendra Prakash Chikhale, Ahmednagar (IN); Neelima Khairatkar-Joshi, Thane (IN); Indranil Mukhopadhyay, Navi Mumbai (IN)

(73) Assignee: Glenmark Pharmaceuticals S.A., La Chaux-de-Fonds (CH)

( * ) Notice: Subject to any disclaimer, the term of this patent is extended or adjusted under 35 U.S.C. 154(b) by 51 days.

(21) Appl. No.: 13/258,115

(22) PCT Filed: Mar. 17, 2010

(86) PCT No.: PCT/IB2010/000553
§ 371 (c)(1),
(2), (4) Date: Sep. 21, 2011

(87) PCT Pub. No.: WO2010/109287
PCT Pub. Date: Sep. 30, 2010

(65) Prior Publication Data
US 2012/0041004 A1     Feb. 16, 2012

Related U.S. Application Data

(60) Provisional application No. 61/171,355, filed on Apr. 21, 2009, provisional application No. 61/251,944, filed on Oct. 15, 2009, provisional application No. 61/253,263, filed on Oct. 20, 2009, provisional application No. 61/294,463, filed on Jan. 12, 2010, provisional application No. 61/300,241, filed on Feb. 1, 2010.

(30) Foreign Application Priority Data

Mar. 23, 2009 (IN) .......................... 665/MUM/2009
Sep. 23, 2009 (IN) ........................ 2211/MUM/2009
Sep. 23, 2009 (IN) ........................ 2212/MUM/2009
Dec. 15, 2009 (IN) ........................ 2891/MUM/2009
Dec. 15, 2009 (IN) ........................ 2892/MUM/2009

(51) Int. Cl.
*A01N 43/90* (2006.01)
*A61K 31/519* (2006.01)
*C07D 487/00* (2006.01)

(52) U.S. Cl.
USPC .................................... 514/262.1; 544/262

(58) Field of Classification Search
None
See application file for complete search history.

(56) References Cited

FOREIGN PATENT DOCUMENTS

| | | |
|---|---|---|
| EP | 1847541 A1 | 10/2007 |
| GB | 1445697 | 8/1976 |
| WO | 98/46606 A1 | 10/1998 |
| WO | 03000694 A1 | 1/2003 |
| WO | 2004/014916 A1 | 2/2004 |
| WO | 2004055054 A1 | 7/2004 |
| WO | 2005077959 A1 | 8/2005 |
| WO | 2005089206 A2 | 9/2005 |
| WO | 2007073505 A2 | 6/2007 |
| WO | 2007108750 A1 | 9/2007 |
| WO | 2008094909 A2 | 8/2008 |
| WO | 2009002933 A1 | 12/2008 |
| WO | 2009158719 A2 | 12/2009 |

OTHER PUBLICATIONS

Pfleiderer, Wolfgang, et al.: Abstract, "About the New Synthesis of Pyrazolo [3,4-d]- and 1,2,4-Triazino [6,5-d]-Pyrimidines", Institute for Organic Chemistry and Organic Chemical Technology and the Technical University Stuttgart, Tests in the Pyrimidine series VIII 1), 1958.

Edstrom, E. D. et al.: "A New Synthetic Route to B-2'-Deoxyribosyl-5-substituted Pyrrolo[2,3-d]pyrimidines. Synthesis of 2'-Deoxycadeguomycin", J. Org. Chem., vol. 60, 1995, pp. 5069-5076.

Egg, H. et al.: "A Convenient Synthesis of 1,3-Dialky-6-methyluracils and 1,3-Dialky-6-ethylthymines", Synthesis, Dec. 1982, pp. 1071-1073.

(Continued)

*Primary Examiner* — Jeffrey Murray
(74) *Attorney, Agent, or Firm* — Pergament Gilman & Cepeda LLP; Milagros A. Cepeda; Edward D. Pergament

(57) ABSTRACT

The invention described herein relates to novel fused pyrimidinediones derivatives of formula (I) which are TRPA (Transient Receptor Potential subfamily A) modulators. In particular, compounds described herein are useful for treating or preventing diseases, conditions and/or disorders modulated by TRPA1 (Transient Receptor Potential subfamily A, member 1). This invention also provides processes for preparing compounds described herein, intermediates used in their synthesis, pharmaceutical compositions thereof, and methods for treating or preventing diseases, conditions and/or disorders modulated by TRPA1.

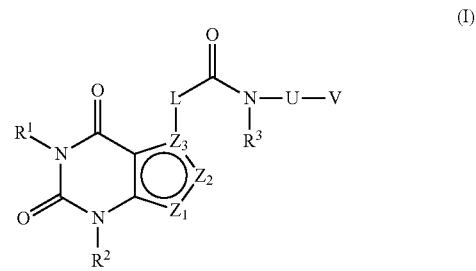

23 Claims, No Drawings

(56) References Cited

OTHER PUBLICATIONS

Foley, K. M. et al.: "Problems of Overarching Importance Which Transcend Organ Systems", Cecil Textbook of Medicine, vol. 1, No. 20, 1996, pp. 100-107.

Han, Q. et al.: "Design, Synthesis, and Biological Evaluation of Potent and Selective Amidino Bicyclic Factor Xa Inhibitors", J. Med. Chem., vol. 43, 2000, pp. 4398-4415.

Kawahara, N. et al.: "Simple Syntheses of 1,3-Dialkylpyrrolo- and Furopyrimidines1)", Chem. Pharm. Bull., vol. 33, No. 11, 1985, pp. 4740-4748.

King, Carroll L. et al.: "The Reaction of Ketones with Iodine and Thiourea", J. Am. Chem. Soc., vol. 72, Aug. 1950, pp. 3722-3725.

Kotha, S. et al.: "A Simple Synthetic Approach to Allylated Aromatics via the Suzuki-Miyaura Cross-Coupling Reaction", Synlett, No. 12, Jul. 7, 2005, pp. 1877-1880.

Little, T. L. et al.: "A Simple and Practical Synthesis of 2-Aminoimidazoles", J. Org. Chem., 1994, vol. 59, pp. 7299-7305.

Toth, A. et al.: "Arachidonyl dopamine as a ligand for the vanilloid receptor VR1 of the rat", Life Sciences, vol. 73, Feb. 12, 2003, pp. 487-498.

Voorhoeve, P. M. et al.: "A Genetic Screen Implicates miRNA-372 and miRNA-373 As Oncogenes in Testicular Germ Cell Tumors", Cell, vol. 124, Mar. 24, 2006, pp. 1169-1181.

Macpherson, L. J. et al.: "Noxious compounds activate TRPA1 ion channels through covalent modification of cysteins", Nature Publishing Group, vol. 445, Feb. 1, 2007, pp. 541-545.

Mcmahon, S. B. et al.: "Increasingly Irritable and Close to Tears: TRPA1 in Inflammatory Pain", Cell, vol. 124, Mar. 24, 2006, pp. 1123-1125.

Mcnamara, C. R. et al.: "TRPA1 mediates formalin-induced pain", Proc. Natl. Acad. Sci. U.S.A., vol. 104, No. 33, Aug. 14, 2007, pp. 13525-13530.

Naik, S. J. et al.: "Synthesis and application of novel 4,5,6,7-tetrahydrobenzothiazole based azo disperse dyes", ARKIVOC USA, Inc., vol. xiii, Apr. 21, 2005, pp. 141-149.

Noell, C. W. et al.: "Aromaticity in Heterocyclic Systems. II. The Application of N.M.R. in a Study of the Synthesis and Structure of Certain Imidazo [1,2-c] Pyrimidines and Related Pyrrolo [2,3-d] Pyrimidines", J. Het. Chem., vol. 1, 1964, pp. 34-41.

Ogura, H. et al.: "Synthesis of Pyrrolopyrimidines and Thienopyrimidines1)", Chem Pharm. Bull., vol. 20, No. 2, 1972, pp. 404-408.

Ohkubo, M. et al.: "Studies on Cerebral Protective Agents. VIII.1a) Synthesis of 2-Aminothiazoles and 2-Thiazolecarboxamides with Anti-anoxic Activity", Chem. Pharm. Bull., vol. 43, No. 9, Sep. 1995, pp. 1497-1504.

Okuhara, Dayne Y. et al.: "Transient receptor potential channels as drug targets", Expert Opinion on Therapeutic Targets, vol. 11, No. 3, 2007, pp. 391-401.

Wissenbach U. et al.: "TRP channels as potential drug targets", Biology of the Cell, vol. 96, 2004, pp. 47-54.

Thurber, T. C. et al.: "The Synthesis and Properties of Certain N-Methylated 5-Diazouracils (1)", J. Heterocyclic Chem., vol. 12, Aug. 1975, pp. 711-716.

Papesch, V. et al.: "Isomeric Pyrazolo[4,3-d]pyrimidinediones", J. Org. Chem., vol. 30, 1965, pp. 199-203.

Pfleiderer W. et al.: "Uber Neue Synthesen Von Pryazolo[3-4-d]-Und 1.2.4- Triazino[6.5-d]-Pyrimidinen", Justus Liebigs Ann Chem. vol. 615, 1958, pp. 42-47.

Postema, M.H.D. et al., "Synthesis and Partial Biological Evaluation of a Small Library of Differentially-Linked β-C-Disaccharides1", J. Org. Chem., vol. 68, 2003, pp. 4748-4754.

Prajapati, D. et al.: "Studies on Pyrimidine-Annelated Heterocycles; 8.1 Intramolecular Cycloaddition of Thiophene and Nitrile Oxide or Nitrone Groups Bonded to 1,3-Dimethyluracils", Synthesis, 1998, pp. 342-344.

Senda, S. et al.: "A Facile Synthesis of Pyrrolo[3,4-d]pyrimidines and Pyrimidol[4-5-d]pyridazines", Synthesis, Jun. 1978, pp. 463-465.

Senda, S. et al.: "Pyrimidine Derivatives and Related Compounds. XII.1) The Vilsmeier Reaction of Barbituric Acid Derivatives and Uracil Derivatives", Yakagaku Zasshi, vol. 91, No. 12, 1971, pp. 1372-1376.

Story, G. et al.: "ANKTM1, a TRP-like Channel Expressed in Nociceptive Neurons, Is Activated by Cold Temperatures", Cell, vol. 112, Mar. 21, 2003, pp. 819-829.

Press, J. B. et al.: "Furo[3,4-d]pyrimidine-2,4-dione derivatives with antihypertensive activity. Analogues of thienopyrimidine-2,4-diones", Eur. J. Med. Chem., vol. 24, 1989, pp. 627-630.

Supplemental European Search Report dated Jun. 25, 2012.

International Search Report dated Aug. 26, 2010 from corresponding International Patent Application No. PCT/IB2010/000553.

International Search Report dated Oct. 6, 2010 from corresponding International Patent Application No. PCT/IB2010/000930.

International Search Report dated Jun. 28, 2010 from corresponding International Patent Application No. PCT/IB2010/000834.

International Search Report dated Jun. 28, 2010 from corresponding International Patent Application No. PCT/IB2010/000840.

FUSED PYRIMIDINE-DIONE DERIVATIVES AS TRPA1 MODULATORS

RELATED APPLICATIONS

This application is a National Stage Application under 35 U.S.C. 371 of PCT International Application No. PCT/IB2010/000553, filed Mar. 17, 2010, which claims priority to Indian Patent Application Nos. 665/MUM/2009 filed on Mar. 23, 2009; 2211/MUM/2009 filed on Sep. 23, 2009; 2212/MUM/2009 filed on Sep. 23, 2009; 2891/MUM/2009 filed on Dec. 15, 2009; 2892/MUM/2009 filed on Dec. 15, 2009 and U.S. Provisional Application Nos. 61/171,355 filed on Apr. 21, 2009; 61/251,944 filed on Oct. 15, 2009; 61/253,263 filed on Oct. 20, 2009; 61/294,463 filed on Jan. 12, 2010 and 61/300,241 filed on Feb. 1, 2010 all of which are hereby incorporated by reference.

TECHNICAL FIELD

The present patent application relates to fused pyrimidinedinedione derivatives with transient receptor potential ankyrin1 (TRPA1) activity.

BACKGROUND OF THE INVENTION

The transient receptor potential (TRP) channels or receptors are pain receptors. They have been classified into seven subfamilies: TRPC (canonical), TRPV (vanilloid), TRPM (melastatin), TRPP (polycystin), TRPML (mucolipin), TRPA (ankyrin, ANKTM1) and TRPN (NOMPC) families. The TRPC family can be divided into 4 subfamilies (i) TRPC1 (ii) TRPC2 (iii) TRPC3, TRPC6, TRPC7 and (iv) TRPC4, TRPC5 based on sequence functional similarities. Currently the TRPV family has 6 members. TRPV5 and TRPV6 are more closely related to each other than to TRPV1, TRPV2, TRPV3 or TRPV4. TRPA1 is most closely related to TRPV3 and is more closely related to TRPV1 and TRPV2 than to TRPV5 and TRPV6. The TRPM family has 8 members. Constituents include the following: the founding member TRPM1 (melastatin or LTRPC1), TRPM3 (KIAA1616 or LTRPC3), TRPM7 (TRP-PLIK, ChaK(1), LTRPC7), TRPM6 (ChaK2), TRPM2 (TRPC7 or LTRPC2), TRPM8 (TRP-p8 or CMR1), TRPM5 (MTR1 or LTRPC5) and TRPM4 (FLJ20041 or LTRPC4). The TRPML family consists of the mucolipins, which include TRPML1 (mucolipin 1), TRPML2 (mucolipin 2) and TRPML3 (mucolipin 3). The TRPP family consists of two groups of channels: those predicted to have six transmembrane domains and those that have eleven. TRPP2 (PKD2), TRPP3 (PKD2L1), TRPP5 (PKD2L2) are all predicted to have six transmembrane domains. TRPP1 (PKD1, PC1), PKD-REJ and PKD-1L1 are all thought to have eleven transmembrane domains. The sole mammalian member of the TRPA family is ANKTM1.

It is believed TRPA1 is expressed in nociceptive neurons. Nociceptive neurons of the nervous system sense the peripheral damage and transmit pain signals. TRPA1 is membrane bound and most likely acts as a heterodimeric voltage gated channel. It is believed to have a particular secondary structure, its N-terminus is lined with a large number of ankyrin repeats which are believed to form a spring-like edifice. TRPA1 is activated by a variety of noxious stimuli, including cold temperatures (activated at 17° C.), pungent natural compounds (e.g., mustard, cinnamon and garlic) and environmental irritants (MacPherson L J et al, Nature, 2007, 445; 541-545). Noxious compounds activate TRPA1 ion channels through covalent modification of cysteines to form covalently linked adducts. Variety of endogenous molecules produced during tissue inflammation/injury have been identified as pathological activators of TRPA1 receptor. These include hydrogen peroxide which is produced due to oxidative stress generated during inflammation, alkenyl aldehyde 4-HNE— an intracellular lipid peroxidation product and cyclopentenone prostaglandin 15dPGJ2 which is produced from PGD2 during inflammation/allergic response. TRPA1 is also activated in receptor dependant fashion by Bradykinin (BK) which is released during tissue injury at peripheral terminals The difference between TRPA1 and other TRP receptors is that TRPA1 ligand binding persists for hours due to which the physiological response (e.g., pain) is greatly prolonged. Hence to dissociate the electrophile, an effective antagonist is required.

WO 2009/158719, WO 2009/002933, WO 2008/0949099, WO 2007/073505, WO 2004/055054 and WO 2005/089206 describe the TRP channels as the targets for the treatment of pain and related conditions.

In efforts to discover better analgesics for the treatment of both acute and chronic pain and to develop treatments for various neuropathic and nociceptive pain states, there exists a need for a more effective and safe therapeutic treatment of diseases, conditions and/or disorders modulated by TRPA1.

SUMMARY OF THE INVENTION

Definitions

The present invention relates to compounds of the formula (I):

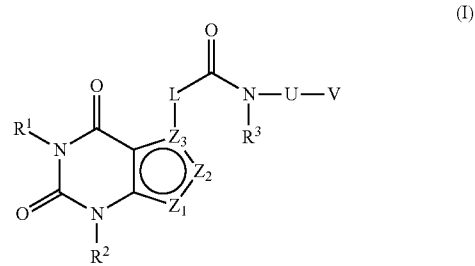

or a pharmaceutically acceptable salt thereof,
wherein,
$Z_1$ is $NR^a$ or $CR^a$;
$Z_2$ is $NR^b$ or $CR^b$;
$Z_3$ is N or C;
with the proviso that when $Z_2$ is $CR^b$ then both $Z_1$ and $Z_3$ are not nitrogen at the same time;
at each occurrence, $R^a$ and $R^b$ which may be same or different, are independently selected from hydrogen, hydroxyl, cyano, halogen, substituted or unsubstituted alkyl, haloalkyl, alkenyl, alkynyl, cycloalkyl, cycloalkylalkyl, —$(CR^xR^y)_nOR^x$, —$COR^x$, —$COOR^x$, —$CONR^xR^y$, —$S(O)_m NR^xR^y$, —$NR^xR^y$, —$NR^x(CR^xR^y)_nOR^x$, —$(CH_2)_n NR^xR^y$, —$(CH_2)_nCHR^xR^y$, —$(CH_2)NR^xR^y$, —$NR^x(CR^xR^y)_n CONR^xR^y$, —$(CH_2)_nNHCOR^x$, —$(CH_2)_nNH(CH_2)_nSO_2R^x$ and $(CH_2)_nNHSO_2R^x$;
alternatively either of $R^a$ or $R^b$ is absent;
$R^1$ and $R^2$, which may be same or different, are independently selected from hydrogen, hydroxyl, substituted or unsubstituted alkyl, haloalkyl, alkenyl, alkynyl, cycloalkyl, cycloalkylalkyl, arylalkyl, $(CR^xR^y)_nOR^x$, $COR^x$, $COOR^x$, $CONR^xR^y$, $(CH_2)_nNR^xR^y$, $(CH_2)_nCHR^xR^y$, $(CH_2)NR^xR^y$ and $(CH_2)_nNHCOR^x$;
$R^3$ is selected from hydrogen, substituted or unsubstituted alkyl, alkenyl, haloalkyl, alkynyl, cycloalkyl, cycloalkylalkyl, cycloalkenyl;

L is a linker selected from —(CR$^x$R$^y$)$_n$—, —O—(CR$^x$R$^y$)$_n$—, —C(O)—, —NR$^x$—, —S(O)$_n$NR$^x$—, —NR$^x$(CR$^x$R$^y$)$_n$— and —S(O)$_m$NR$^x$(CR$^x$R$^y$)$_n$;

U is selected from substituted or unsubstituted aryl, substituted or unsubstituted five membered heterocycles selected from the group consisting of thiazole, isothiazole, oxazole, isoxazole, thiadiazole, oxadiazole, pyrazole, imidazole, furan, thiophene, pyrroles, 1,2,3-triazoles and 1,2,4-triazole; and substituted or unsubstituted six membered heterocycles selected from the group consisting of pyrimidine, pyridine and pyridazine;

V is selected from hydrogen, cyano, nitro, —NR$^x$R$^y$, halogen, hydroxyl, substituted or unsubstituted alkyl, alkenyl, alkynyl, cycloalkyl, cycloalkylalkyl, cycloalkenyl, haloalkyl, haloalkoxy, cycloalkylalkoxy, aryl, arylalkyl, biaryl, heteroaryl, heteroarylalkyl, heterocyclic ring and heterocyclylalkyl, —C(O)OR$^x$, —OR$^x$, —C(O)NR$^x$R$^y$, —C(O)R$^x$ and —SO$_2$NR$^x$R$^y$; or U and V together may form an optionally substituted 3 to 7 membered saturated or unsaturated cyclic ring, that may optionally include one or more heteroatoms selected from O, S and N;

at each occurrence, R$^x$ and R$^y$ are independently selected from the group consisting of hydrogen, hydroxyl, halogen, substituted or unsubstituted alkyl, alkenyl, alkynyl, cycloalkyl, cycloalkylalkyl, cycloalkenyl, aryl, arylalkyl, heteroaryl, heteroarylalkyl, heterocyclic ring and heterocyclylalkyl; and at each occurrence 'm' and 'n' are independently selected from 0 to 2, both inclusive.

According to one embodiment, there is provided a compound of the formula (Ia):

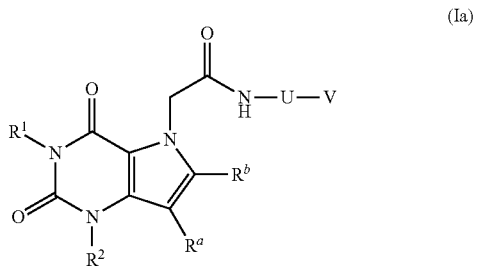

(Ia)

or a pharmaceutically acceptable salt thereof,
wherein,

R$^1$ and R$^2$ which may be same or different, are independently selected from hydrogen, hydroxyl, substituted or unsubstituted alkyl, haloalkyl, alkenyl, alkynyl, cycloalkyl, cycloalkylalkyl, arylalkyl, (CR$^x$R$^y$)$_n$OR$^x$, COR$^x$, COOR$^x$, CONR$^x$R$^y$, (CH$_2$)$_n$NR$^x$R$^y$, (CH$_2$)$_n$CHR$^x$R$^y$, (CH$_2$)NR$^x$R$^y$ and (CH$_2$)$_n$NHCOR$^x$;

U is selected from substituted or unsubstituted aryl, substituted or unsubstituted five membered heterocycles selected from the group consisting of thiazole, isothiazole, oxazole, isoxazole, thiadiazole, oxadiazole, pyrazole, imidazole, furan, thiophene, pyrroles, 1,2,3-triazoles and 1,2,4-triazole; and substituted or unsubstituted six membered heterocycles selected from the group consisting of pyrimidine, pyridine and pyridazine;

V is selected from hydrogen, cyano, nitro, —NR$^x$R$^y$, halogen, hydroxyl, substituted or unsubstituted alkyl, alkenyl, alkynyl, cycloalkyl, cycloalkylalkyl, cycloalkenyl, haloalkyl, haloalkoxy, cycloalkylalkoxy, aryl, arylalkyl, biaryl, heteroaryl, heteroarylalkyl, heterocyclic ring and heterocyclylalkyl, —C(O)OR$^x$, —OR$^x$, —C(O)NR$^x$R$^y$, —C(O)R$^x$ and —SO$_2$NR$^x$R$^y$; or U and V together may form an optionally substituted 3 to 7 membered saturated or unsaturated cyclic ring, which may optionally include one or more heteroatoms selected from O, S and N;

at each occurrence, R$^a$ and R$^b$ which may be same or different, are independently selected from hydrogen, hydroxyl, cyano, halogen, substituted or unsubstituted alkyl, haloalkyl, alkenyl, alkynyl, cycloalkyl, cycloalkylalkyl, —(CR$^x$R$^y$)$_n$OR$^x$, —COR$^x$, —COOR$^x$, —CONR$^x$R$^y$, —S(O)$_m$ NR$^x$R$^y$, —NR$^x$R$^y$, —NR$^x$(CR$^x$R$^y$)$_n$OR$^x$, —(CH$_2$)$_n$NR$^x$R$^y$, —(CH$_2$)$_n$CHR$^x$R$^y$, —(CH$_2$)NR$^x$R$^y$, —NR$^x$(CR$^x$R$^y$)$_n$CONR$^x$R$^y$, —(CH$_2$)$_n$NHCOR$^x$, —(CH$_2$)$_n$NH(CH$_2$)$_n$SO$_2$R$^x$ and (CH$_2$)$_n$NHSO$_2$R$^x$;

at each occurrence, R$^x$ and R$^y$ are independently selected from hydrogen, hydroxyl, halogen, substituted or unsubstituted alkyl, alkenyl, alkynyl, cycloalkyl, cycloalkylalkyl, cycloalkenyl, aryl, arylalkyl, heteroaryl, heteroarylalkyl, heterocyclic ring and heterocyclylalkyl;

at each occurrence 'm' and 'n' are independently selected from 0 to 2, both inclusive.

The embodiments below are illustrative of the present invention and are not intended to limit the claims to the specific embodiments exemplified.

According to another embodiment, specifically provided are compounds of the formula (Ia) in which R$^a$ is hydrogen, halogen (for example bromine), alkyl (for example methyl) or alkylaminoalkyl (for example dimethylaminomethyl or diethylaminomethyl).

According to one embodiment, specifically provided are compounds of the formula (Ia) in which R$^b$ is hydrogen or alkyl for example methyl.

According to yet another embodiment, specifically provided are compounds of the formula (Ia) in which R$^1$ and R$^2$ are independently hydrogen or alkyl for example methyl.

According to yet another embodiment, specifically provided are compounds of the formula (Ia) in which U is substituted or unsubstituted heterocycle, preferably thiazole or isoxazole.

According to yet another embodiment, specifically provided are compounds of the formula (Ia) in which V is substituted or unsubstituted aryl, preferably phenyl. In this embodiment the substitutents on phenyl may be one or more are independently selected from halogen (for example F, Cl or Br), haloalkyl (for example CF$_3$), alkoxy (for example methoxy, ethoxy, OCH$_2$CH(CH$_3$)$_2$, OCH$_2$C(CH$_3$)$_3$ or OCH$_2$CH$_2$CH(CH$_3$)$_2$), haloalkoxy (for example OCHF$_2$, OCF$_3$, OCH$_2$CF$_3$, OCH$_2$CH$_2$CF$_3$ or OCH$_2$CH$_2$CF$_3$), cycloalkylalkoxy (for example cyclopropylmethoxy, cyclobutylmethoxy or cyclopentylmethoxy) and, substituted or unsubstituted arylalkoxy (for example trifluoromethylbenzyloxy).

According to one embodiment, there is provided a compound of the formula (Ib):

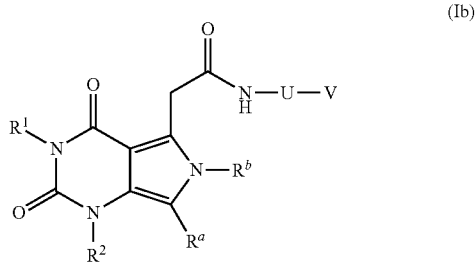

(Ib)

or a pharmaceutically acceptable salt thereof, wherein, U, V, $R^1$, $R^2$, $R^a$ and $R^b$ are as defined herein above.

According to one embodiment, there is provided a compound of the formula (Ic):

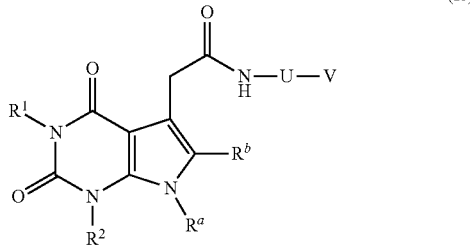

(Ic)

or a pharmaceutically acceptable salt thereof, wherein, U, V, $R^1$, $R^2$, $R^a$ and $R^b$ are as defined herein above.

The embodiments below are illustrative of the present invention and are not intended to limit the claims to the specific embodiments exemplified.

According to another embodiment, specifically provided are compounds of the formula (Ic) in which $R^a$ is hydrogen or alkyl (for example methyl).

According to one embodiment, specifically provided are compounds of the formula (Ic) in which $R^b$ is hydrogen.

According to yet another embodiment, specifically provided are compounds of the formula (Ic) in which $R^1$ and $R^2$ are independently hydrogen or alkyl (for example methyl).

According to yet another embodiment, specifically provided are compounds of the formula (Ic) in which U is substituted or unsubstituted heterocycle, preferably thiazole.

According to yet another embodiment, specifically provided are compounds of the formula (Ic) in which V is substituted or unsubstituted aryl, preferably phenyl. In this embodiment the substitutents on phenyl may be one or more and are independently selected from halogen (for example F, Cl or Br), haloalkyl (for example $CF_3$), alkoxy (for example $OCH_2C(CH_3)_3$ or haloalkoxy (for example $OCH_2CF_3$).

According to one embodiment, there is provided a compound of the formula (Id):

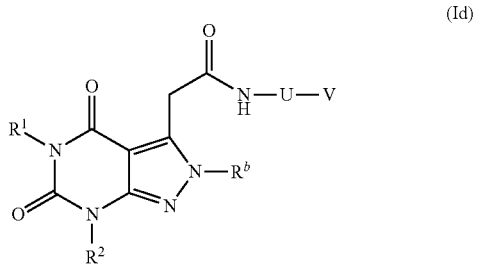

(Id)

or a pharmaceutically acceptable salt thereof, wherein, $R^1$, $R^2$, $R^b$, U and V are as defined herein above;

The embodiments below are illustrative of the present invention and are not intended to limit the claims to the specific embodiments exemplified.

According to one embodiment, specifically provided are compounds of the formula (Id) in which $R^1$ and $R^2$ are alkyl, preferably methyl.

According to another embodiment, specifically provided are compounds of the formula (Id) in which $R^b$ is hydrogen or ($C_1$-$C_4$) alkyl, preferably methyl.

According to yet another embodiment, specifically provided are compounds of the formula (Id) in which 'U' is substituted or unsubstituted five membered heterocycle, preferably thiazole or isoxazole.

According to yet another embodiment, specifically provided are compounds of the formula (Id) in which 'V' is substituted or unsubstituted aryl, preferably phenyl. In this embodiment the substitutents on phenyl may be one or more and are independently selected from halogen (for example F, Cl or Br), cyano, alkyl (for example t-butyl or iso-butyl), haloalkyl (for example $CF_3$) and haloalkoxy (for example $OCHF_2$, $OCF_3$ or $OCH_2CF_3$).

According to yet another embodiment, specifically provided are compounds of the formula (Id) in which U and V together form an optionally substituted fused ring system which may optionally include one or more heteroatoms selected from O, S and N. In this embodiment the fused ring system is benzothiazole and the optional substituent is haloalkoxy (for example $OCF_3$).

According to one embodiment, there is provided a compound of the formula (Ie):

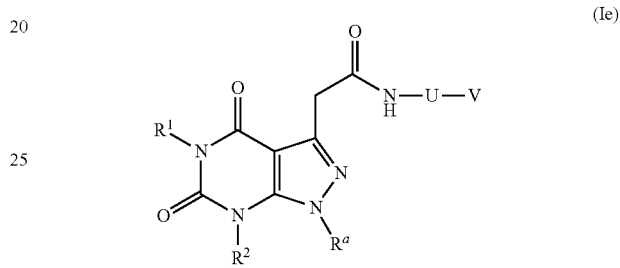

(Ie)

or a pharmaceutically acceptable salt thereof, wherein, $R^1$, $R^2$, $R^a$, U and V are as defined herein above;

According to one embodiment, there is provided a compound of the formula (If):

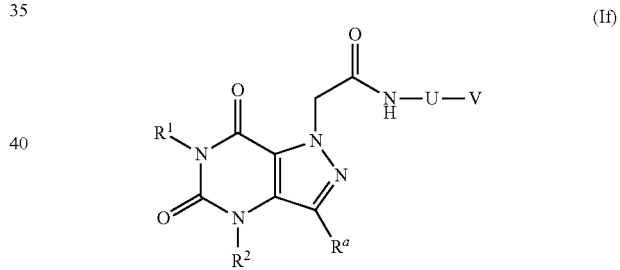

(If)

or a pharmaceutically acceptable salt thereof, wherein, $R^1$, $R^2$, $R^a$, U and V are as defined herein above;

The embodiments below are illustrative of the present invention and are not intended to limit the claims to the specific embodiments exemplified.

According to one embodiment, specifically provided are compounds of the formula (If) in which $R^1$ and $R^2$ are methyl.

According to another embodiment, specifically provided are compounds of the formula (If) in which $R^a$ is hydrogen or ($C_1$-$C_4$) alkyl.

According to yet another embodiment, specifically provided are compounds of the formula (If) in which 'U' is substituted or unsubstituted five membered heterocycle, preferably thiazole or oxazole.

According to yet another embodiment, specifically provided are compounds of the formula (If) in which 'V' is substituted or unsubstituted aryl, preferably phenyl. In this embodiment one or more substituents on phenyl may be same or different and are independently selected from halogen (for example F, Cl or Br), cyano, alkyl, haloalkyl (for example $CF_3$), alkoxy [for example $OCH_2CH(CH_3)_2$, $OCH_2CH_2CH(CH_3)_2$ or $OCH_2C(CH_3)_3$], cycloalkylalkoxy (for example cyclobutylmethoxy) and haloalkoxy (for example OCHF$_2$, OCF$_3$, OCH$_2$CF$_3$ or OCH$_2$CH$_2$CF$_3$).

Particularly contemplated are compounds of the formulas (I), (Ia), (Ib), (Ic), (Id), (Ie) and (If) which possess IC$_{50}$ of less than 250 nM, preferably, less than 100 nM, more preferably, less than 50 nM with respect to TRPA1 activity as measured by method as described in the present patent application.

It should be understood that the compounds of the formulas (I), (Ia), (Ib), (Ic), (Id), (Ie) and (If) structurally encompasses all stereoisomers, enantiomers and diastereomers and pharmaceutically acceptable salts that may be contemplated from the chemical structure of the genera described herein.

In accordance with another aspect, the present patent application provides a pharmaceutical composition that includes at least one compound described herein and at least one pharmaceutically acceptable excipient (such as a pharmaceutically acceptable carrier or diluent). Preferably, the pharmaceutical composition comprises a therapeutically effective amount of at least one compound described herein. The compounds described in the present patent application may be associated with a pharmaceutically acceptable excipient (such as a carrier or a diluent) or be diluted by a carrier, or enclosed within a carrier which can be in the form of a capsule, sachet, paper or other container.

The compounds and pharmaceutical compositions described herein are useful for modulating TRPA1 receptors, wherein modulation is believed to be related to a variety of disease states.

In accordance with another aspect, the present patent application further provides a method of inhibiting TRPA1 receptors in a subject in need thereof by administering to the subject one or more compounds described herein in the amount effective to cause inhibition of such receptor.

DETAILED DESCRIPTION OF THE INVENTION

The terms "halogen" or "halo" includes fluorine, chlorine, bromine or iodine.

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl and 1,1-dimethylethyl (tert-butyl). The term "C$_{1-6}$ alkyl" refers to an alkyl chain having 1 to 6 carbon atoms. Unless set forth or recited to the contrary, all alkyl groups described herein may be straight chain or branched, substituted or unsubstituted The term "alkenyl" refers to an aliphatic hydrocarbon group containing a carbon-carbon double bond and which may be a straight or branched chain having 2 to about 10 carbon atoms, e.g., ethenyl, 1-propenyl, 2-propenyl (allyl), iso-propenyl, 2-methyl-1-propenyl, 1-butenyl and 2-butenyl. Unless set forth or recited to the contrary, all alkenyl groups described herein may be straight chain or branched, substituted or unsubstituted.

The term "alkynyl" refers to a straight or branched chain hydrocarbyl radical having at least one carbon-carbon triple bond and having 2 to about 12 carbon atoms (with radicals having 2 to about 10 carbon atoms being preferred) e.g., ethynyl, propynyl and butynyl. Unless set forth or recited to the contrary, all alkynyl groups described herein may be straight chain or branched, substituted or unsubstituted.

The term "alkoxy" refers to a straight or branched, saturated aliphatic hydrocarbon radical bonded to an oxygen atom that is attached to a core structure. Examples of alkoxy groups include but are not limited to methoxy, ethoxy, propoxy, isopropoxy, butoxy, isobutoxy, tert-butoxy, pentoxy, 3-methyl butoxy and the like. Unless set forth or recited to the contrary, all alkoxy groups described herein may be straight chain or branched, substituted or unsubstituted.

The term "haloalkyl" and "haloalkoxy" means alkyl or alkoxy, as the case may be, substituted with one or more halogen atoms, where alkyl and alkoxy groups are as defined above. The term "halo" is used herein interchangeably with the term "halogen" means F, Cl, Br or I. Examples of "haloalkyl" include but are not limited to trifluoromethyl, difluoromethyl, 2,2,2-trifluoroethyl, pentafluoroethyl, pentachloroethyl 4,4,4-trifluorobutyl, 4,4-difluorocyclohexyl, chloromethyl, dichloromethyl, trichloromethyl, 1-bromoethyl and the like. Examples of "haloalkoxy" include but are not limited to fluoromethoxy, difluoromethoxy, trifluoromethoxy, 2,2,2-trifluoroethoxy, pentafluoroethoxy, pentachloroethoxy, chloromethoxy, dichloromethoxy, trichloromethoxy, 1-bromoethoxy and the like. Unless set forth or recited to the contrary, all "haloalkyl" and "haloalkoxy" groups described herein may be straight chain or branched, substituted or unsubstituted.

The term "cycloalkyl" denotes a non-aromatic mono or multicyclic ring system of 3 to about 12 carbon atoms, such as cyclopropyl, cyclobutyl, cyclopentyl and cyclohexyl. Examples of multicyclic cycloalkyl groups include, but are not limited to, perhydronapththyl, adamantyl and norbornyl groups, bridged cyclic groups or spirobicyclic groups, e.g., spiro(4,4)non-2-yl. Unless set forth or recited to the contrary, all cycloalkyl groups described herein may be substituted or unsubstituted.

The term "cycloalkylalkyl" refers to a cyclic ring-containing radical having 3 to about 8 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl and cyclopentylethyl. Unless set forth or recited to the contrary, all cycloalkylalkyl groups described herein may be substituted or unsubstituted.

The term "cycloalkylalkoxy" is used to denote alkoxy substituted with cycloalkyl, wherein 'alkoxy' and 'cycloalkyl' are as defined above (either in the broadest aspect or a preferred aspect). Examples of cycloalkylalkoxy groups include cyclopropylmethoxy, 1- or 2-cyclopropylethoxy, 1-, 2- or 3-cyclopropylpropoxy, 1-, 2-, 3- or 4-cyclopropyl-butoxy, cyclobutylmethoxy, 1- or 2-cyclobutylethoxy, 1-, 2- or 3-cyclobutylpropoxy, 1-, 2-, 3- or 4-cyclobutylbutoxy, cyclopentylmethoxy, 1- or 2-cyclopentylethoxy, 1-, 2- or 3-cyclopentylpropoxy, 1-, 2-, 3- or 4-cyclopentylbutoxy, cyclohexylmethoxy, 1- or 2-cyclohexylethoxy and 1-, 2- or 3-cyclohexylpropoxy. Preferably, 'cycloalkylalkoxy' is (C$_{3-6}$)cycloalkyl-(C$_{1-6}$)alkoxy. Unless set forth or recited to the contrary, all cycloalkylalkoxy groups described herein may be substituted or unsubstituted.

The term "cycloalkenyl" refers to a cyclic ring-containing radical having 3 to about 8 carbon atoms with at least one carbon-carbon double bond, such as cyclopropenyl, cyclobutenyl and cyclopentenyl. Unless set forth or recited to the contrary, all cycloalkenyl groups described herein may be substituted or unsubstituted.

The term "aryl" means a carbocyclic aromatic system containing one, two or three rings wherein such rings may be fused. If the rings are fused, one of the rings must be fully unsaturated and the fused ring(s) may be fully saturated, partially unsaturated or fully unsaturated. The term "fused" means that a second ring is present (ie, attached or formed) by having two adjacent atoms in common (i.e., shared) with the first ring. The term "fused" is equivalent to the term "condensed". The term "aryl" embraces aromatic radicals such as phenyl, naphthyl, tetrahydronaphthyl, indane and biphenyl. Unless set forth or recited to the contrary, all aryl groups described herein may be substituted or unsubstituted.

The term "arylalkyl" refers to an aryl group as defined above directly bonded to an alkyl group as defined above, e.g., —CH$_2$C$_6$H$_5$ or —C$_2$H$_4$C$_6$H$_5$. Unless set forth or recited to the contrary, all arylalkyl groups described herein may be substituted or unsubstituted.

The term "heterocyclic ring" refers to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazolyl, imidazolyl, tetrahydroisoqinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, indanyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl and isochromanyl. The heterocyclic ring radical may be attached to the main structure at any heteroatom or carbon atom that results in the creation of a stable structure. Unless set forth or recited to the contrary, all heterocyclic ring described herein may be substituted or unsubstituted.

The term "heterocyclyl" refers to a heterocyclic ring radical as defined above. The heterocyclyl ring radical may be attached to the main structure at any heteroatom or carbon atom that results in the creation of a stable structure. Unless set forth or recited to the contrary, all heterocyclyl groups described herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described herein may be substituted or unsubstituted.

The term "heteroaryl" refers to an aromatic heterocyclic ring radical. The heteroaryl ring radical may be attached to the main structure at any heteroatom or carbon atom that results in the creation of a stable structure. Unless set forth or recited to the contrary, all heteroaryl groups described herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described herein may be substituted or unsubstituted.

Unless otherwise specified, the term "substituted" as used herein refers to substitution with any one or more or any combination of the following substituents: hydroxy, halogen, carboxyl, cyano, nitro, oxo (=O), thio (=S), substituted or unsubstituted alkyl, substituted or unsubstituted haloalkyl, substituted or unsubstituted alkoxy, substituted or unsubstituted haloalkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine, —COOR$^{x'}$, —C(O)R$^{x'}$, —C(S)R$^{x'}$, —C(O)NR$^{x'}$R$^{y'}$, —C(O)ONR$^{x'}$R$^{y'}$, —NR$^{x'}$CONR$^{y'}$R$^{z'}$, —N(R$^{x'}$)SOR$^{y'}$, —N(R$^{x'}$)SO$_2$R$^{y'}$, —(=N—N(R$^{x'}$)R$^{y'}$), —NR$^{x'}$C(O)OR$^{y'}$, —NR$^{x'}$R$^{y'}$, —NR$^{x'}$C(O)R$^{y'}$, —NR$^{x'}$C(S)R$^{y'}$, —NR$^{x'}$C(S)NR$^{y'}$R$^{z'}$, —SONR$^{x'}$R$^{y'}$, —SO$_2$NR$^{x'}$R$^{y'}$, —OR$^{x'}$, —OR$^{x'}$C(O)NR$^{y'}$R$^{z'}$, —OR$^{x'}$C(O)OR$^{y'}$, —OC(O)R$^{x'}$, —OC(O)NR$^{x'}$R$^{y'}$, —R$^{x'}$NR$^{y'}$C(O)R$^{z'}$, —R$^{x'}$OR$^{y'}$, —R$^{x'}$C(O)OR$^{y'}$, —R$^{x'}$C(O)NR$^{y'}$R$^{z'}$, —R$^{x'}$C(O)R$^{y'}$, —R$^{x'}$OC(O)R$^{y'}$, —SR$^{x'}$, —SOR$^{x'}$, —SO$_2$R$^{x'}$ and —ONO$_2$, wherein R$^{x'}$, R$^{y'}$ and R$^{z'}$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl or substituted or unsubstituted heterocyclic ring.

The term "treating" or "treatment" of a state, disorder or condition includes; (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

The compounds described in the present patent application may form salts. Non-limiting examples of pharmaceutically acceptable salts forming part of this patent application include salts derived from inorganic bases salts of organic bases, salts of chiral bases, salts of natural amino acids and salts of non-natural amino acids.

Certain compounds of the present invention, including compounds of formula (I), (Ia), (Ib), (Ic), (Id), (Ie) and (If) are capable of existing in stereoisomeric forms (e.g. diastereomers and enantiomers). The present invention includes these stereoisomeric forms (including diastereomers and enantiomers) and mixtures of them. The various stereoisomeric forms of the compounds of the present invention may be separated from one another by methods known in the art or a given isomer may be obtained by stereospecific or asymmetric synthesis. Tautomeric forms and mixtures of compounds described herein are also contemplated.

Pharmaceutical Compositions

The pharmaceutical composition of the present patent application includes at least one compound described herein and at least one pharmaceutically acceptable excipient (such as a pharmaceutically acceptable carrier or diluent). Preferably, the pharmaceutical composition includes the compound(s) described herein in an amount sufficient to inhibit TRPA1 in a subject (e.g., a human). The inhibitory activity of compounds falling within the formulas (I), (Ia), (Ib), (Ic), (Id), (Ie) and (If) may be measured by an assay provided below.

The compound of the present invention may be associated with a pharmaceutically acceptable excipient (such as a carrier or a diluent) or be diluted by a carrier, or enclosed within a carrier which can be in the form of a capsule, sachet, paper or other container.

The pharmaceutical compositions may be prepared by techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application.

Methods of Treatment

The compounds and pharmaceutical compositions of the present invention can be administered to treat any disorder, condition, or disease treatable by inhibition of TRPA1. For instance, the compounds and pharmaceutical compositions of the present invention are suitable for treatment or prophylaxis of the following diseases, conditions and disorders mediated or associated with the activity of TRPA1 receptors: pain, chronic pain, complex regional pain syndrome, neuropathic pain, postoperative pain, rheumatoid arthritic pain, osteoarthritic pain, back pain, visceral pain, cancer pain, algesia, neuralgia, migraine, neuropathies, diabetic neuropathy, sciatica, HIV-related neuropathy, post-herpetic neuralgia, fibromyalgia, nerve injury, ischaemia, neurodegeneration, stroke, post stroke pain, multiple sclerosis, respiratory diseases, asthma, cough, COPD, inflammatory disorders, oesophagitis, gastroeosophagal reflux disorder (GERD), irritable bowel syndrome, inflammatory bowel disease, pelvic hypersensitivity, urinary incontinence, cystitis, burns, psoriasis, eczema, emesis, stomach duodenal ulcer and pruritus. The connection between therapeutic effect and inhibition of TRPA1 is illustrated, for example, in Story G M et al, *Cell*, 2003, 112, 819-829; McMahon S B and Wood J N, *Cell*, 2006, 124, 1123-1125; Voorhoeve P M et al., *Cell*, 2006, 124, 1169-1181; Wissenbach U, Niemeyer B A and Flockerzi V, *Biology of the Cell*, 2004, 96, 47-54; Dayne Y O, Albert Y H & Michael X, *Expert Opinion on Therapeutic Targets*, 2007, 11(3), 391-401 and the references cited therein.

Pain can be acute or chronic. While acute pain is usually self-limiting, chronic pain persists for 3 months or longer and can lead to significant changes in a patient's personality; lifestyle, functional ability and overall quality of life (K. M. Foley, *Pain*, in Cecil Textbook of Medicine; J. C. Bennett & F. Plum (eds.), 20th ed., 1996, 100-107). The sensation of pain can be triggered by any number of physical or chemical stimuli and the sensory neurons which mediate the response to this harmful stimulus are termed as "nociceptors". Nociceptors are primary sensory afferent (C and Aδ fibers) neurons that are activated by a wide variety of noxious stimuli including chemical, mechanical, thermal and proton (pH<6) modalities. Nociceptors are the nerves which sense and respond to parts of the body which suffer from damage. They signal tissue irritation, impending injury, or actual injury. When activated, they transmit pain signals (via the peripheral nerves as well as the spinal cord) to the brain.

Chronic pain can be classified as either nociceptive or neuropathic. Nociceptive pain includes tissue injury-induced pain and inflammatory pain such as that associated with arthritis. Neuropathic pain is caused by damage to the sensory nerves of the peripheral or central nervous system and is maintained by aberrant somatosensory processing. The pain is typically well localized, constant and often with an aching or throbbing quality. Visceral pain is the subtype of nociceptive pain that involves the internal organs. It tends to be episodic and poorly localized. Nociceptive pain is usually time limited, meaning when the tissue damage heals, the pain typically resolves (arthritis is a notable exception in that it is not time limited).

General Methods of Preparation

The compounds described herein, including compounds of general formula (I), (Ia), (Ib), (Ic), (Id), (Ie) and (If) and specific examples, can be prepared by techniques known to one in the art, for example, through the reaction scheme depicted in Schemes 1-12. Furthermore, in the following schemes, where specific acids, bases, reagents, coupling agents, solvents etc. are mentioned, it is understood that other suitable acids, bases, reagents, coupling agents etc. may be used and are included within the scope of the present invention. Modifications to reaction conditions, for example, temperature, duration of the reaction or combinations thereof are envisioned as part of the present invention. The compounds obtained by using the general reaction scheme may be of insufficient purity. These compounds can be purified by any of the methods for purification of organic compounds known in the art, for example, crystallization or silica gel or alumina column chromatography using different solvents in suitable ratios. All possible stereo isomers are envisioned within the scope of this invention.

An approach for the synthesis of 2,4-dioxo-1,2,3,4-tetrahydro-5H-pyrrolo[3,2-d]pyrimidin-5-yl)acetamide of the general formula (Ia-1) where $R^1$, $R^2$, U and V are as defined herein above is depicted in Scheme 1. The starting substituted uracil derivative of formula (1), wherein $R^1$ and $R^2$ are alkyl (e.g., methyl, ethyl) are available commercially or can be prepared by reaction of 1,3-dialkylurea and acetic anhydride or by condensation of monosubstituted urea and ethyl acetoacetate according to methods known in the art (Egg, H. et al. *Synthesis*, 1982, 1071-1073; Senda S. et al. *Chem. Pharm. Bull.*, 1972, 6, 404-408). Nitro derivative of general formula (2) can be prepared by nitration of uracil derivative of formula (1) using mixture of sulphuric acid and fuming nitric acid followed by condensation with DMF-dimethyl acetal in a suitable solvent (e.g., DMF, THF). Reductive cyclization of compound of formula (2) using 10% Pd—C under hydrogen atmosphere in suitable solvent (e.g., EtOH, MeOH) affords compound of general formula (3). Alkylation of compound of formula (3) using appropriate electrophile of a general formula (4) [prepared from haloacetyl halide and appropriate substituted amine as described in Ohkubo M. et al., *Chem. Pharm. Bull.*, 1995, 43(9), 1497-1504] in the presence of a suitable base (e.g., NaH, $K_2CO_3$) affords compound of general formula (Ia-1).

Scheme 1

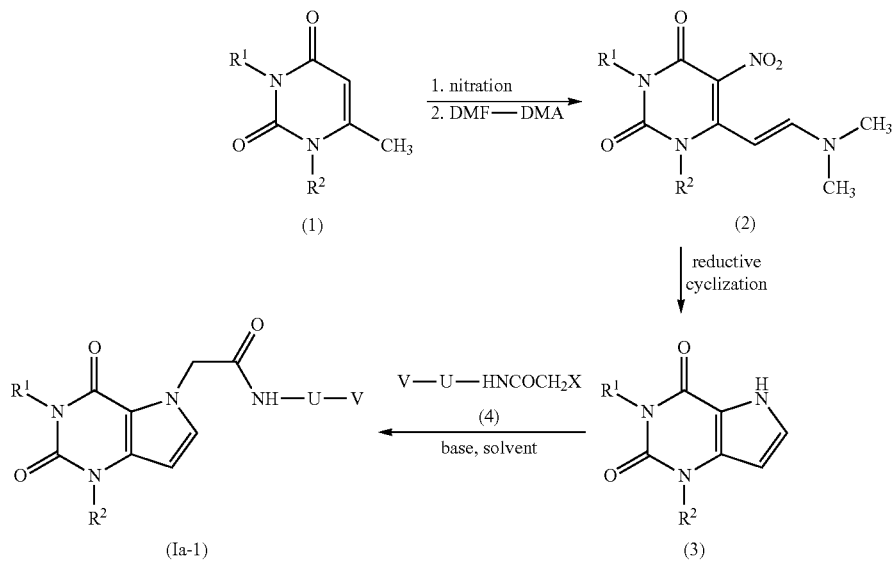

An approach for the synthesis of compounds of the general formula (Ia-2) where $R^1$, $R^2$, U and V are as defined herein above is depicted in Scheme 2. Compounds of general formula (3) is converted to a compound of formula (6) by using suitable amine of formula (5) [wherein R and R' are alkyl (e.g., methyl, ethyl)] and formaldehyde as described by Tsupak, E. B. et al. in *Chemistry of Heterocyclic Compounds*, 1994, 30(9), 1077-1082. Alternatively, the intermediate (6) can be prepared by formylation of compound of formula (3) using mixture of phosphorous oxychloride and dimethyl formamide to give compound of formula (7) followed by reductive amination of the formyl group using a suitable amine of formula (5). Alkylation of compound of formula (6) using appropriate electrophile of a general formula (4) in the presence of a suitable base (e.g., NaH, $K_2CO_3$) affords compounds of general formula (Ia-2).

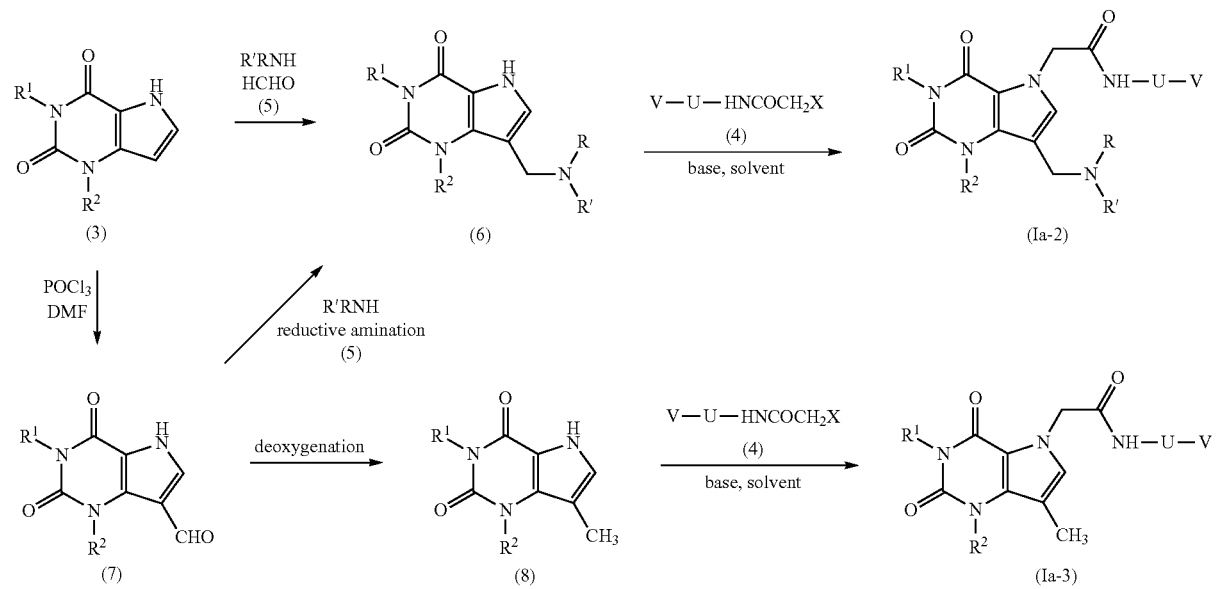

An approach for the synthesis of compounds of the general formula (Ia-3) where $R^1$, $R^2$, U and V are as defined herein above is also depicted in Scheme 2. Deoxygenation of formyl pyrrole of formula (7) with suitable reducing system (e.g., triethylsilane/trifluoroacetic acid) affords methylpyrrole of formula (8). Alkylation of compound of formula (8) using appropriate electrophile of a general formula (4) in the presence of a suitable base (e.g., NaH, $K_2CO_3$) affords compounds of the general formula (Ia-3).

An approach for the synthesis of compounds of the general formula (Ia-4) where $R^1$, $R^2$, U and V are as defined herein above is also depicted in Scheme 3. Halogenation of compound of formula (3) with suitable halogenating agent (e.g., N-bromosuccinimide, N-iodosuccinimide, bromine) gives corresponding halogenated compound of formula (9). Alkylation of compound of formula (9) using appropriate electrophile of a general formula (4) in the presence of a suitable base (e.g., NaH, $K_2CO_3$) affords compounds of general formula (Ia-4).

Scheme 3

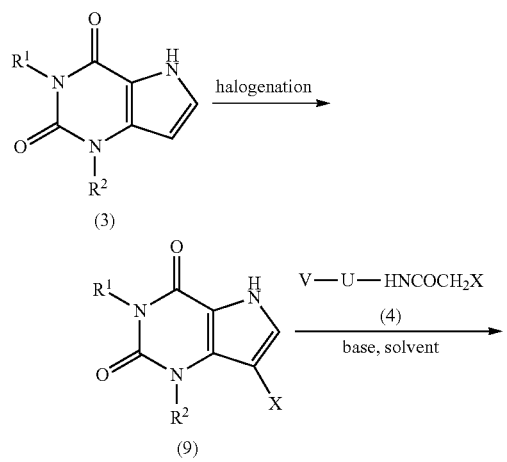

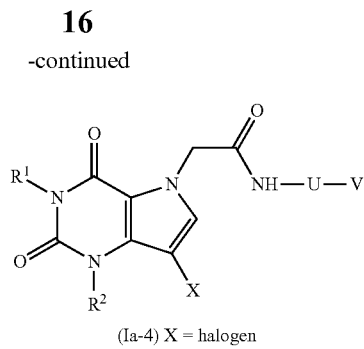

(Ia-4) X = halogen

An approach for the synthesis of compounds of the general formula (Ia-5) where $R^1$, $R^2$, U and V are as defined herein above is also depicted in Scheme 4. 1,3,6-trimethyl-1H-pyrrolo[3,2-d]pyrimidine-2,4(3H,5H)-dione of the formula (12) can be prepared by the reaction of 5-amino-1,3-dimethyluracil of the formula (10) with propargyl bromide in a suitable solvent such as MeOH followed by cyclization of the intermediate (11) at elevated temperature as described in Townsend, L. B. et al., *J. Heterocyclic Chem.*, 1975, 12, 711-716 and Kawahara, N. et al., *Chem. Pharm. Bull.*, 1985, 33(11), 4740-4748. Alkylation of compound of formula (12) with an appropriate electrophile of a general formula (4) affords compounds of general formula (Ia-5).

Scheme 4

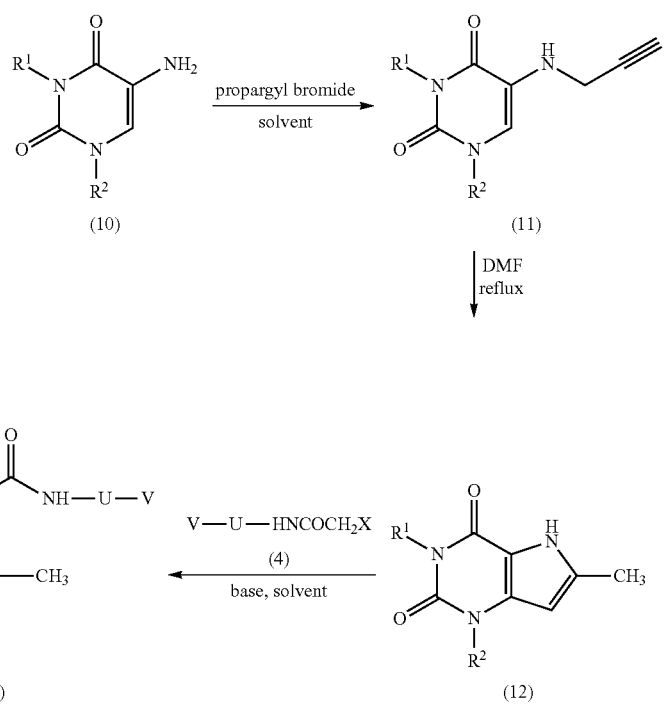

A general approach for the synthesis of 2,4-dioxo-2,3,4,6-tetrahydro-1H-pyrrolo[3,4-d]pyrimidin-5-yl)acetamide of the general formula (Ib-1) where $R^1$, $R^2$, $R^b$, U and V are as defined herein above is depicted in Scheme 5. The formyl derivative of formula (13) can be prepared by formylation of uracil derivative of formula (1) [Senda, S. et al., *Yakugaku Zasshi*, 1971, 91, 1372] followed by bromination of formyl derivative thus formed. Cyclization of formyl derivative of formula (13) [as described in Senda, S. et al., *Synthesis*, 1978, 463-465] with amine of the formula (19) in suitable solvent (e.g., EtOAc) followed by halogenation using suitable halogenating reagent (e.g., N-bromosuccinimide, N-iodosuccinimide, $Br_2$ in acetic acid) gives halopyrrole of general formula (14). Halopyrrole of formula (14) on reaction with allyl boronic acid pinacol ester of the formula (15) in the presence of a palladium catalyst, such as bis(triphenylphosphine)palladium dichloride or tetrakis(triphenylphosphine) palladium (0) gives allyl pyrrole of the formula (16) [procedure is similar to the Suzuki-Miyaura Coupling described by Kotha, et al., *Synlett*, 2005, 12, 1877-1890]. Transformation of allyl pyrrole of formula (16) into corresponding aldehyde can be accomplished by methods known in the art [e.g., Postema, M. H. D. et al., in *J. Org. Chem.*, 2003, 68, 4748-4754]. Further oxidation of aldehyde thus formed can be carried out by oxidation methods well known in the literature to give corresponding carboxylic acid of general formula (17). Coupling of carboxylic acid (17) with appropriate amines of formula (18) using a standard amide coupling method gives compounds of general formula (Ib-1).

A general approach for the synthesis of 2,4-dioxo-2,3,4,7-tetrahydro-1H-pyrrolo[2,3-d]pyrimidin-5-yl)acetamide of the general formula (Ic-1) where $R^a$ is an alkyl group, $R^1$, $R^2$, U and V are as defined above is depicted in Scheme 6. Reaction of 6-chlorouracil derivative of the formula (20) with amino ester of formula (21) followed by cyclization gives pyrrolidinone of formula (22) [Similar procedure described by Edstrom, E. D. et al., *J. Org. Chem.*, 1995, 60, 5069-5076]. Pyrrolidinone of formula (22) can be converted to halopyrrole of formula (23) (wherein X is halogen) using triflic anhydride or hydrazine followed by iodine. Halopyrrole of formula (23) on reaction with allyl boronic acid pinacol ester of the formula (15) in the presence of a palladium catalyst, such as bis(triphenylphosphine)palladium dichloride or tetrakis (triphenylphosphine) palladium(0) gives allyl pyrrole of the formula (24). Transformation of allyl pyrrole of formula (24) to the corresponding aldehyde followed by further oxidation of aldehyde thus formed can be carried out by oxidation methods well known in the literature to give corresponding carboxylic acid of general formula (25). Coupling of carboxylic acid of formula (25) with appropriate amines of formula (18) by using a standard amide coupling method gives compounds of general formula (Ic-1).

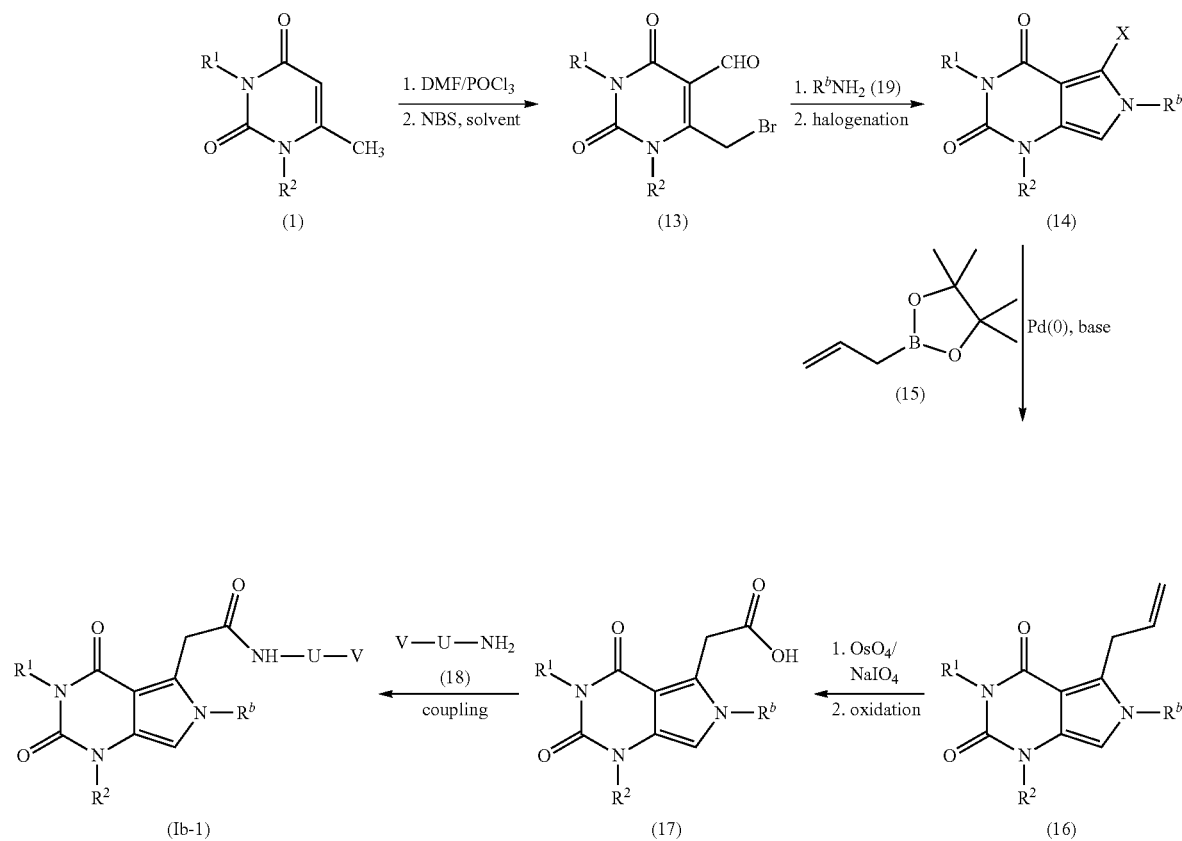

Scheme 5

Scheme 6

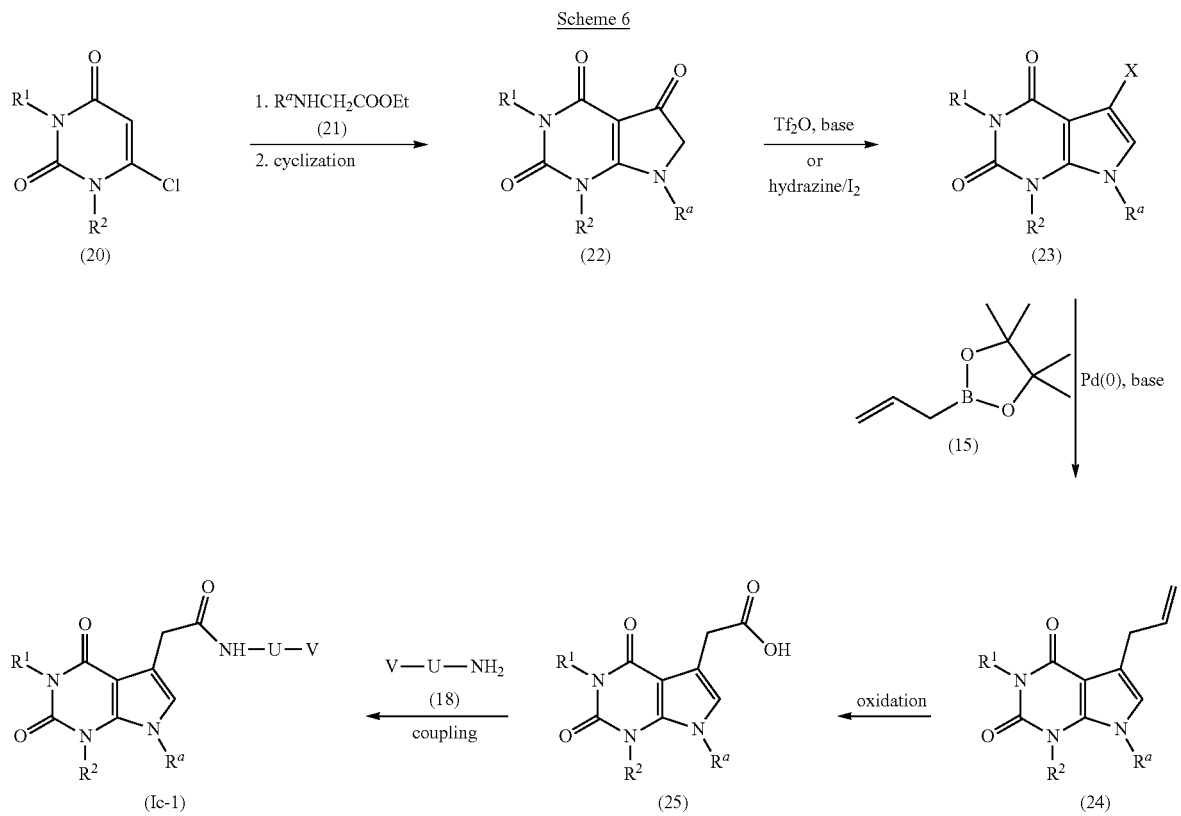

An alternative approach for the synthesis of compounds of the general formula (Ic-1) is described in Scheme 7. Reaction of commercially available 6-aminouracil derivative of the formula (26) with chloroacetaldehyde dimethyl acetal gives pyrrole derivative (as described by Noell, C. W. et al., *J. Het. Chem.*, 1964, 34-41) which upon alkylation with appropriate alkylating agent ($R^aX$) gives compound of formula (27). Compound of formula (27) can be converted into α-keto ester of general formula (28) using oxalyl chloride followed by reaction of acid chloride thus formed with anhydrous protic solvent (e.g., methanol, ethanol, tert-butanol). Deoxygenation of α-keto ester of general formula (28) with triethylsilane in the presence of trifluoroacetic acid affords ester of general formula (29) [similar procedure described by Han, Q. et al., *J. Med. Chem.*, 2000, 43, 4398-4415]. Acidic hydrolysis of ester of formula (29) gives corresponding carboxylic acid of formula (25). Coupling of carboxylic acid of formula (25) with appropriate amines of formula (18) by using a standard amide coupling method give compounds of general formula (Ic-1).

Scheme 7

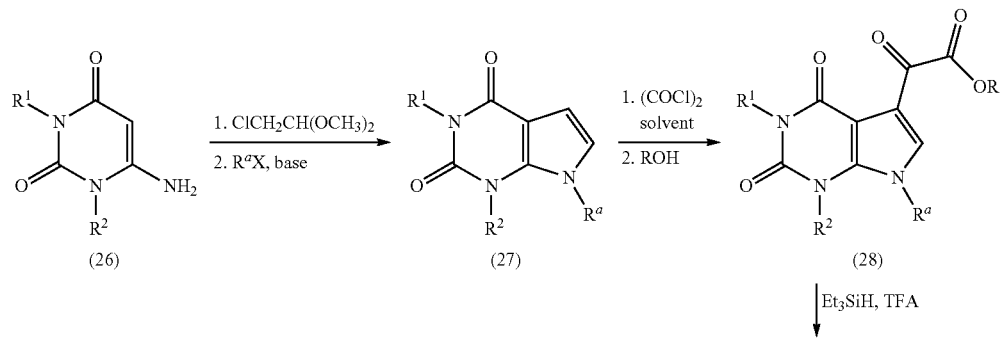

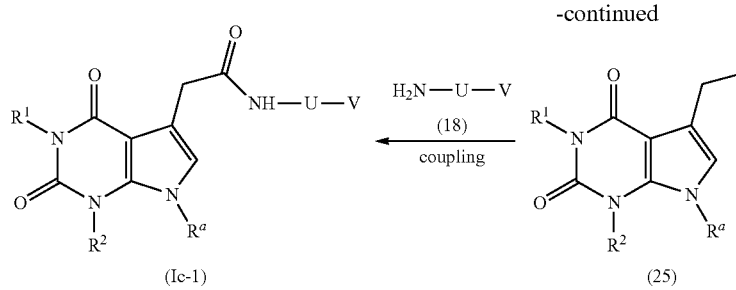
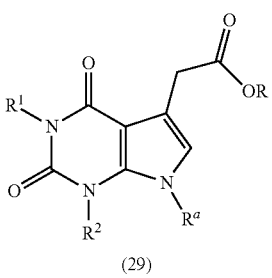

An approach for the synthesis of compounds of the general formula (Id-1) where $R^1$, $R^2$, U and V are as defined herein above is depicted in Scheme 8. The synthesis starts from known 6-hydrazino-1,3-dimethyluracil (30) which is readily prepared by the displacement of halogen of 6-chloro-1,3-dialkyuracil of the formula (20) with hydrazine hydrate according to the known procedure. The cyclisation of compound of the formula (30) with acetic anhydride gave pyrazole of the formula (31). The deacetylation followed by selective N-alkylation of pyrazole (31) with dimethyl sulfate afforded compounds of the formula (33) (Pfleiderer, W. et al., Justus Liebigs Ann Chem. 1958, 615, 42-47). The reaction of compound of formula (33) with dimethyl carbonate in presence of a strong base (e.g. NaH) under reflux conditions gives ester of the formula (34). Hydrolysis of ester (34) with aqueous acid afforded the desired pyrazolo[3,4-d]pyrimidinedione acetic acid of the formula (35). The coupling of compound of formula (35) with respective amines of formula (18) by using a standard amide coupling method gives compounds of general formula (Id-1).

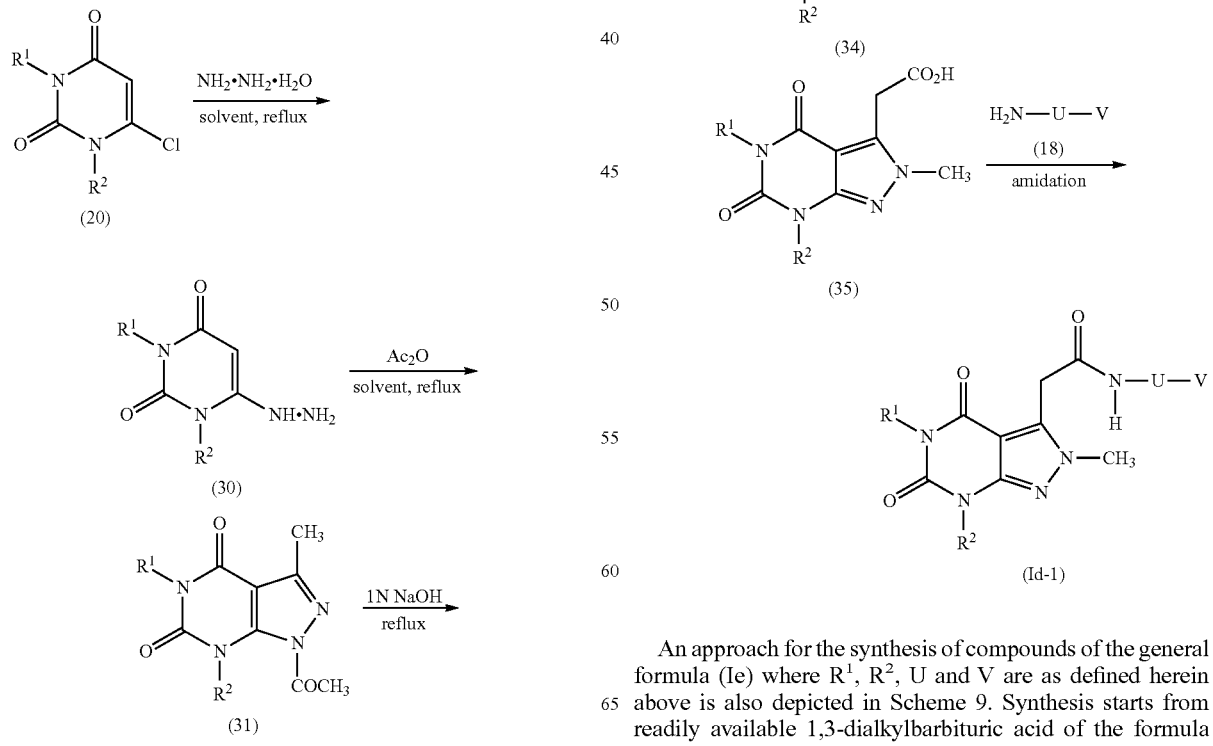

An approach for the synthesis of compounds of the general formula (Ie) where $R^1$, $R^2$, U and V are as defined herein above is also depicted in Scheme 9. Synthesis starts from readily available 1,3-dialkylbarbituric acid of the formula (36). The known 6-chloro-5-formyl-1,3-dimethyluracil of formula (37) wherein $R^1$ and $R^2$ are methyl is prepared according to a reported procedure (Singh, J. S. et al., *Synthesis*, 1988, 342-344). The reaction of 6-chloro-5-formyl-1,3-dimethyluracil (37) with hydroxylamine in methanol followed by dehydration with phosphorous oxychloride give 6-chloro-5-cyano-1,3-dimethyluracil of formula (38). The cyclisation of compounds of the formula (38) with alkylhydrazine of the formula (39) in the presence of suitable base afforded amino pyrazole of the formula (40). The amino pyrazole (40) on diazotization followed by halide substitution with copper halide (such as copper bromide or copper iodide) gives a halide derivative of the formula (41) (wherein X is halogen). Suzuki-Miyaura coupling reaction of aryl halide of formula (41) with allyl boronic acid pinacol ester of the formula (15) as described by Kotha et al., *Synlett*, 2005, 12, 1877-1890) gives allyl pyrazole of the formula (42). This can be converted to pyrazolo[3,4-d]pyrimidinylacetic acid of the formula (43) by oxidative cleavage methods well known in the literature. The coupling of carboxylic acid of the formula (43) with respective amines of formula (18) by using a standard amide coupling method can give compounds of general formula (Ie).

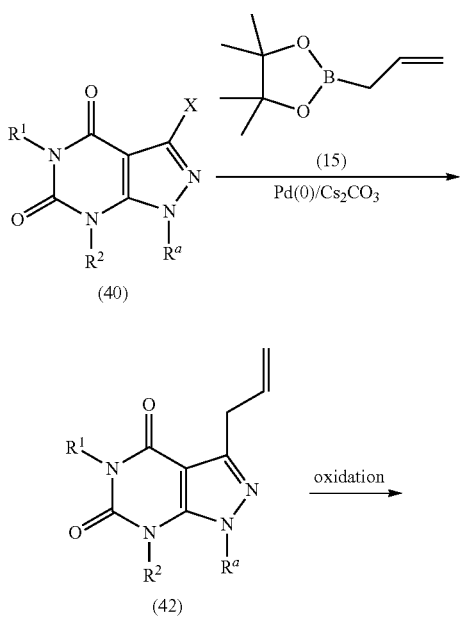

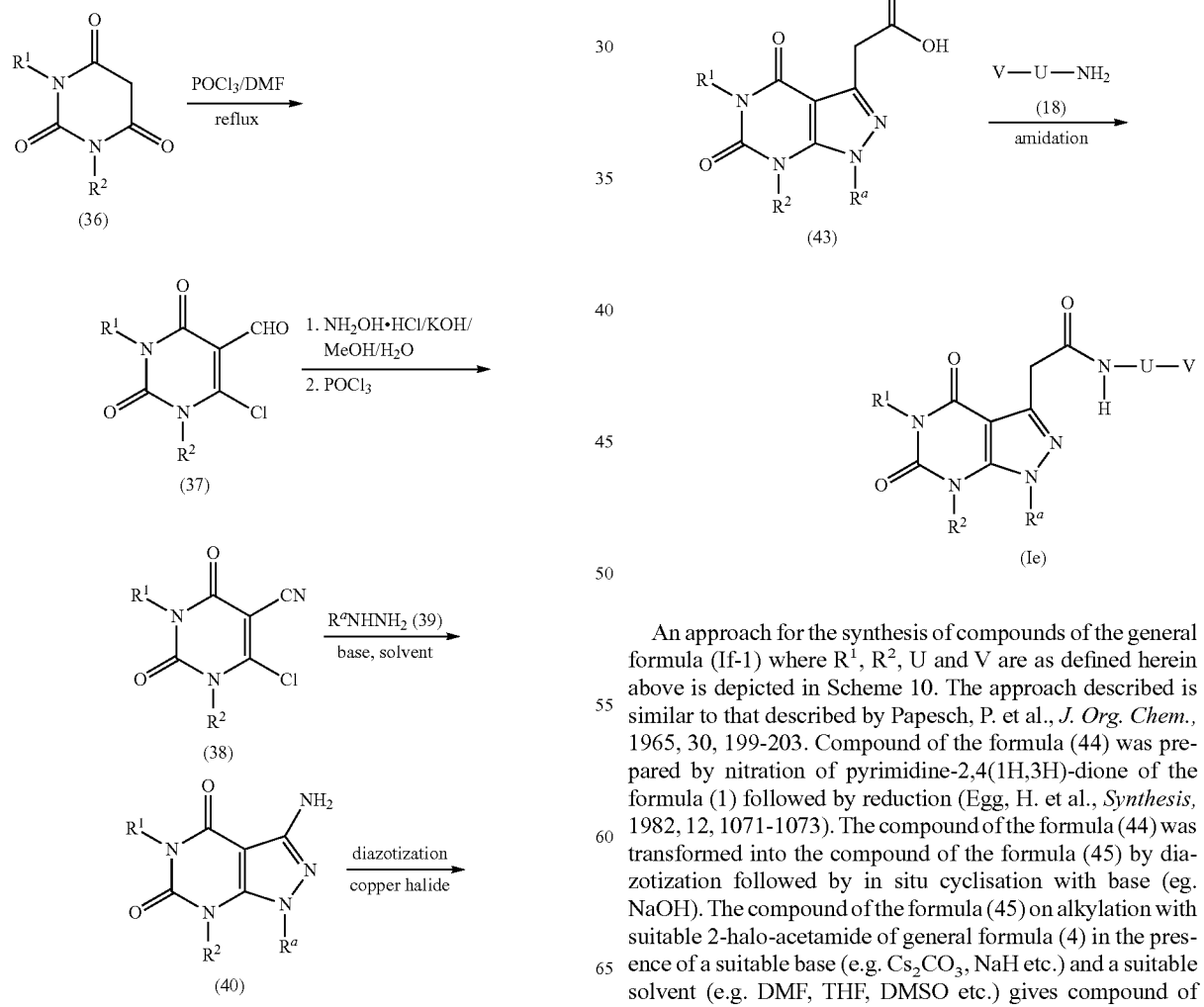

An approach for the synthesis of compounds of the general formula (If-1) where $R^1$, $R^2$, U and V are as defined herein above is depicted in Scheme 10. The approach described is similar to that described by Papesch, P. et al., *J. Org. Chem.*, 1965, 30, 199-203. Compound of the formula (44) was prepared by nitration of pyrimidine-2,4(1H,3H)-dione of the formula (1) followed by reduction (Egg, H. et al., *Synthesis*, 1982, 12, 1071-1073). The compound of the formula (44) was transformed into the compound of the formula (45) by diazotization followed by in situ cyclisation with base (eg. NaOH). The compound of the formula (45) on alkylation with suitable 2-halo-acetamide of general formula (4) in the presence of a suitable base (e.g. $Cs_2CO_3$, NaH etc.) and a suitable solvent (e.g. DMF, THF, DMSO etc.) gives compound of general formula (If-1).

Scheme 10

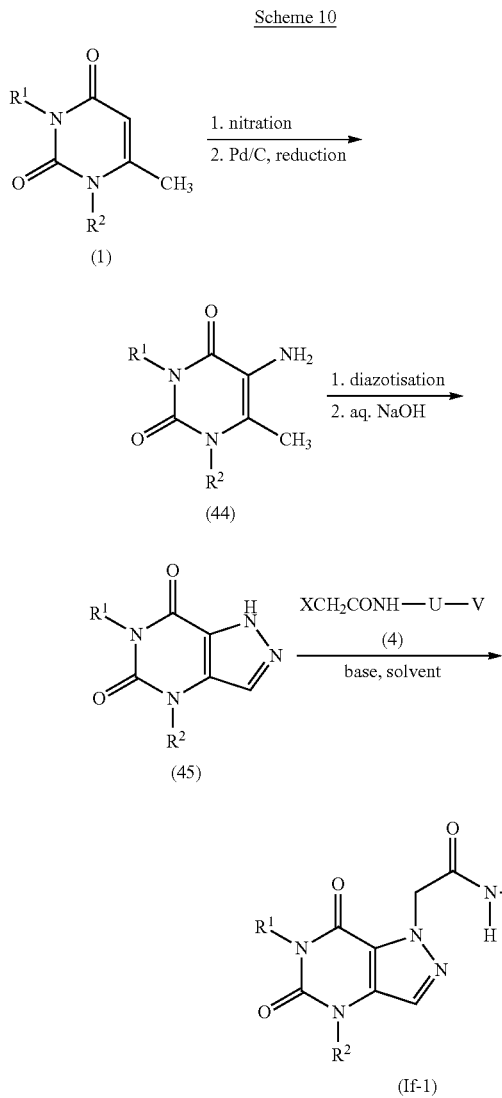

The 2-haloacetamides of formula (53) (wherein $R^z$ is selected from alkyl, cyano, halogen, haloalkyl, alkoxy, haloalkoxy, cycloalkylalkoxy and arylalkoxy, and 'p' is selected from 0 to 5) required for the synthesis of compound of the present invention can be prepared according to methods known to one skilled in the art (Carroll, L. et al., *J. Am. Chem. Soc.*, 1950, 72, 3722-3725; Ohkubo, M. et al., *Chem. Pharm. Bull.*, 1995, 43(9), 1497-1504). Thus, acylation of an aryl, heteroaryl or aryl alkyl amine with bromoacetyl bromide in the presence of a suitable base such as triethylamine or pyridine gives N-substituted bromoacetamide of the general formula (53) (Scheme 11).

A few of aniline derivatives, arylalkylamines and 2-amino-4-arylthiazoles (52) were commercially available. Many of the disubstituted and trisubstituted arylaminothiazoles were prepared from appropriate aryl alkyl ketones. Commercially unavailable aryl alkyl ketones were prepared from the corresponding benzoic acids as shown in Scheme 11. Substituted benzoic acid of the formula (46) was converted to the corresponding acetophenone in three steps as shown in Scheme 11. Thus, acid (46) was converted to the corresponding acid chloride (47) using oxalyl chloride in the presence of catalytic amounts of DMF in dry dichloromethane. Alternatively, this transformation can be carried out using excess thionyl chloride. The acid chloride (47) was converted to corresponding Weinreb amide (48) by treating with N,O-dimethyl hydroxylamine hydrochloride in the presence of a suitable base such as triethylamine. Addition of methyl magnesium iodide to Weinreb amide (48) gives acetophenone derivative of the formula (49). In addition, commercially unavailable aryl alkyl ketones were prepared from mono or di-substituted phenol (50) as depicted in Scheme 11. Thus, acetylation of phenol (50) with acetic anhydride followed by Fries rearrangement of the ester formed in the presence of Lewis acid (e.g. $AlCl_3$) affords corresponding hydroxyacetophenone of general formula (51). Alkylation of hydroxyacetophenone of general formula (51) with suitable alkyl halide in suitable base (e.g., NaH, $Cs_2CO_3$) and suitable solvent (e.g., DMSO, THF, DMF) gives acetophenone derivative of general formula (49).

The aryl alkyl ketone of the formula (49) is converted to 2-aminothiazole of the formula (52) in one step by its reaction with thiourea in the presence of iodine in ethanol. This conversion is similar to the one described by Carroll, K. et al., *J. Am. Chem. Soc.* 1950, 3722; and Naik, S., J.; Halkar, U. P., *ARKIVOC*, 2005, xiii, 141-149. Alternatively, 2-aminothiazoles of the formula (52) can be prepared by the reaction of compounds of formula (49) with bromine in acetic acid to give the alpha halo intermediate, which on reaction with thiourea in THF at reflux condition give compounds of the formula (52). The compound of the formula (52) is converted to 2-bromo-N-thiazolyl acetamide of the formula (53) by acylation with bromoacetyl bromide in the presence of a suitable base (e.g., pyridine or triethylamine) and in a suitable solvent (e.g., THF, DMF).

Scheme 11

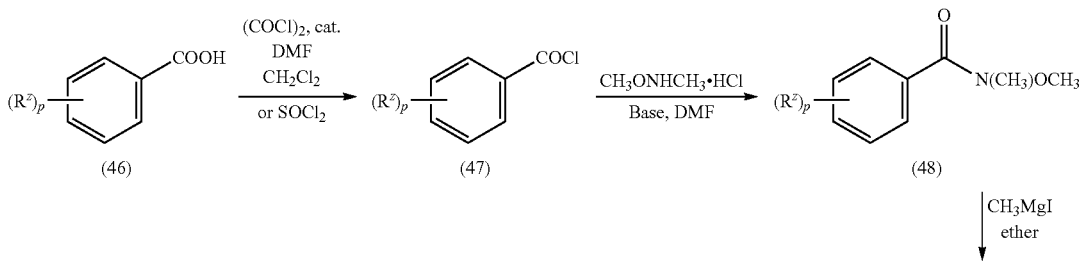

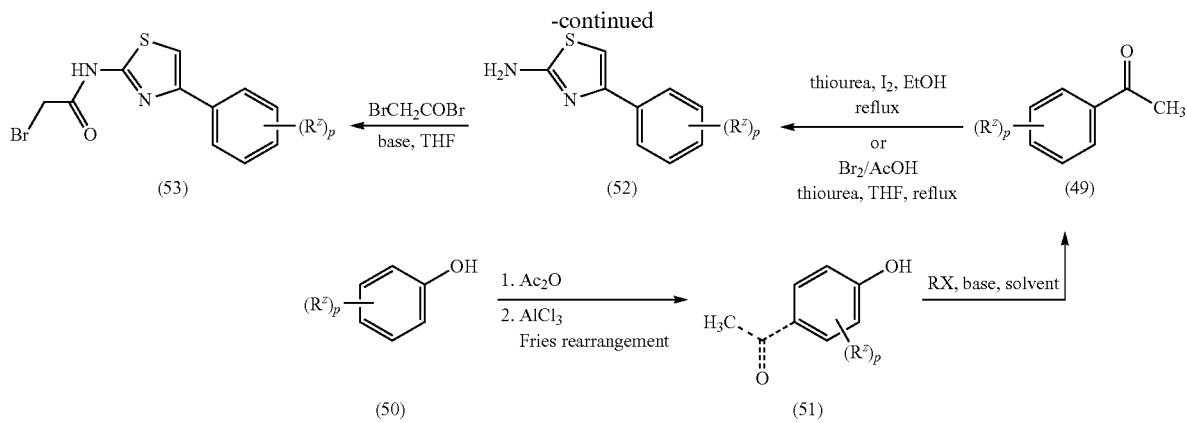

5-Aryl-1H-imidazol-2-amines of the formula (55) were prepared as shown in Scheme 12. The reaction of acetophenones of the formula (49) (wherein $R^z$ and 'p' are as defined above in scheme 11) with bromine in acetic acid to give the alpha bromo intermediate, which on reaction with acetyl guanidine in acetonitrile at reflux condition give compounds of the formula (54). The deacetylation of (54) in the presence of catalytic amount of concentrated sulphuric acid using suitable solvent afforded desired 5-Aryl-1H-imidazol-2-amine of the formula (55). (This is similar to procedure reported by Thomas, L. et al., *J. Org. Chem.*, 1994, 59, 7299-7305).

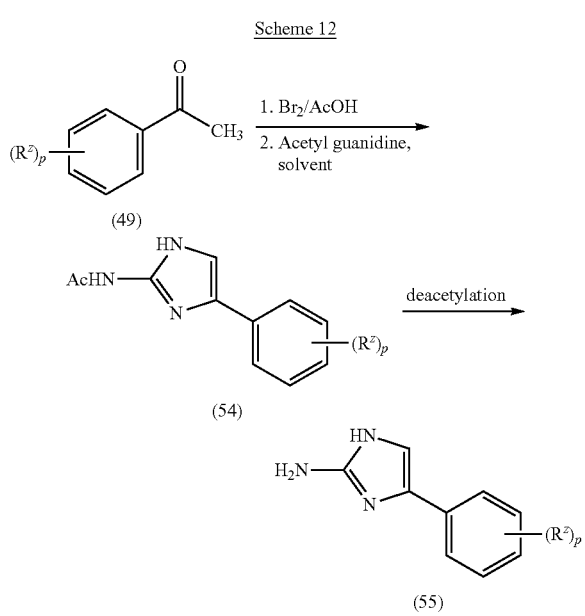

The intermediates and examples described in the present invention are prepared using the procedure described below. However, it is understood that these intermediates and examples can be prepared by alternate approaches which are within the scope of the present invention.

Experimental

Unless otherwise stated, work-up includes distribution of the reaction mixture between the organic and aqueous phase indicated within parentheses, separation of layers and drying the organic layer over sodium sulphate, filtration and evaporation of the solvent. Purification, unless otherwise mentioned, includes purification by silica gel chromatographic techniques, generally using ethyl acetate/petroleum ether mixture of a suitable polarity as the mobile phase. Use of a different eluent system is indicated within parentheses. The following abbreviations are used in the text: DMSO-$d_6$: Hexadeuterodimethyl sulfoxide; DMF: N,N-dimethylformamide, M.P.: Melting point; J: Coupling constant in units of Hz; RT or rt: room temperature (22-26° C.). Aq.: aqueous AcOEt: ethyl acetate; equiv. or eq.: equivalents.

Intermediate 1

1,3-Dimethyl-1H-pyrrolo[3,2-d]pyrimidine-2,4(3H,5H)-dione

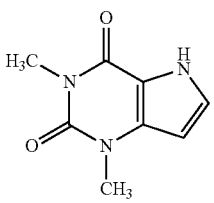

Step 1

1,3,6-Trimethyl-5-nitrouracil: A mixture of concentrated $H_2SO_4$ (7.0 mL) and fuming $HNO_3$ (7.0 mL) was cooled to 0-5° C. and 1,3,6-trimethylpyrimidine-2,4(1H,3H)-dione (3.5 g, 22.702 mmol) was gradually added to the reaction mixture. After stirring for 2 h. at the same temperature the reaction mixture was partitioned between ethyl acetate (200 mL) and water (100 mL). The organic layer was washed with brine (2×50 mL), dried ($Na_2SO_4$) and evaporated under reduced pressure. Crude product obtained was purified by column chromatography to give 1.30 g of the product as yellow solid; $^1H$ NMR (δ ppm, 300 MHz, DMSO-$d_6$) 2.38 (s, 3H), 3.20 (s, 3H), 3.40 (s, 3H); APCI-MS (m/z) 198.30 (M−H).

Step 2

1,3-Dimethyl-6-[2-(dimethylamino)vinyl]-5-nitrouracil:
To a solution of Step 1 intermediate, 1,3,6-Trimethyl-5-nitrouracil (0.60 g, 3.012 mmol) in dry N,N-dimethylformamide (5.0 mL) was added N,N-dimethylformamide dimethyl acetal (0.53 g, 4.447 mmol) and the reaction mixture was stirred at room temperature for 2 h. After this time, diethyl ether was added to the reaction mixture and the precipitate was collected by filtration and washed with diethyl ether to give 0.45 g of the product as brownish solid; $^1$H NMR ($\delta$ ppm, 300 MHz, DMSO-$d_6$) 2.98 (s, 6H), 3.16 (s, 3H), 3.40 (s, 3H), 4.78 (d, J=12.6 Hz, 1H), 7.05 (d, J=12.6 Hz, 1H); APCI-MS (m/z) 255.11 (M+H)$^+$.

Step 3

1,3-Dimethyl-1H-pyrrolo[3,2-d]pyrimidine-2,4(3H,5H)-dione: To a solution of Step 2 intermediate (0.40 g, 1.573 mmol) in MeOH (80 mL) was added 10% Pd—C (0.2 g) and the mixture was stirred under a hydrogen atmosphere at room temperature for 2 h. The mixture was filtered through a celite bed and was thoroughly washed with MeOH (50 mL). The filtrate was collected and evaporated and the residue thus obtained was purified by column chromatography to afford 0.120 g of the desired compound as an off-white solid; $^1$H NMR ($\delta$ ppm, 300 MHz, DMSO-$d_6$) 3.23 (s, 3H), 3.38 (s, 3H), 6.17 (s, 1H), 7.25 (s, 1H), 12.09 (s, 1H); APCI-MS (m/z) 180.28 (M+H)$^+$.

Intermediate 2

1,3,6-Trimethyl-1H-pyrrolo[3,2-d]pyrimidine-2,4(3H,5H)-dione

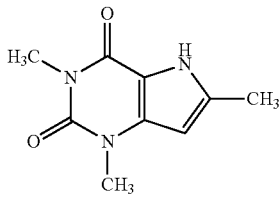

Step 1

5-Amino-1,3-dimethylpyrimidine-2,4(1H,3H)-dione: To a stirred solution of 1,3-dimethyl-5-nitropyrimidine-2,4(1H,3H)-dione (2.0 g, 10.802 mmol) in methanol (200 mL), 10% Pd—C (0.500 g) was added under hydrogen atmosphere and the reaction mixture was stirred at room temperature for 2 h. Reaction mixture was filtered through a celite bed and washed with methanol. The filtrate was collected and concentrated under reduced pressure to give 1.5 g of the product.

Step 2

1,3-Dimethyl-5-(prop-2-yn-1-ylamino)pyrimidine-2,4(1H,3H)-dione: To a stirred solution of Step 1 intermediate (1.4 g, 9.023 mmol) in 1:1 mixture of dichloromethane and methanol (28 mL) was added propargyl bromide (1.4 mL) and the mixture was stirred at room temperature for 2 h. Reaction mixture was filtered through celite bed and washed with methanol. The filtrate was concentrated under reduced pressure to give 500 mg of the product.

Step 3

1,3,6-Trimethyl-1H-pyrrolo[3,2-d]pyrimidine-2,4(3H,5H)-dione: A solution of Step 2 intermediate (500 mg, 2.587 mmol) in dry N,N-dimethylformamide (20 mL) was refluxed for 40 h under nitrogen atmosphere. The excess of solvent was evaporated and the residue obtained was purified by silica gel column chromatography by using 5% methanol in chloroform to obtain 200 mg of the product as a yellow solid; $^1$H NMR ($\delta$ ppm, 300 MHz, DMSO-$d_6$) 2.26 (s, 3H), 3.21 (s, 3H), 3.33 (s, 3H), 5.91 (s, 1H), 11.84 (br s, 1H); ESI-MS (m/z) 194.28 (M+H)$^+$.

Intermediate 3

1,3,7-Trimethyl-1H-pyrrolo[3,2-d]pyrimidine-2,4(3H,5H)-dione

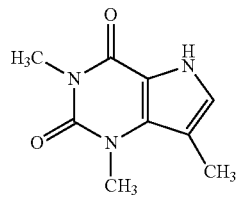

Step 1

1,3-Dimethyl-2,4-dioxo-2,3,4,5-tetrahydro-1H-pyrrolo[3,2-d]pyrimidine-7-carbaldehyde: At a temperature of 5-10° C., phosphorous oxychloride (1.84 ml, 20.087 mmol) was mixed with N,N-dimethylformamide (2 mL). Then a solution of Intermediate 1 (600 mg, 3.348 mmol) in N,N-dimethylformamide (3 mL) was added while stirring. The reaction mixture was held for 2 h at 95° C., cooled and poured onto ice (10 g). The precipitate formed was filtered off and recrystallised from water to give 300 mg of the product as an off-white solid; $^1$H NMR ($\delta$ ppm, 300 MHz, DMSO-$d_6$) 3.25 (s, 3H), 3.75 (s, 3H), 8.06 (s, 1H), 9.79 (s, 1H), 13.15 (br s, 1H); APCI-MS (m/z) 208.20 (M+H)$^+$.

Step 2

1,3,7-Trimethyl-1H-pyrrolo[3,2-d]pyrimidine-2,4(3H,5H)-dione: To a stirred and cooled (−10° C.) solution of trifluoroacetic acid (5 mL) was added triethylsilane (294 mg, 2.528 mmol) followed by portionwise addition of Step 1 intermediate (150 mg, 0.723 mmol). The reaction mixture was warmed to room temperature and stirred for another 1 h. Reaction mixture was diluted with ethyl acetate (25 mL) and water (25 mL). Two layers were separated. The aqueous layer was extracted with ethyl acetate (2×25 mL). The combined organic layers were washed with water (25 mL), dried (Na$_2$SO$_4$) and filtered. The filtrate was evaporated to give 110 mg of the product as an off-white solid; $^1$H NMR ($\delta$ ppm, 300 MHz, DMSO-$d_6$) 2.27 (s, 3H), 3.22 (s, 3H), 3.56 (s, 3H), 7.03 (s, 1H), 11.75 (br s, 1H); APCI-MS (m/z) 194.28 (M+H)$^+$.

Intermediate 4

7-Bromo-1,3-dimethyl-1H-pyrrolo[3,2-d]pyrimidine-2,4(3H,5H)-dione

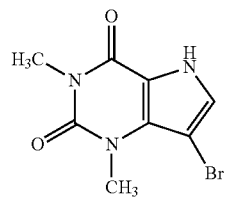

To a solution of Intermediate 1 (500 mg, 2.800 mmol) in acetic acid (5 mL) was added a solution of bromine (430 mg, 2.700 mmol) in acetic acid (5 mL) dropwise with stirring, after which water (1.2 mL) was added. The reaction mixture was stirred for another 20 min and diluted with two volumes of cold water. After 3 h, the precipitate was filtered off and washed with diethyl ether to afford 400 mg of the product as a white solid; $^1$H NMR ($\delta$ ppm, 300 MHz, DMSO-$d_6$) 3.23 (s, 3H), 3.65 (s, 3H), 7.42 (s, 1H), 12.59 (br s, 1H); APCI-MS (m/z) 258.19 (M+H)$^+$.

Intermediate 5

7-[(Dimethylamino)methyl]-1,3-dimethyl-1H-pyrrolo[3,2-d]pyrimidine-2,4(3H,5H)-dione

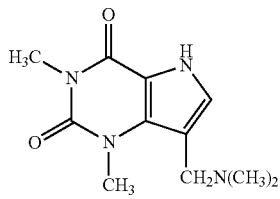

To a mixture of 50% dimethyl amine (0.4 mL), acetic acid (0.4 mL) and 38% formaldehyde (0.4 mL) were added, after which Intermediate 1 (0.4 g, 2.232 mmol) was added. The reaction mixture was refluxed for 10 min and then held for 20 min at 90° C. Reaction mixture was cooled to room temperature and diluted with water (25 mL). Two layers were separated. The aqueous layer was extracted with ethyl acetate (2×25 mL). The combined organic layers were washed with water (25 mL), dried (Na$_2$SO$_4$) and filtered. The filtrate was evaporated to give a crude product which was recrystallised from acetonitrile to give 97 mg of the product as a white solid; $^1$H NMR ($\delta$ ppm, 300 MHz, DMSO-$d_6$) 2.08 (s, 6H), 3.23 (s, 3H), 3.30 (s, 2H), 3.69 (s, 3H), 7.13 (s, 1H), 11.93 (br s, 1H); APCI-MS (m/z) 237.00 (M+H)$^+$.

Intermediate 6

7-[(Diethylamino)methyl]-1,3-dimethyl-1H-pyrrolo[3,2-d]pyrimidine-2,4(3H,5H)-dione

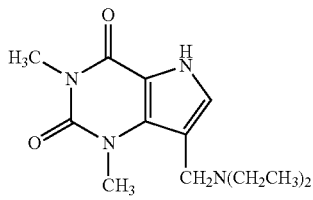

To a stirred solution of diethyl amine (52 mg, 0.723 mmol) in dichloromethane (5 mL) Intermediate 3, Step 1 (150 mg, 0.723 mmol) was added portionwise followed by the addition of sodium triacetoxyborohydried (230 mg, 1.085 mmol) at room temperature. After stirring for 24 h, the excess of solvent was evaporated and the crude product obtained was purified by column chromatography by using 1% methanol in chloroform to afford 130 mg of the product as a white solid; $^1$H NMR ($\delta$ ppm, 300 MHz, DMSO-$d_6$) 0.93 (t, J=7.2 Hz, 6H), 2.40-2.56 (m, 4H), 3.23 (s, 3H), 3.48 (s, 2H), 3.73 (s, 3H), 7.18 (s, 1H), 11.92 (br s, 1H); APCI-MS (m/z) 265.00 (M+H)$^+$.

Intermediate 7

(1,3,7-Trimethyl-2,4-dioxo-2,3,4,7-tetrahydro-1H-pyrrolo[2,3-d]pyrimidin-5-yl)acetic acid

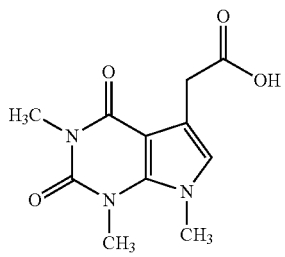 [SMILES: Cn1c(=O)c2c(CC(=O)O)cn(C)c2n(C)c1=O]

Step 1

1,3-Dimethyl-1H-pyrrolo[2,3-d]pyrimidine-2,4(3H,7H)-dione: To a stirred solution of chloroacetaldehyde dimethyl acetal (26.0 g, 208.717 mmol) in water (60 mL) concentrated hydrochloric acid (4 mL) was added at room temperature and the reaction mixture was stirred at near boiling until a homogeneous solution was obtained. Solution of sodium acetate (8.0 g, 97.525 mmol) was then added. The resulting mixture was then added to a stirred solution consisting of 6-amino-1,3-dimethyl uracil (20.0 g, 128.907 mmol) and sodium acetate (16.0 g, 195.051) in water (100 mL) at 90° C. All solid material was dissolved, then after 10 min. a precipitate was started to form. The reaction mixture was stirred for another 30 min. at the same temperature. The reaction mixture was cooled to room temperature and solid obtained was filtered, washed with water (2×250 mL) and then acetone (2×150 mL). The solid obtained was dried in oven at 65° C. to obtain 7.81 g of the product as an off-white solid; $^1$H NMR ($\delta$ ppm, 300

MHz, DMSO-$d_6$) 3.20 (s, 3H), 3.42 (s, 3H), 6.35 (s, 1H), 6.77 (s, 1H), 11.71 (br s, 1H); APCI-MS (m/z) 180.25 (M+H)$^+$.

Step 2

7-[(Dimethylamino)methyl]-1,3-dimethyl-1H-pyrrolo[3,2-d]pyrimidine-2,4(3H,5H)-dione: To a stirred solution of sodium hydroxide (3.4 g, 84.830 mmol) in water (80 mL) was added Step 1 intermediate (7.6 g, 42.415 mmol) at room temperature and the reaction mixture was stirred for 30 min. Dimethyl sulfate (10.7 g, 84.830 mmol) was added dropwise to the reaction mixture and stirred for another 4 h. Solid was precipitated out and collected by filtration, washed with water. The crude solid obtained was purified by column chromatography by using 3% methanol in chloroform to obtain 5.4 g of the product as a white solid; $^1$H NMR (δ ppm, 300 MHz, DMSO-$d_6$) 3.20 (s, 3H), 3.70 (s, 3H), 3.90 (s, 3H), 6.32 (s, 1H), 6.69 (s, 1H); APCI-MS (m/z) 194.21 (M+H)$^+$.

Step 3

Methyl oxo(1,3,7-trimethyl-2,4-dioxo-2,3,4,7-tetrahydro-1H-pyrrolo[2,3-d]pyrimidin-5-yl)acetate: To a well stirred solution of oxalyl chloride (1.6 g, 12.939 mmol) in dichloromethane (10 mL) was added Step 2 intermediate (1.0 g, 5.176 mmol) in small portions at −10° C. and the resulting mixture was stirred overnight at room temperature. The excess of solvent was removed under vacuum and the residue was again taken in dichloromethane (10 mL). The reaction mixture was cooled to −10° C. and dry methanol (10 mL) was added dropwise over a period of 10-15 min. The resulting reaction mixture was stirred overnight at room temperature. Excess of solvent was evaporated under vacuum. The residue obtained was basified with saturated solution of NaHCO$_3$ (25 mL) and extracted with ethyl acetate (2×50 mL). The combined organic layers were washed with water (25 mL), brine (25 mL) and dried (Na$_2$SO$_4$). The crude product obtained after evaporation of the solvent was purified by silica gel column chromatography by using 5% methanol in chloroform to give 1.1 g of the product as a pale yellow solid; $^1$H NMR (δ ppm, 300 MHz, DMSO-$d_6$) 3.20 (s, 3H), 3.62 (s, 3H), 3.72 (s, 6H), 3.83 (s, 2H), 6.29 (s, 1H); APCI-MS (m/z) 266.23 (M+H)$^+$.

Step 4

Methyl (1,3,7-trimethyl-2,4-dioxo-2,3,4,7-tetrahydro-1H-pyrrolo[2,3-d]pyrimidin-5-yl)acetate: To a stirred solution of triethylsilane (364 mg, 3.133 mmol) in trifluoroacetic acid (4.0 mL) was added Step 3 intermediate (250 mg, 0.892 mmol) slowly at −10° C. The resulting mixture was warmed slowly to room temperature. After overnight stirring at room temperature, excess of solvent was removed under reduced pressure and the residue obtained was neutralized with saturated solution of NaHCO$_3$ (15 mL). Two layers were separated after the addition of ethyl acetate (25 mL). The aqueous layer was extracted with ethyl acetate (2×25 mL). The combined organic layers were washed with water (25 mL) and brine (25 mL). The crude product obtained was purified by silica gel column chromatography by using 20% ethyl acetate in petroleum ether to give 147 mg of the product as a white solid; $^1$H NMR (δ ppm, 300 MHz, DMSO-$d_6$) 3.20 (s, 3H), 3.65-3.72 (m, 8H), 6.29 (s, 1H), 12.62 (br s, 1H); APCI-MS (m/z) 252.38 (M+H)$^+$.

Step 5

(1,3,7-Trimethyl-2,4-dioxo-2,3,4,7-tetrahydro-1H-pyrrolo[2,3-d]pyrimidin-5-yl)acetic acid: A mixture of Step 4 intermediate (130 mg, 0.491 mmol) and concentrated hydrochloric acid (4 mL) was heated at 60° C. for 2 h. The excess of hydrochloric acid was evaporated under reduced pressure and the residue obtained was purified by silica gel column chromatography using 5% methanol in chloroform to obtain 94 mg of the product as a white solid; $^1$H NMR (δ ppm, 300 MHz, DMSO-$d_6$) 3.21 (s, 3H), 3.65-3.72 (m, 8H), 6.29 (s, 1H), 12.62 (br s, 1H); APCI-MS (m/z) 252.38 (M+H)$^+$.

Intermediate 8

2,5,7-Trimethyl-4,6-dioxo-4,5,6,7-tetrahydro-2H-pyrazolo[3,4-d]pyrimidin-3-yl)acetic acid

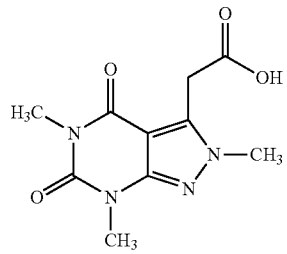 [SMILES: Cn1nc2c(c1CC(=O)O)c(=O)n(C)c(=O)n2C]

Step 1

6-Chloro-1,3-dimethylpyrimidine-2,4(1H,3H)-dione: To a stirred solution of 1,3-dimethylbarbituric acid (20.0 g, 128.09 mmol) in water (10 ml), phosphorous oxychloride (80 ml) was added slowly in externally cooling condition and then the reaction was slowly warmed to room temperature. After refluxing for 3 h the reaction mixture was allowed to cool to 0° C. and quenched with ice cold water (350 ml). The reaction mixture was extracted with chloroform (2×200 ml) and the combined organic extracts were washed with water (2×100 ml), dried over Na$_2$SO$_4$ and concentrated. The residue obtained was purified by silica gel column chromatography using 5% ethyl acetate in chloroform to obtain 21 g of the product as a pale brown solid; $^1$H NMR (300 MHz, CDCl$_3$) δ 3.33 (s, 3H), 3.57 (s, 3H), 5.94 (s, 1H).

Step 2

6-Hydrazino-1,3-dimethylpyrimidine-2,4(1H,3H)-dione: A mixture of Step 1 intermediate (17 g, 97.34 mmol) and hydrazine hydrate (119 ml) in isopropyl alcohol (280 ml) were refluxed for 1 h. The excess of solvent was removed under reduced pressure, solid obtained was filtered, washed with methanol (25 ml) and dried to obtain 8.1 g of the product as white solid; $^1$H NMR (300 MHz, DMSO-$d_6$): δ 3.09 (s, 3H), 3.21 (s, 3H), 4.37 (br s, 2H), 5.10 (s, 1H), 8.02 (br s, 1H).

Step 3

1-Acetyl-3,5,7-trimethyl-1H-pyrazolo[3,4-d]pyrimidine-4,6(5H,7H)-dione: A mixture of Step 2 intermediate (8.0 g, 47.01 mmol) and acetic anhydride (40 ml) in dry pyridine (78 ml) were refluxed for 3 h. The reaction mixture was cooled to 0° C. and acidified with 1N HCl (200 ml). The solid obtained was collected by filtration, washed with 1 N HCl (25 ml), water (25 ml) and dried to give 6.9 g of the product as a white solid; $^1$H NMR (300 MHz, DMSO-$d_6$): δ 2.71 (s, 3H), 2.96 (s, 3H), 3.37 (s, 3H), 3.50 (s, 3H).

Step 4

3,5,7-Trimethyl-1H-pyrazolo[3,4-d]pyrimidine-4,6(5H,7H)-dione: Step 3 above intermediate (6.9 g, 29.211 mmol) was refluxed in 1 N sodium hydroxide (69 ml) for 10 min. The reaction mixture was cooled to room temperature and poured into ice water and stirred for 2 h. The precipitated solid was collected by filtration and dried to give 5.1 g of the desired product as off-white solid; $^1$H NMR (300 MHz, CF$_3$CO$_2$D): δ 3.05 (s, 3H), 3.78 (s, 3H), 3.93 (s, 3H).

Step 5

2,3,5,7-Tetramethyl-2H-pyrazolo[3,4-d]pyrimidine-4,6(5H,7H)-dione: A solution of Step 4 intermediate (5.2 g, 26.77 mmol) in 1 N sodium hydroxide (52 ml) was added dimethylsulphate (5.2 ml) and stirred at room temperature for 1 h. The reaction mixture was diluted with water and the solid precipitated out was filtered, washed with water and dried to give 3.85 g of the product as off white solid; $^1$H NMR (300 MHz, CDCl$_3$): δ 2.59 (s, 3H), 3.36 (s, 3H), 3.48 (s, 3H), 3.79 (s, 3H).

Step 6

Methyl (2,5,7-trimethyl-4,6-dioxo-4,5,6,7-tetrahydro-2H-pyrazolo[3,4-d]pyrimidin-3-yl)acetate: To a stirred solution of Step 5 intermediate (3.8 g, 18.24 mmol) in dimethylcarbonate (91 ml) was added sodium hydride (60% dispersion in mineral oil, 4.5 g, 187.5 mmol) at room temperature. The reaction mixture was heated to reflux for overnight. The reaction mixture was cooled to room temperature, quenched into 1N HCl (200 ml), extracted with ethyl acetate (2×250 ml) and the combined organic layers were washed with water (2×250 ml), dried over Na$_2$SO$_4$ and concentrated. The residue obtained was triturated in hexane, solid obtained was filtered to give 5.5 g of the product as a white solid; $^1$H NMR (300 MHz, DMSO-d$_6$): δ 3.37 (s, 3H), 3.50 (s, 3H), 3.82 (s, 5H), 3.90 (s, 3H).

Step 7

(2,5,7-Trimethyl-4,6-dioxo-4,5,6,7-tetrahydro-2H-pyrazolo[3,4-d]pyrimidin-3-yl)acetic acid: A mixture of Step 6 intermediate (1.0 g, 3.755 mmol) and 6 N H$_2$SO$_4$ (9.3 ml) in dioxane (9.3 ml) stirred at reflux temperature for 2 h to give a homogeneous pale yellow solution. This solution was cooled, diluted with water and extracted with ethyl acetate (2×50 ml). The combined organic layers were washed with water, dried over Na$_2$SO$_4$ and concentrated. The residue obtained was triturated in diethyl ether, solid obtained was collected by filtration to give 330 mg of the product as a white solid; $^1$H NMR (300 MHz, DMSO-d$_6$): δ 3.17 (s, 3H), 3.34 (s, overlapping with DMSO, 3H), 3.79 (s, 3H), 4.11 (s, 2H), 12.95 (br s, 1H) and $^1$H NMR (300 MHz, CDCl$_3$): δ 3.39 (s, 3H), 3.50 (s, 3H), 3.88 (s, 3H), 4.10 (s, 2H).

Intermediate 9

4,6-Dimethyl-1H-pyrazolo[4,3-d]pyrimidine-5,7(4H,6H)-dione

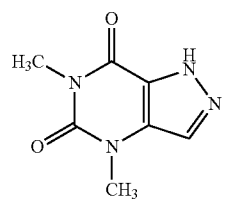

Step 1

5-Amino-1,3,6-trimethylpyrimidine-2,4(1H,3H)-dione: To a stirred suspension of 5-nitro-1,3,6-trimethylpyrimidine-2,4(1H,3H)-dione (4.2 g, 20.084 mmol) in 1:1 mixture of methanol and toluene (200 ml) was added 10% Pd—C (1.2 g). The reaction mixture was stirred under hydrogen atmosphere at room temperature overnight. The mixture was then filtered over a celite bed and was thoroughly washed with methanol (200 ml). The filtrate was collected and evaporated to give viscous residue which was then purified by column chromatography to afford 4.1 g of the product as an off-white solid.

Step 2

4,6-Dimethyl-1H-pyrazolo[4,3-d]pyrimidine-5,7(4H,6H)-dione: To a stirred solution of Step 1 intermediate (4.0 g, 23.634 mmol) in a mixture of ice (24 g) and concentrated HCl (5 ml) was added a solution of sodium nitrite (1.42 g, 20.580 mmol) in water (5 ml). The resulting suspension was stirred below 10° C. for 30 min. The solid formed at this stage was removed by filtration and the filtrate was added slowly with continuous stirring to 20% aq. NaOH (20 ml) by maintaining the temperature below 10° C. After addition the basic solution was filtered and neutralized with hydrochloric acid (5 N HCl). The precipitate separated was filtered and dried to get 300 mg of the product as dark orange solid; $^1$H NMR (300 MHz, DMSO-d$_6$): δ 3.45 (s, 3H), 3.52 (s, 3H), 7.53 (s, 1H).

Intermediate 10

3,4,6-Trimethyl-1H-pyrazolo[4,3-d]pyrimidine-5,7(4H,6H)-dione

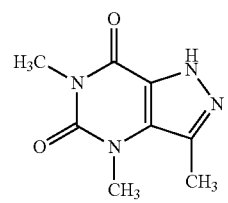

The title compound was prepared in 2 steps from 6-ethyl-1,3-dimethyl-5-nitropyrimidine-2,4(1H,3H)-dione (3.5 g, 16.279 mmol) as described in intermediate 9 to give 110 mg of the product as a white solid; $^1$H NMR (300 MHz, DMSO-d$_6$) δ 2.62 (s, 3H), 3.45 (s, 3H), 3.67 (s, 3H), 11.59 (br s, 1H); ESI-MS (m/z) 193.31 (M–H).

Intermediate 11

4-[3-fluoro-4-(trifluoromethyl)phenyl]-1H-imidazol-2-amine

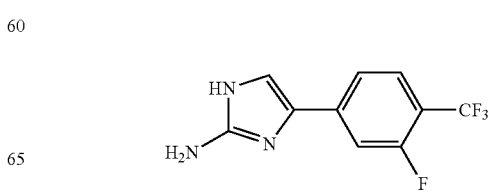

Step 1

N-{-4-[3-fluoro-4-(trifluoromethyl)phenyl]-1H-imidazol-2-yl}acetamide: To a stirred solution of 2-bromo-1-[3-fluoro-4-(trifluoromethyl)phenyl]ethanone (4.5 g, 15.73 mmol) in acetonitrile (45 ml) was added acetyl guanidine (2.38 g, 23.60 mmol). The reaction mixture was stirred and refluxed for overnight. The solvent was evaporation under reduced pressure and diluted with water and extracted with ethyl acetate (75 ml×3) and organic layers were washed with brine, dried ($Na_2SO_4$) and filtered. The filtrate was concentrated under reduced pressure and the residue obtained after the evaporation of the solvent was purified by silica gel column chromatography using 2% methanol in chloroform to obtain 1.15 g of the product as a yellow solid; $^1$H NMR (300 MHz, DMSO-$d_6$): δ 2.07 (s, 3H), 7.58 (s, 1H), 7.69-7.78 (m, 3H), 11.31 (br s, 1H), 11.91 (br s, 1H).

Step 2

4-[3-fluoro-4-(trifluoromethyl)phenyl]-1H-imidazol-2-amine: To a stirred solution of Step 1 intermediate (1.1 g, 3.829 mmol) in a mixture of methanol (20 ml) and water (20 ml) was added conc. $H_2SO_4$ (2 ml) and the resulting mixture was refluxed for 24 h. The reaction mixture was cooled to room temperature, saturated solution of potassium carnonate was added and extracted with ethyl acetate (2×50 ml). The organic layers were combined and dried over $Na_2SO_4$ and filtered. The filtrate was concentrated under reduced pressure. The residue obtained after the evaporation of the solvent was purified by silica gel column chromatography using 5% methanol in chloroform to obtain 290 mg of the product as a yellow solid; $^1$H NMR (300 MHz, DMSO-$d_6$): δ 5.55 (br s, 2H), 7.32 (s, 1H), 7.59-7.67 (m, 3H), 11.30 (br s, 1H).

General Procedure for the Preparation of 2-halo N-thiazolyl Acetamide Derivatives To a stirred and cooled (0° C.) solution of appropriate thiazoleamine (1.0 equiv.) and pyridine (1.2 equiv.) in dichloromethane (5 volume) was added bromoacetyl bromide (1.2 eq.) over 5 min and the resulting mixture was allowed to warm to room temperature and then further stirred at room temperature for 2 h. The reaction mixture was diluted with dichloromethane (50 mL) and water (50 mL). The layers were separated. The aqueous layer was extracted with dichloromethane (2×50 mL) and the combined organic layers were washed with water (2×50 mL) followed by brine (50 mL), dried ($Na_2SO_4$) and filtered. The filtrate was concentrated under reduced pressure. The residue obtained after the evaporation of the solvent was purified by silica gel column chromatography using 5-10% ethyl acetate in petroleum ether to obtain the desired product as an off-white solid.

Structure information and characterization data for selected 2-bromo-N-thiazolyl acetamide intermediates are given in Table 1.

TABLE 1

Structure and $^1$H NMR data of selected 2-bromo-N-thiazolyl acetamides

| S No | Structure | Mol. Formula/ Mass (m/z) | $^1$H NMR (δ ppm, DMSO-$d_6$, 300 MHz) |
|---|---|---|---|
| 1. | (structure) | $C_{11}H_7BrF_2N_2OS$ 333.98 (M + H)$^+$ | 4.19 (s, 2H), 7.21 (t, J = 8.1 Hz, 1H), 7.37 (t, J = 9.3 Hz, 1H), 7.57 (s, 1H), 8.00-8.08 (m, 1H), 12.75 (br s, 1H) |
| 2. | (structure) | $C_{12}H_7BrF_4N_2OS$ 382.35 (M + H)$^+$ | 4.18 (s, 2H), 7.84 (d, J = 7.8 Hz, 1H), 7.91 (d, J = 8.7 Hz, 2H), 8.03 (s, 1H), 12.76 (br s, 1H). |
| 3. | (structure) | $C_{12}H_7BrF_4N_2OS$ 382.99 (M + H)$^+$ | 4.20 (s, 2H), 7.84 (d, J = 7.8 Hz, 1H), 7.95 (d, J = 8.7 Hz, 2H), 8.06 (s, 1H), 12.82 (br s, 1H). |
| 4. | (structure) | $C_{12}H_7BrClF_3N_2OS$ 401.00 (M + H)$^+$ | 4.18 (s, 2H), 7.88 (d, J = 7.2 Hz, 1H), 7.95 (d, J = 9.3 Hz, 1H), 8.18 (d, J = 7.8 Hz, 1H), 8.31 (s, 1H), 12.77 (br s, 1H). |
| 5. | (structure) | $C_{11}H_6BrCl_3N_2OS$ 399.05 (M + H)$^+$ | 4.18 (s, 2H), 7.74-7.80 (m, 3H), 12.78 (br s, 1H). |

TABLE 1-continued

Structure and ¹H NMR data of selected 2-bromo-N-thiazolyl acetamides

| S No | Structure | Mol. Formula/ Mass (m/z) | ¹H NMR (δ ppm, DMSO-$d_6$, 300 MHz) |
|---|---|---|---|
| 6. | 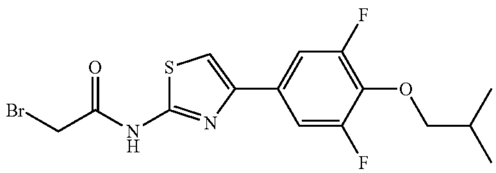 [SMILES: CC(C)COc1c(F)cc(-c2csc(NC(=O)CBr)n2)cc1F] | $C_{15}H_{15}BrF_2N_2O_2S$ 405.13 (M + H)⁺ | 0.98 (d, J = 6.3 Hz, 6H), 1.93-2.00 (m, 1H), 3.91 (d, J = 6.3 Hz, 2H), 4.18 (s, 2H), 7.64 (d, J = 9.3 Hz, 2H), 7.82 (s, 1H), 12.72 (br s, 1H) |
| 7. | 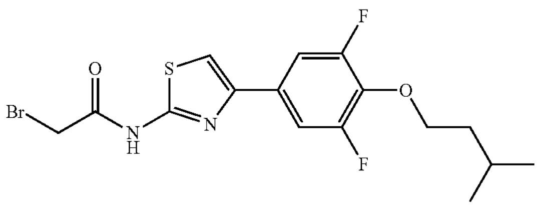 [SMILES: CC(C)CCOc1c(F)cc(-c2csc(NC(=O)CBr)n2)cc1F] | $C_{16}H_{17}BrF_2N_2O_2S$ 420.63 | DMSO-$d_6$: 0.92 (d, J = 6.9 Hz, 6H), 1.55-1.63 (m, 2H), 1.75-1.85 (m, 1H), 4.12-4.20 (m, 4H), 7.64 (d, J = 9.3 Hz, 2H), 7.82 (s, 1H), 12.74 (br s, 1H) |
| 8. | 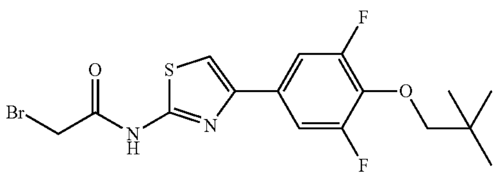 [SMILES: CC(C)(C)COc1c(F)cc(-c2csc(NC(=O)CBr)n2)cc1F] | $C_{16}H_{17}BrF_2N_2O_2S$ 419.11 (M + H)⁺ | 1.00 (s, 9H), 3.80 (s, 2H), 4.18 (s, 2H), 7.62 (s, 1H), 7.66 (m, 1H), 7.82 (s, 1H), 12.73 (br s, 1H). |
| 9. | 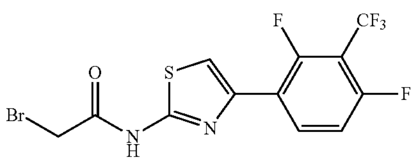 [SMILES: O=C(CBr)Nc1nc(-c2ccc(F)c(C(F)(F)F)c2F)cs1] | $C_{12}H_6BrF_5N_2OS$ 400.02 (M + H)⁺ | 4.20 (s, 2H), 7.47-7.55 (m, 1H), 7.71 (s, 1H), 8.28-8.34 (m, 1H), 12.79 (br s, 1H). |
| 10. | 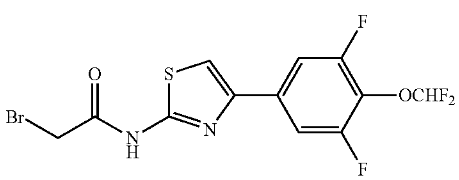 [SMILES: O=C(CBr)Nc1nc(-c2cc(F)c(OC(F)F)c(F)c2)cs1] | $C_{12}H_7BrF_4N_2O_2S$ 399.71 (M + H)⁺ | 4.18 (s, 2H), 7.25 (t, J = 71.7 Hz, 1H), 7.75 (d, J = 9.0 Hz, 2H), 7.93 (s, 1H), 12.73 (br s, 1H). |
| 11. | 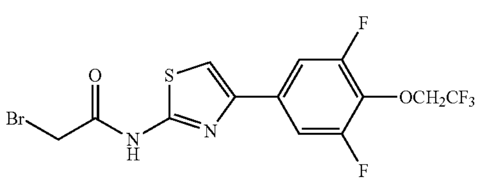 | $C_{13}H_8BrF_5N_2O_2S$ 430.18 (M + H)⁺ | 2.50-2.80 (m, 2H), 4.18 (s, 2H), 4.34 (t, J = 5.7 Hz, 2H), 7.63-7.70 (m, 2H), 7.85 (s, 1H), 12.74 (br s, 1H). |
| 12. | 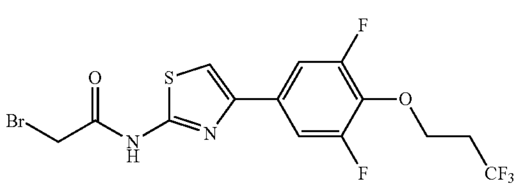 [SMILES: O=C(CBr)Nc1nc(-c2cc(F)c(OCCC(F)(F)F)c(F)c2)cs1] | $C_{14}H_{10}BrF_5N_2O_2S$ 445.01 (M + H)⁺ | 2.50-2.80 (m, 2H), 4.18 (s, 2H), 4.34 (t, J = 5.7 Hz, 2H), 7.63-7.70 (m, 2H), 7.85 (s, 1H), 12.74 (br s, 1H) |
| 13. | 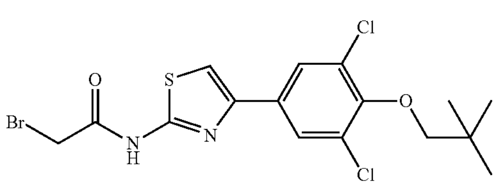 [SMILES: CC(C)(C)COc1c(Cl)cc(-c2csc(NC(=O)CBr)n2)cc1Cl] | $C_{16}H_{17}BrCl_2N_2O_2S$ 451.66 (M + H)⁺ | 1.07 (s, 9H), 3.67 (s, 2H), 4.18 (s, 2H), 7.90 (s, 1H), 7.99 (s, 2H), 12.72 (br s, 1H) |

TABLE 1-continued

Structure and $^1$H NMR data of selected 2-bromo-N-thiazolyl acetamides

| S No | Structure | Mol. Formula/ Mass (m/z) | $^1$H NMR (δ ppm, DMSO-d$_6$, 300 MHz) |
|---|---|---|---|
| 14. | 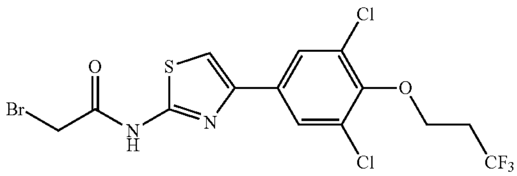 | $C_{14}H_{10}BrCl_2F_3N_2O_2S$ 477.54 (M + H)$^+$ | 2.79-2.89 (m, 2H), 4.16-4.22 (m, 4H), 7.90 (s, 1H), 7.99 (s, 2H), 12.70 (br s, 1H). |
| 15. | 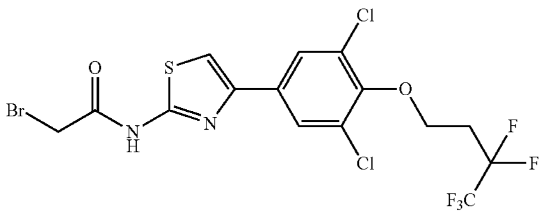 [SMILES: O=C(CBr)Nc1nc(-c2cc(Cl)c(OCCC(F)(F)C(F)(F)F)c(Cl)c2)cs1] | $C_{15}H_{10}BrCl_2F_5N_2O_2S$ 527.07 (M + H)$^+$ | 2.81 (t, J = 6.0 Hz, 2H), 4.19 (s, 2H), 4.28 (t, J = 6.0 Hz, 2H), 7.93 (s, 1H), 8.02 (s, 2H), 12.75 (br s, 1H). |
| 16. | 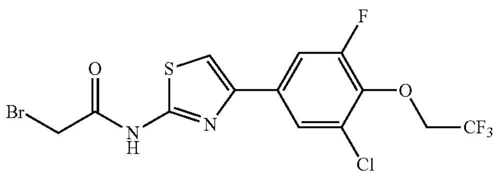 [SMILES: O=C(CBr)Nc1nc(-c2cc(F)c(OCC(F)(F)F)c(Cl)c2)cs1] | $C_{13}H_8BrClF_4N_2O_2S$ 446.93 (M + H)$^+$ | 4.19 (s, 2H), 4.80-4.90 (m, 2H), 7.71 (d, J = 9.3 Hz, 2H), 7.88 (s, 1H), 12.74 (br s, 1H) |
| 17. | 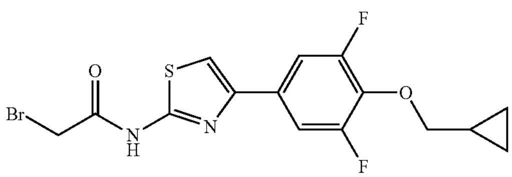 [SMILES: O=C(CBr)Nc1nc(-c2cc(F)c(OCC3CC3)c(F)c2)cs1] | $C_{15}H_{13}BrF_2N_2O_2S$ 403.24 (M + H)$^+$ | 0.23-0.30 (m, 2H), 0.50-0.56 (m, 2H), 1.17-1.22 (m, 1H), 3.97 (d, J = 6.9 Hz, 2H), 4.19 (s, 2H), 7.64 (d, J = 9.3 Hz, 2H), 7.82 (s, 1H), 12.72 (br s, 1H) |
| 18. | 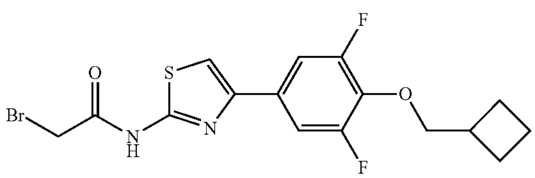 [SMILES: O=C(CBr)Nc1nc(-c2cc(F)c(OCC3CCC3)c(F)c2)cs1] | $C_{16}H_{15}BrF_2N_2O_2S$ 417.05 (M + H)$^+$ | 1.82-1.90 (m, 4H), 1.90-2.05 (m, 2H), 2.65-2.71 (m, 1H), 4.10 (d, J = 6.3 Hz, 2H), 4.19 (s, 2H), 7.64 (d, J = 9.3 Hz, 2H), 7.82 (s, 1H), 12.72 (br s, 1H) |
| 19. | 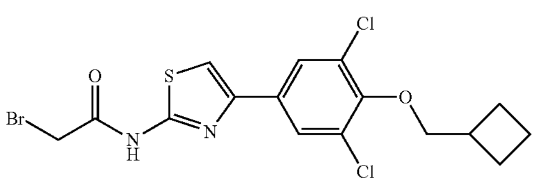 [SMILES: O=C(CBr)Nc1nc(-c2cc(Cl)c(OCC3CCC3)c(Cl)c2)cs1] | $C_{16}H_{15}BrCl_2N_2O_2S$ 449.05 (M + H)$^+$ | 1.85-1.95 (m, 4H), 2.04-2.10 (m, 2H), 2.72-2.79 (m, 1H), 4.00 (d, J = 6.3 Hz, 2H), 4.18 (s, 2H), 7.90 (s, 1H), 7.99 (s, 2H), 12.73 (br s, 1H). |
| 20. | 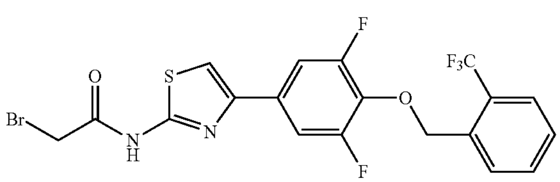 [SMILES: O=C(CBr)Nc1nc(-c2cc(F)c(OCc3ccccc3C(F)(F)F)c(F)c2)cs1] | $C_{19}H_{12}BrF_5N_2O_2S$ 504.92 (M − H) | 4.11 (s, 2H), 5.39 (s, 2H), 7.14 (s, 1H), 7.39-7.47 (m, 3H), 7.62 (t, J = 7.8 Hz, 1H), 7.68 (d, J = 7.8 Hz, 1H), 7.88 (d, J = 7.8 Hz, 1H), 9.62 (br s, 1H) |
| 21. | 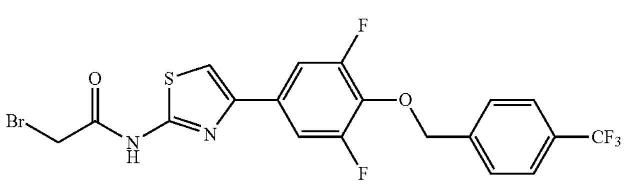 [SMILES: O=C(CBr)Nc1nc(-c2cc(F)c(OCc3ccc(C(F)(F)F)cc3)c(F)c2)cs1] | $C_{19}H_{12}BrF_5N_2O_2S$ 507.16 (M + H)$^+$ | 4.18 (s, 2H), 5.31 (s, 2H), 7.60-7.69 (m, 4H), 7.72-7.80 (m, 2H), 7.84 (s, 1H), 12.72 (br s, 1H). |

TABLE 1-continued

Structure and ¹H NMR data of selected 2-bromo-N-thiazolyl acetamides

| S No | Structure | Mol. Formula/ Mass (m/z) | ¹H NMR (δ ppm, DMSO-d₆, 300 MHz) |
|---|---|---|---|
| 22. | [structure: 2-bromo-N-[4-(3-bromo-4-(2,2,2-trifluoroethoxy)phenyl)thiazol-2-yl]acetamide] | $C_{13}H_9Br_2F_3N_2O_2S$<br>473.03 (M + H)⁺ | 4.18 (s, 2H), 4.86-4.96 (m, 2H), 7.31 (d, J = 8.7 Hz, 1H), 7.75 (s, 1H), 7.91 (d, J = 9.0 Hz, 1H), 8.16 (s, 1H), 12.71 (br s, 1H). |
| 23. | [structure: 2-bromo-N-[4-(3-chloro-5-fluoro-4-neopentyloxyphenyl)thiazol-2-yl]acetamide with OCH₂C(CH₃)₃] | $C_{16}H_{17}BrClFN_2O_2S$<br>435.17 (M + H)⁺ | 3.78 (s, 2H), 4.18 (s, 2H), 7.76 (s, 1H), 7.80 (s, 1H), 7.85 (s, 1H), 12.73 (br s, 1H). |
| 24. | [structure: 2-bromo-N-[4-(3-fluoro-4-neopentyloxyphenyl)thiazol-2-yl]acetamide] | $C_{16}H_{18}BrFN_2O_2S$<br>401.29 | DMSO-d₆: 1.02 (s, 9H), 3.74 (s, 2H), 4.18 (s, 2H), 7.22 (t, J = 8.7 Hz, 1H), 7.65-7.74 (m, 3H), 12.68 (br s, 1H) |
| 25. | [structure: 2-bromo-N-[4-(3-chloro-4-neopentyloxyphenyl)thiazol-2-yl]acetamide] | $C_{16}H_{18}BrClN_2O_2S$<br>417.75 | DMSO-d₆: 1.04 (s, 9H), 3.75 (s, 2H), 4.18 (s, 2H), 7.19 (d, J = 8.4 Hz, 1H), 7.67 (s, 1H), 7.81 (d, J = 8.7 Hz, 1H), 7.95 (s, 1H), 12.69 (br s, 1H) |
| 26. | [structure: 2-bromo-N-[4-(4-chlorophenyl)thiazol-2-yl]acetamide] | $C_{11}H_8BrClN_2OS$<br>331.62 | CDCl₃: 4.06 (s, 2H), 7.09 (s, 1H), 7.37 (d, J = 8.7 Hz, 2H), 7.62 (d, J = 8.4 Hz, 2H). |
| 27. | [structure: 2-bromo-N-[4-(3,5-dichloro-4-isobutoxyphenyl)thiazol-2-yl]acetamide] | $C_{15}H_{15}BrCl_2N_2O_2S$<br>438.17 | CDCl₃: 1.10 (d, J = 6.3 Hz, 6H), 2.10-2.24 (m, 1H), 3.81 (d, J = 6.3 Hz, 2H), 4.11 (s, 2H), 7.16 (s, 1H), 7.76 (s, 2H), 9.56 (br s, 1H) |
| 28 | [structure: 2-bromo-N-[5-(4-bromophenyl)isoxazol-3-yl]acetamide] | $C_{11}H_8Br_2N_2O_2$<br>360.00 | DMSO-d₆: 4.11 (s, 2H), 7.42 (s, 1H), 7.73 (d, J = 8.1 Hz, 2H), 7.86 (d, J = 8.1 Hz, 2H), 11.56 (br s, 1H) |

General Procedure for the Preparation of 2-amino-4-aryl Thiazoles:

Method 1

A solution of acetophenone derivative (1.0 eq) in glacial acetic acid (5 vol) was added liquid bromine (1.0 eq) at 0° C. and reaction mixture was stirred at room temperature for 2 h. The reaction mixture was diluted with water and extracted with ethyl acetate, washed with brine and dried over Na₂SO₄. The crude product obtained upon concentration was dissolved in dry THF (10 vol) and thiourea (2.0 eq) was added and refluxed for overnight. The reaction mixture was diluted with ethyl acetate, washed with sodium thiosulfate solution and organic layer was treated with 1N HCl to result salt formation of the amine. The precipitated salt was collected by filtration. The salt was then treated with saturated solution of NaHCO₃ to re-generate the amine. The mixture was extracted with dichloromethane (2×50 ml) and the combined organic extracts were washed with water and brine. The solvent was evaporated under reduced pressure to afford the 2-amino-4-aryl-thiazole derivative.

Method 2

A solution of acetophenone derivative (1.0 equiv.), thiourea (2.0 equiv.) and iodine (1.0 equiv.) in dry ethanol (5 vol) was refluxed for 24 h. The reaction mixture was diluted with ethyl acetate and the layers were separated. The organic layer was washed with sodium thiosulfate solution to remove iodine. The ethyl acetate solution was treated with 1N HCl and precipitated salt collected by filtration. The free amine was re-generated as described in Method 1 given above.

All the 2-amino-4-aryl-thiazole derivatives were prepared by either Method 1 or Method 2 starting from appropriate aryl alkyl ketones. Structure information and characterization data for selected intermediates are given in Table 2.

TABLE 2

Structural details and $^1$H NMR data of selected 2-aminothiazole intermediates

| S No | Structure | Mol. Formula (Mol. Wt.) | $^1$H NMR (δ ppm, 300 MHz) |
|---|---|---|---|
| 1. | 2-amino-4-(4-bromophenyl)thiazole | C$_9$H$_7$BrN$_2$S (255.14) | DMSO-d$_6$: 7.61 (d, J = 8.1, 2H); 7.46 (d, J = 7.8, 2H); 6.70 (s, 1H); 4.99 (br. s, 2H). |
| 2. | 2-amino-4-(4-chlorophenyl)thiazole | C$_9$H$_7$ClN$_2$S (210.68) | DMSO-d$_6$: 7.78 (d, J = 8.4, 2H); 7.39 (d, J = 7.8, 2H); 7.07 (br. s, 2H); 7.05 (s, 1H). |
| 3. | 2-amino-4-(4-trifluoromethylphenyl)thiazole | C$_{10}$H$_7$F$_3$N$_2$S (244.24) | DMSO-d$_6$: 7.97 (d, J = 7.8, 2H); 7.69 (d, J = 8.1, 2H); 7.24 (s, 1H); 7.16 (br. s, 2H). |
| 4. | 2-amino-4-(3-trifluoromethylphenyl)thiazole | C$_{10}$H$_7$F$_3$N$_2$S (244.24) | CDCl$_3$: 8.12-8.06 (m, 1H); 7.91 (d, J = 6.9, 1H); 7.50-7.42 (m, 2H); 6.79 (s, 1H); 5.02 (br. s, 2H). |
| 5. | 2-amino-4-(3-trifluoromethoxyphenyl)thiazole | C$_{10}$H$_6$F$_4$N$_2$S 262.24 | CDCl$_3$: 7.68-7.61 (m, 2H); 7.36 (t, J = 7.8, 1H); 7.10 (d, J = 7.8, 1H), 6.75 (s, 1H); 5.08 (br s, 2H). |
| 6. | 2-amino-4-(4-isobutylphenyl)thiazole | C$_{13}$H$_{16}$N$_2$S (232.25) | DMSO-d$_6$: 7.68 (d, J = 7.8, 2H); 7.13 (d, J = 8.1, 2H); 7.03 (br. s, 2H); 6.92 (s, 1H); 2.43 (d, J = 6.9, 2H); 1.86-1.76 (m, 1H); 0.86 (d, J = 6.6, 6H) |
| 7. | 2-amino-4-(2,4-difluorophenyl)thiazole | C$_9$H$_6$F$_2$N$_2$S (212.22) | CDCl$_3$: 8.04-7.95 (m, 1H); 6.93-6.80 (m, 3H); 5.04 (br. s, 2H). |
| 8. | 2-amino-4-(3-fluoro-4-trifluoromethylphenyl)thiazole | C$_{10}$H$_6$F$_4$N$_2$S 262.23 | DMSO-d$_6$: 7.87-7.74 (m, 3H); 7.40 (s, 1H); 7.22 (br. s, 2H). |
| 9. | 2-amino-4-(4-fluoro-3-trifluoromethoxyphenyl)thiazole | C$_{10}$H$_6$F$_4$N$_2$OS (278.23) | DMSO-d$_6$: 7.92-7.85 (m, 2H); 7.50 (t, J = 8.7, 1H); 7.18 (br. s, 3H). |
| 10. | 2-amino-4-(3-fluoro-4-trifluoromethoxyphenyl)thiazole | C$_{10}$H$_6$F$_4$N$_2$OS (278.23) | DMSO-d$_6$: 7.87-7.80 (m, 1H); 7.73 (d, J = 8.7, 1H); 7.55 (d, J = 8.1, 1H); 7.24 (s, 1H); 7.18 (br. s, 2H). |
| 11. | 2-amino-4-(3-fluoro-4-(2,2,2-trifluoroethoxy)phenyl)thiazole | C$_{11}$H$_8$F$_4$N$_2$OS (292.25) | CDCl$_3$: 7.57-7.46 (m, 2H), 7.02 (t, J = 8.4, 1H); 6.66 (s, 1H); 5.08 (br. s, 2H); 4.43 (q, J = 8.4, 2H) |

TABLE 2-continued

Structural details and ¹H NMR data of selected 2-aminothiazole intermediates

| S No | Structure | Mol. Formula (Mol. Wt.) | ¹H NMR (δ ppm, 300 MHz) |
|---|---|---|---|
| 12. | (2-aminothiazole with 4-F, 3-CF₃ phenyl) | $C_{10}H_6F_4N_2S$ (262.23) | DMSO-$d_6$: 8.14 (d, J = 6.6, 2H); 7.52 (t, J = 8.7, 1H); 7.24 (s, 1H); 7.20 (br. s, 2H). |
| 13. | (2-aminothiazole with 2,4-diF, 3-CF₃ phenyl) | $C_{10}H_5F_5N_2S$ (280.22) | DMSO-$d_6$: 8.35-8.21 (m, 1H); 7.48-7.35 (m, 1H); 7.21 (br. s, 2H); 7.05 (s, 1H). |
| 14 | (2-aminothiazole with 2-F, 5-CF₃ phenyl) | $C_{10}H_6F_4N_2S$ 262.23 | CDCl₃: 8.36-8.29 (m, 1H); 7.73-7.65 (m, 1H); 7.58-7.50 (m, 1H); 7.26 (br. s, 2H); 7.13 (s, 1H) |
| 15 | (2-aminothiazole with 3-F, 4-OCHF₂ phenyl) | $C_{10}H_7F_3N_2OS$ 260.24 | DMSO-$d_6$: 7.75-7.62 (m, 2H); 7.33 (t, J = 8.1, 1H); 7.23 (t, J = 73.2, 1H); 7.12 (br. s, 3H) |
| 16 | (2-aminothiazole with 3,5-diF phenyl) | $C_9H_6F_2N_2S$ 212.22 | CDCl₃: 7.30-7.20 (m, 2H); 6.80-6.74 (m, 1H); 6.68-6.60 (m, 1H), 5.06 (br s, 2H) |
| 17 | (2-aminothiazole with 2-F, 3-CF₃ phenyl) | $C_{10}H_6F_4N_2S$ 262.23 | CDCl₃: 8.28-8.21 (m, 1H); 7.51 (t, J = 6.9, 1H); 7.27 (t, J = 7.5, 1H); 7.10 (s, 1H), 5.04 (br s, 2H) |
| 18 | (2-aminothiazole with 2,3-diF, 4-CF₃ phenyl) | $C_{10}H_5F_5N_2S$ 280.22 | CDCl₃: 7.94-7.82 (m, 1H); 7.42-7.32 (m, 1H); 7.18-7.10 (m, 1H); 5.09 (br s, 2H) |
| 19 | (2-aminothiazole with 3,5-diF, 4-OCH₂CF₃ phenyl) | $C_{11}H_7F_5N_2OS$ 310.24 | DMSO-$d_6$: 7.59 (s, 1H); 7.55 (s, 1H); 7.21 (s, 1H); 7.16 (br. s, 2H); 4.82 (q, J = 9.0, 2H). |
| 20 | (2-aminothiazole with 3,5-diF, 4-OCHF₂ phenyl) | $C_{10}H_6F_4N_2OS$ 278.23 | DMSO-$d_6$: 7.65 (d, J = 9.0, 2H); 7.48 (s, 1H); 7.24 (t, J = 72.3, 1H); 7.20 (br. s, 2H). |

TABLE 2-continued

Structural details and $^1$H NMR data of selected 2-aminothiazole intermediates

| S No | Structure | Mol. Formula (Mol. Wt.) | $^1$H NMR (δ ppm, 300 MHz) |
|---|---|---|---|
| 21 | (thiazole-phenyl with CF₃, F) | $C_{10}H_6F_4N_2OS$ 262.23 | DMSO-$d_6$: 7.97-7.87 (m, 1H); 7.62-7.52 (m, 1H); 7.41 (s, 1H); 7.23 (br. s, 2H). |
| 22 | (thiazole-phenyl with F, OCH₂C(CH₃)₃, F) | $C_{14}H_{16}F_2N_2OS$ 298.35 | DMSO-$d_6$: 1.00 (s, 9H), 3.76 (s, 2H), 7.12-7.18 (m, 1H + 2H), 7.48-7.58 (m, 2H) |
| 23 | (thiazole-phenyl with CF₃, F) | $C_{10}H_6F_4N_2S$ 262.23 | CDCl₃: 5.00 (br s, 2H); 7.16 (s, 1H); 7.37 (d, J = 11.7, 1H); 7.44 (d, J = 8.4, 1H); 8.18 (t, J = 7.8, 1H). |
| 24 | (thiazole-phenyl with F, F) | $C_9H_6F_2N_2S$ (212.22) | CDCl₃: 7.60-7.53 (m, 1H); 7.48-7.43 (m, 1H); 7.18-7.07 (m, 1H); 6.66 (s, 1H); 4.98 (br. s, 2H). |
| 25 | (thiazole-phenyl with F, O-neopentyl, F) | $C_{14}H_{16}F_2N_2OS$ 298.35 | DMSO-$d_6$: 1.00 (s, 9H), 3.76 (s, 2H), 7.12-7.18 (m, 1H + 2H), 7.48-7.58 (m, 2H) |

5-(4-Bromophenyl)isoxazol-3-amine used for the preparation of Examples 33, 65 and 84 is purchased from Aldrich. 5-(Trifluoromethoxy)-1,3-benzothiazol-2-amine used for the preparation of Example 66 is also purchased from Aldrich.

For further illustration of methods of preparing the compounds of the present invention, the following examples are disclosed below.

EXAMPLES

General Procedure for the Preparation of Examples

Method A:

To a stirred mixture of pyrrolo[3,2-d]pyrimidinedione (Intermediates 1-6, 1.0 equiv.) or pyrazolo[4,3-d]pyrimidinedione (Intermediates 9-10, 1.0 equiv.) and NaH (1.5 equiv.) in dry DMF (10 ml/g) was added 2-bromo-N-phenyl-1,3-thiazol-2-yl acetamide (1.1 equiv.) at 0° C., the reaction mixture was warmed to room temperature and stirred for 30 min. The reaction mixture was heated to 80° C. for overnight. After this time, the reaction mixture was concentrated under reduced pressure and the residue purified by silica gel column chromatography by using 2% methanol in chloroform to afford the product.

Method B:

To a stirred solution of (1,3,7-Trimethyl-2,4-dioxo-2,3,4,7-tetrahydro-1H-pyrrolo[2,3-d]pyrimidin-5-yl)acetic acid (Intermediate 7, 1.0 equiv.) or 2,5,7-Trimethyl-4,6-dioxo-4,5,6,7-tetrahydro-2H-pyrazolo[3,4-d]pyrimidin-3-yl)acetic acid (Intermediate 8, 1.0 equiv.) in 1,2-dichloroethane was added EDCI (1.2 equiv.), HOBt (0.3 equiv.) and 4-dimethylaminopyridine (0.1 equiv.) and the mixture was stirred at room temperature for 10-15 min. An appropriate amine (1.0 equiv.) was then added and mixture was stirred at the same temperature for 48 h. The solvent was evaporated under reduced pressure and the residue obtained was diluted with methanol and stirred at room temperature for 30 min. The solid separated out was collected by filtration. The solid product was further purified by recrystallization from isopropanol or methanol to give the desired products.

Example 1

N-[4-(2,4-Difluorophenyl)-1,3-thiazol-2-yl]-2-(1,3-dimethyl-2,4-dioxo-1,2,3,4-tetrahydro-5H-pyrrolo[3,2-d]pyrimidin-5-yl)acetamide

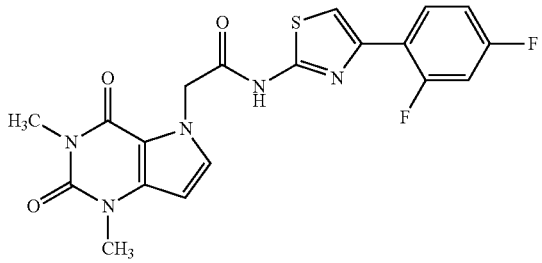 [SMILES: Cn1c(=O)c2c(ccn2CC(=O)Nc2nc(-c3ccc(F)cc3F)cs2)n(C)c1=O]

The title compound was prepared according to the general procedure (Method A) by coupling Intermediate 1 (50 mg, 0.279 mmol) with 2-bromo-N-[4-(2,4-difluorophenyl)-1,3-thiazol-2-yl]acetamide (111 mg, 0.330 mmol) in the presence of NaH (16 mg, 0.666 mmol) in dry DMF (5.0 mL) to give 60 mg of the product as a white solid; $^1$H NMR (δ ppm, DMSO-$d_6$, 300 MHz) 3.17 (s, 3H), 3.40 (s, 3H), 5.32 (s, 2H), 6.23 (s, 1H), 7.21-7.27 (m, 1H), 7.36-7.42 (m, 2H), 7.52 (s, 1H), 8.03-8.10 (m, 1H), 12.70 (br s, 1H); APCI-MS (m/z) 432.20 (M+H)$^+$.

Example 2

2-(1,3-Dimethyl-2,4-dioxo-1,2,3,4-tetrahydro-5H-pyrrolo[3,2-d]pyrimidin-5-yl)-N-{4-[4-fluoro-3-(trifluoromethyl)phenyl]-1,3-thiazol-2-yl}acetamide

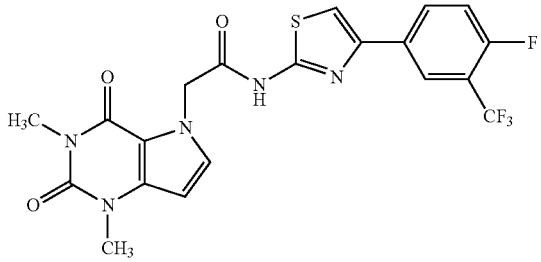 [SMILES: Cn1c(=O)c2c(ccn2CC(=O)Nc2nc(-c3ccc(F)c(C(F)(F)F)c3)cs2)n(C)c1=O]

The title compound was prepared according to the general procedure (Method A) by coupling Intermediate 1 (50 mg, 0.279 mmol) with 2-bromo-N-[4-(4-fluoro-3-trifluoromethylphenyl)-1,3-thiazol-2-yl]acetamide (128 mg, 0.334 mmol) in the presence of NaH (16 mg, 0.666 mmol) in dry DMF (5.0 mL) to give 75 mg of the product as an off-white solid; $^1$H NMR (δ ppm, DMSO-$d_6$, 300 MHz) 3.17 (s, 3H), 3.40 (s, 3H), 5.32 (s, 2H), 6.23 (s, 1H), 7.36 (s, 1H), 7.58-7.66 (m, 1H), 7.88 (s, 1H), 8.24-8.32 (m, 2H), 12.74 (br s, 1H); APCI-MS (m/z) 480.16 (M−H).

Example 3

2-(1,3-Dimethyl-2,4-dioxo-1,2,3,4-tetrahydro-5H-pyrrolo[3,2-d]pyrimidin-5-yl)-N-{4-[3-fluoro-4-(trifluoromethyl)phenyl]-1,3-thiazol-2-yl}acetamide

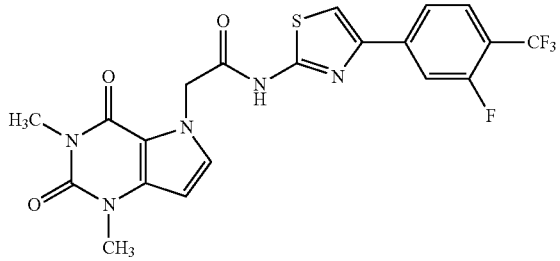 [SMILES: Cn1c(=O)c2c(ccn2CC(=O)Nc2nc(-c3ccc(C(F)(F)F)c(F)c3)cs2)n(C)c1=O]

The title compound was prepared according to the general procedure (Method A) by coupling Intermediate 1 (50 mg, 0.279 mmol) with 2-bromo-N-[4-(3-fluoro-4-trifluoromethylphenyl)-1,3-thiazol-2-yl]acetamide (128 mg, 0.334 mmol) in the presence of NaH (10 mg, 0.418 mmol) in dry DMF (5.0 mL) to give 75 mg of the product as a white solid; $^1$H NMR (δ ppm, DMSO-$d_6$, 300 MHz) 3.17 (s, 3H), 3.40 (s, 3H), 5.33 (s, 2H), 6.24 (s, 1H), 7.36 (s, 1H), 7.86 (d, J=7.8 Hz, 1H), 7.90-8.01 (m, 3H), 12.77 (br s, 1H); APCI-MS (m/z) 482.07 (M+H)$^+$.

Example 4

2-(1,3-Dimethyl-2,4-dioxo-1,2,3,4-tetrahydro-5H-pyrrolo[3,2-d]pyrimidin-5-yl)-N-{4-[4-chloro-3-(trifluoromethyl)phenyl]-1,3-thiazol-2-yl}acetamide

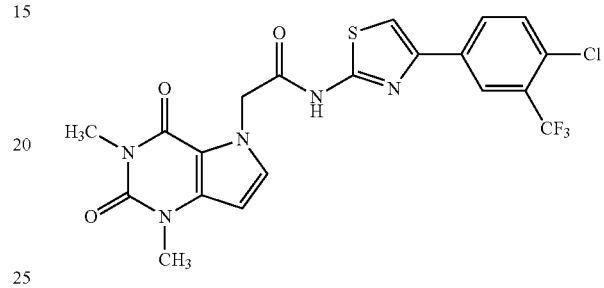

The title compound was prepared according to the general procedure (Method A) by coupling Intermediate 1 (30 mg, 0.167 mmol) with 2-bromo-N-[4-(4-chloro-3-trifluoromethylphenyl)-1,3-thiazol-2-yl]acetamide (80 mg, 0.200 mmol) in the presence of NaH (10 mg, 0.416 mmol) in dry DMF (5.0 mL) to give 38 mg of the product as an off-white solid; $^1$H NMR (δ ppm, CDCl$_3$, 300 MHz) 3.17 (s, 3H), 3.39 (s, 3H), 5.32 (s, 2H), 6.22 (s, 1H), 7.35 (s, 1H), 7.80 (d, J=8.4 Hz, 1H), 7.94 (s, 2H), 8.20 (d, J=8.4 Hz, 1H), 8.34 (s, 1H), 12.74 (br s, 1H). APCI-MS (m/z) 498.14 (M+H)$^+$.

Example 5

2-(1,3-Dimethyl-2,4-dioxo-1,2,3,4-tetrahydro-5H-pyrrolo[3,2-d]pyrimidin-5-yl)-N-[4-(2,3,4-trichlorophenyl)-1,3-thiazol-2-yl]acetamide

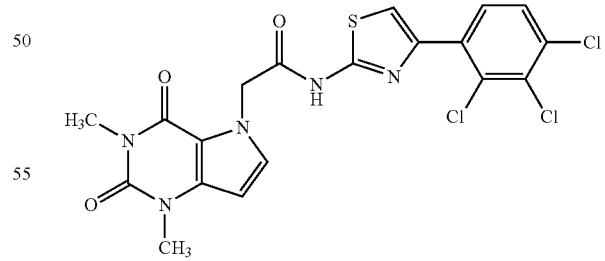

The title compound was prepared according to the general procedure (Method A) by coupling Intermediate 1 (50 mg, 0.279 mmol) with 2-bromo-N-[4-(2,3,4-trichlorophenyl)-1,3-thiazol-2-yl]acetamide (134 mg, 0.334 mmol) in the presence of NaH (10 mg, 0.416 mmol) in dry DMF (5.0 mL) to give 37 mg of the product as an off-white solid; $^1$H NMR (δ ppm, DMSO-$d_6$, 300 MHz) 3.17 (s, 3H), 3.40 (s, 3H), 5.32 (s, 2H), 6.23 (s, 1H), 7.35 (s, 1H), 7.70 (s, 1H), 7.77 (s, 2H), 12.74 (br s, 1H). APCI-MS (m/z) 498.14 (M+H)+.

Example 6

2-(1,3-Dimethyl-2,4-dioxo-1,2,3,4-tetrahydro-5H-pyrrolo[3,2-d]pyrimidin-5-yl)-N-{4-[4-(2-methylpropoxy)-3,5-difluorophenyl]-1,3-thiazol-2-yl}acetamide

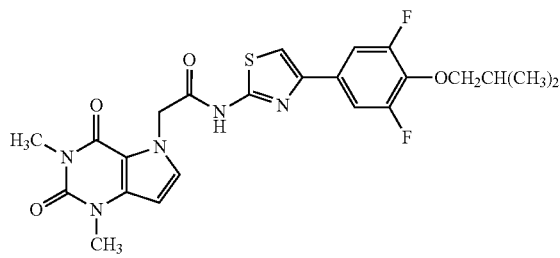

The title compound was prepared according to the general procedure (Method A) by coupling Intermediate 1 (50 mg, 0.279 mmol) with 2-bromo-N-{4-[4-(2-methylpropoxy)-3,5-difluorophenyl]-1,3-thiazol-2-yl}acetamide (135 mg, 0.334 mmol) in the presence of NaH (10 mg, 0.416 mmol) in dry DMF (5.0 mL) to give 45 mg of the product as an off-white solid; $^1$H NMR (δ ppm, 300 MHz, DMSO-$d_6$) 0.98 (d, J=6.9 Hz, 6H), 1.96-2.04 (m, 1H), 3.17 (s, 3H), 3.33 (s, 3H), 3.91 (d, J=6.3 Hz, 2H), 5.32 (s, 2H), 6.22 (s, 1H), 7.35 (s, 1H), 7.65 (d, J=9.0 Hz, 2H), 7.77 (s, 1H), 12.68 (br s, 1H); APCI-MS (m/z) 504.11 (M+H)+.

Example 7

N-{4-[3,5-Difluoro-4-(3-methylbutoxy)phenyl]-1,3-thiazol-2-yl}-2-(1,3-dimethyl-2,4-dioxo-1,2,3,4-tetrahydro-5H-pyrrolo[3,2-d]pyrimidin-5-yl)acetamide

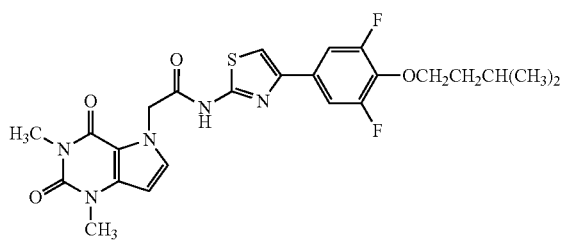

The title compound was prepared according to the general procedure (Method A) by coupling Intermediate 1 (50 mg, 0.279 mmol) with 2-bromo-N-{-4-[3,5-difluoro-4-(3-methylbutoxy)phenyl]-1,3-thiazol-2-yl}acetamide (140 mg, 0.334 mmol) in the presence of NaH (16 mg, 0.666 mmol) in dry DMF (5.0 mL) to give 75 mg of the product as an off-white solid; $^1$H NMR (δ ppm, DMSO-$d_6$, 300 MHz) 0.92 (d, J=6.6 Hz, 6H), 1.60 (d, J=6.3 Hz, 2H), 1.75-1.85 (m, 1H), 3.17 (s, 3H), 3.39 (s, 3H), 4.15 (d, J=6.3 Hz, 2H), 5.32 (s, 2H), 6.22 (s, 1H), 7.35 (s, 1H), 7.63 (s, 1H), 7.66 (s, 1H), 7.77 (s, 1H), 12.68 (br s, 1H); ESI-MS (m/z) 516.41 [M–H].

Example 8

N-{[4-(2,2-Dimethylpropoxy)-3,5-difluorophenyl]-1,3-thiazol-2-yl}-2-(1,3-dimethyl-2,4-dioxo-1,2,3,4-tetrahydro-5H-pyrrolo[3,2-d]pyrimidin-5-yl)acetamide

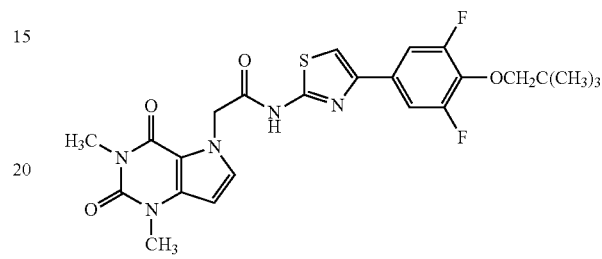

The title compound was prepared according to the general procedure (Method A) by coupling Intermediate 1 (25 mg, 0.139 mmol) with 2-bromo-N-{4-[4-(2,2-dimethylpropoxy)-3,5-difluorophenyl]-1,3-thiazol-2-yl}acetamide (70 mg, 0.167 mmol) in the presence of NaH (8 mg, 0.333 mmol) in dry DMF (5.0 mL) to give 29 mg of the product as an off-white solid; $^1$H NMR (δ ppm, DMSO-$d_6$, 300 MHz) 1.01 (s, 9H), 3.17 (s, 3H), 3.39 (s, 3H), 3.81 (s, 2H), 5.32 (s, 2H), 6.23 (s, 1H), 7.35 (s, 1H), 7.63 (s, 1H), 7.67 (s, 1H), 7.77 (s, 1H), 12.68 (br s, 1H); APCI-MS (m/z) 518.10 [M+H]+.

Example 9

2-(1,3-Dimethyl-2,4-dioxo-1,2,3,4-tetrahydro-5H-pyrrolo[3,2-d]pyrimidin-5-yl)-N-{4-[2,4-difluorophenyl-3-trifluoromethyl]-1,3-thiazol-2-yl}acetamide

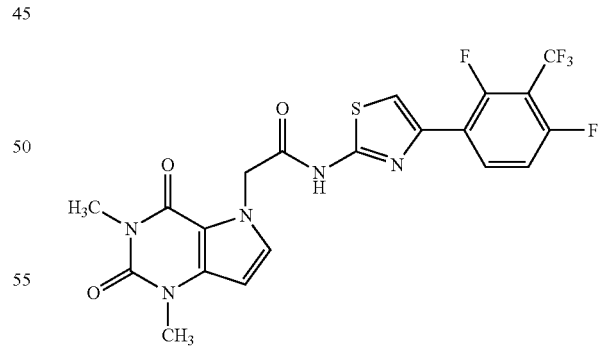

The title compound was prepared according to the general procedure (Method A) by coupling Intermediate 1 (50 mg, 0.279 mmol) with 2-bromo-N-{-4-[2,4-difluorophenyl-3-trifluoromethyl]-1,3-thiazol-2-yl}acetamide (134 mg, 0.334 mmol) in the presence of NaH (16 mg, 0.666 mmol) in dry DMF (5.0 mL) to give 60 mg of the product as an off-white solid; $^1$H NMR (δ ppm, 300 MHz, DMSO-$d_6$) 3.17 (s, 3H), 3.40 (s, 3H), 5.33 (s, 2H), 6.23 (s, 1H), 7.35 (s, 1H), 7.48-7.58

(m, 1H), 7.66 (s, 1H), 8.28-8.38 (m, 1H), 12.75 (br s, 1H); APCI-MS (m/z) 500.02 (M+H)+.

Example 10

N-{4-[4-(Difluoromethoxy)-3,5-difluorophenyl]-1,3-thiazol-2-yl}-2-(1,3-dimethyl-2,4-dioxo-1,2,3,4-tetrahydro-5H-pyrrolo[3,2-d]pyrimidin-5-yl)acetamide

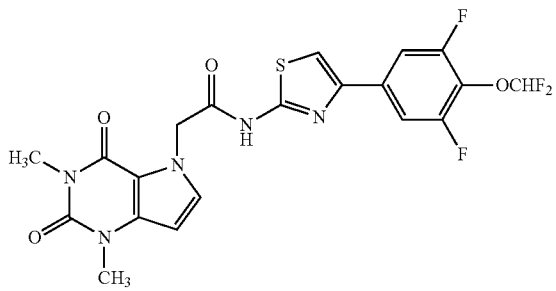 [SMILES: Cn1c(=O)c2c(ccn2CC(=O)Nc2nc(-c3cc(F)c(OC(F)F)c(F)c3)cs2)n(C)c1=O]

The title compound was prepared according to the general procedure (Method A) by coupling Intermediate 1 (45 mg, 0.251 mmol) with 2-bromo-N-{4-[4-(difluoromethoxy)-3,5-difluorophenyl]-1,3-thiazol-2-yl}acetamide (125 mg, 0.313 mmol) in the presence of NaH (16 mg, 0.666 mmol) in dry DMF (5.0 mL) to give 20 mg of the product as an off-white solid; $^1$H NMR (δ ppm, DMSO-$d_6$, 300 MHz) 3.17 (s, 3H), 3.39 (s, 3H), 5.32 (s, 2H), 6.23 (s, 1H), 7.28 (t, J=72.3 Hz, 1H), 7.35 (s, 1H), 7.79 (d, J=9.6 Hz, 2H), 7.90 (s, 1H), 12.73 (br s, 1H); ESI-MS (m/z) 498.08 (M+H)+.

Example 11

N-{-4-[3,5-Difluoro-4-(2,2,2-trifluoroethoxy)phenyl]-1,3-thiazol-2-yl}-2-(1,3-dimethyl-2,4-dioxo-1,2,3,4-tetrahydro-5H-pyrrolo[3,2-d]pyrimidin-5-yl)acetamide

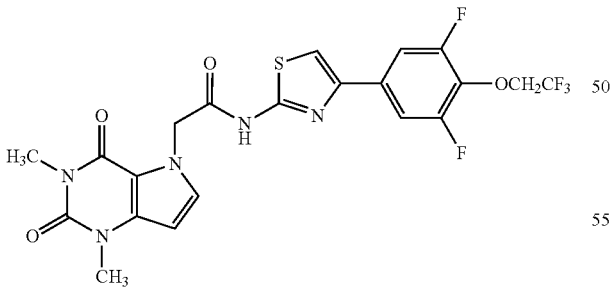

The title compound was prepared according to the general procedure (Method A) by coupling Intermediate 1 (29 mg, 0.166 mmol) with 2-bromo-N-{-4-[3,5-difluoro-4-(2,2,2-trifluoroethoxy)phenyl]-1,3-thiazol-2-yl}acetamide (60 mg, 0.139 mmol) in the presence of NaH (5.0 mg, 0.208 mmol) in dry DMF (5.0 mL) to give 20 mg of the product as a white solid; $^1$H NMR (δ ppm, DMSO-$d_6$, 300 MHz) 3.17 (s, 3H), 3.39 (s, 3H), 4.86 (q, J=8.7 Hz, 2H), 5.32 (s, 2H), 6.23 (s, 1H), 7.35 (s, 1H), 7.69 (s, 1H), 7.72 (s, 1H), 7.83 (s, 1H), 12.70 (br s, 1H); ESI-MS (m/z) 530.11 (M+H)+.

Example 12

N-{-4-[3,5-Difluoro-4-(3,3,3-trifluoropropoxy)phenyl]-1,3-thiazol-2-yl}-2-(1,3-dimethyl-2,4-dioxo-1,2,3,4-tetrahydro-5H-pyrrolo[3,2-d]pyrimidin-5-yl)acetamide

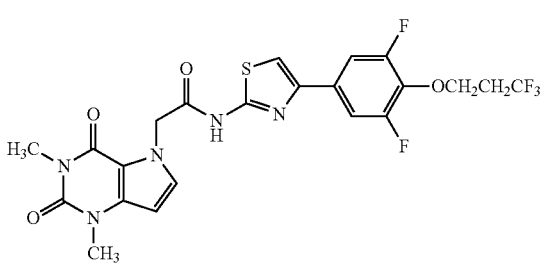

The title compound was prepared according to the general procedure (Method A) by coupling Intermediate 1 (30 mg, 0.167 mmol) with 2-bromo-N-{4-[3,5-difluoro-4-(3,3,3-trifluoropropoxy)phenyl]-1,3-thiazol-2-yl}acetamide (89 mg, 0.200 mmol) in the presence of NaH (10 mg, 0.416 mmol) in dry DMF (5.0 mL) to give 18 mg of the product as a white solid; $^1$H NMR (δ ppm, DMSO-$d_6$, 300 MHz): 2.73-2.84 (m, 2H), 3.17 (s, 3H), 3.39 (s, 3H), 4.32-4.38 (m, 2H), 5.32 (s, 2H), 6.23 (s, 1H), 7.35 (s, 1H), 7.66 (s, 1H), 7.69 (s, 1H), 7.80 (s, 1H), 12.70 (br s, 1H); APCI-MS (m/z): 542.20 [M−H].

Example 13

N-{4-[3,5-Dichloro-4-(2,2-dimethylpropoxy)phenyl]-1,3-thiazol-2-yl}-2-(1,3-dimethyl-2,4-dioxo-1,2,3,4-tetrahydro-5H-pyrrolo[3,2-d]pyrimidin-5-yl)acetamide

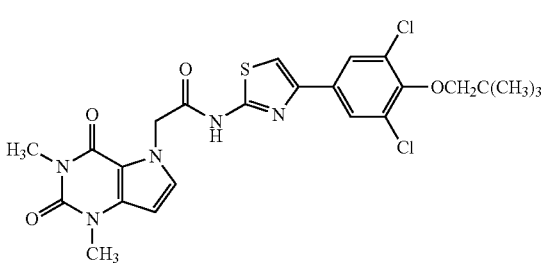

The title compound was prepared according to the general procedure (Method A) by coupling Intermediate 1 (50 mg, 0.110 mmol) with 2-bromo-N-{4-[3,5-dichloro-4-(2,2-dimethylpropoxy)phenyl]-1,3-thiazol-2-yl}acetamide (23 mg, 0.128 mmol) in the presence of NaH (7 mg, 0.291 mmol) in dry DMF (5.0 mL) to give 30 mg of the product as an off-white solid; $^1$H NMR (δ ppm, DMSO-$d_6$, 300 MHz) 1.08 (s, 9H), 3.17 (s, 3H), 3.39 (s, 3H), 3.67 (s, 2H), 5.32 (s, 2H), 6.22

(s, 2H), 7.35 (s, 1H), 7.85 (s, 1H), 8.00 (s, 2H), 12.68 (br s, 1H); APCI-MS (m/z) 550.20 [M+H]⁺.

Example 14

N-{4-[3,5-Dichloro-4-(3,3,3-trifluoropropoxy)phenyl]-1,3-thiazol-2-yl}-2-(1,3-dimethyl-2,4-dioxo-1,2,3,4-tetrahydro-5H-pyrrolo[3,2-d]pyrimidin-5-yl)acetamide

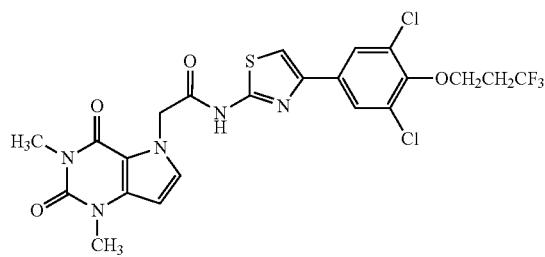

The title compound was prepared according to the general procedure (Method A) by coupling Intermediate 1 (50 mg, 0.279 mmol) with 2-bromo-N-{4-[3,5-dichloro-4-(3,3,3-trifluoropropoxy)phenyl]-1,3-thiazol-2-yl}acetamide (160 mg, 0.334 mmol) in the presence of NaH (16 mg, 0.666 mmol) in dry DMF (5.0 mL) to give 30 mg of the product as a white solid; ¹H NMR (δ ppm, DMSO-d₆, 300 MHz) 2.85-2.92 (m, 2H), 3.17 (s, 3H), 3.39 (s, 3H), 4.18-4.23 (m, 2H), 5.32 (s, 2H), 6.23 (s, 1H), 7.35 (s, 1H), 7.88 (s, 1H), 8.00-8.08 (m, 2H), 12.71 (br s, 1H); APCI-MS (m/z) 576.23 (M+H)⁺.

Example 15

N-{4-[3,5-Dichloro-4-(3,3,4,4,4-pentafluorobutoxy)phenyl]-1,3-thiazol-2-yl}-2-(1,3-dimethyl-2,4-dioxo-1,2,3,4-tetrahydro-5H-pyrrolo[3,2-d]pyrimidin-5-yl)acetamide

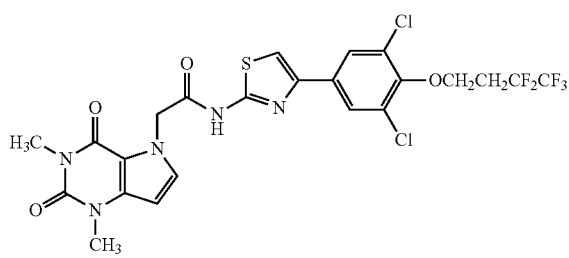

The title compound was prepared according to the general procedure (Method A) by coupling Intermediate 1 (50 mg, 0.279 mmol) with 2-bromo-N-{4-[3,5-dichloro-4-(3,3,4,4,4-pentafluorobutoxy)phenyl]-1,3-thiazol-2-yl}acetamide (176 mg, 0.332 mmol) in the presence of NaH (16 mg, 0.666 mmol) in dry DMF (5.0 mL) to give 58 mg of the product as an off-white solid; ¹H NMR (δ ppm, DMSO-d₆, 300 MHz) 2.80-2.86 (m, 2H), 3.17 (s, 3H), 3.39 (s, 3H), 4.25-4.32 (m, 2H), 5.32 (s, 2H), 6.23 (s, 1H), 7.35 (s, 1H), 7.88 (s, 1H), 8.03 (s, 2H), 12.70 (br s, 1H); ESI-MS (m/z) 626.18 (M+H)⁺.

Example 16

N-{4-[3-Chloro-5-fluoro-4-(2,2,2-trifluoroethoxy)phenyl]-1,3-thiazol-2-yl}-2-(1,3-dimethyl-2,4-dioxo-1,2,3,4-tetrahydro-5H-pyrrolo[3,2-d]pyrimidin-5-yl)acetamide

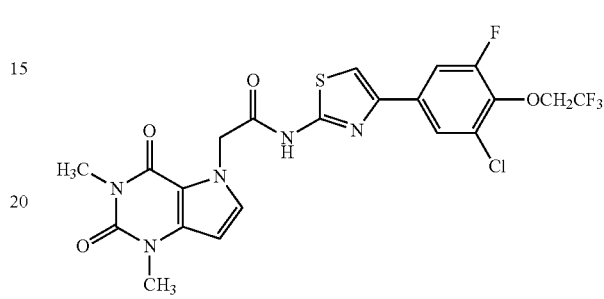

The title compound was prepared according to the general procedure (Method A) by coupling Intermediate 1 (33 mg, 0.184 mmol) with 2-bromo-N-{4-[3-chloro-5-fluoro-4-(2,2,2-trifluoroethoxy)phenyl]-1,3-thiazol-2-yl}acetamide (70 mg, 0.156 mmol) in the presence of NaH (11 mg, 0.458 mmol) in dry DMF (5.0 mL) to give 11 mg of the product as an off-white solid; ¹H NMR (δ ppm, DMSO-d₆, 300 MHz) 3.17 (s, 3H), 3.39 (s, 3H), 4.84 (q, J=8.7 Hz, 2H), 5.32 (s, 2H), 6.23 (s, 1H), 7.35 (s, 1H), 7.82-7.91 (m, 3H), 12.71 (br s, 1H); APCI-MS (m/z) 546.03 (M+H)⁺.

Example 17

2-(1,3-Dimethyl-2,4-dioxo-1,2,3,4-tetrahydro-5H-pyrrolo[3,2-d]pyrimidin-5-yl)-N-{4-[4-(cyclopropylmethoxy)-3,5-difluorophenyl]-1,3-thiazol-2-yl}acetamide

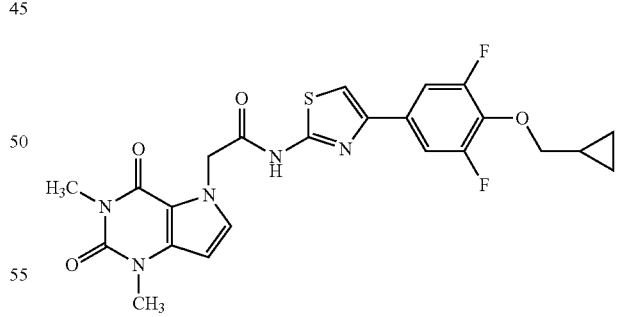

The title compound was prepared according to the general procedure (Method A) by coupling Intermediate 1 (50 mg, 0.279 mmol) with 2-bromo-N-{4-[4-(cyclopropylmethoxy)-3,5-difluorophenyl]-1,3-thiazol-2-yl}acetamide (135 mg, 0.334 mmol) in the presence of NaH (16 mg, 0.666 mmol) in dry DMF (5.0 mL) to give 39 mg of the product as an off-white solid; ¹H NMR (δ ppm, 300 MHz, DMSO-d₆) 0.24-0.30 (m, 2H), 0.50-0.56 (m, 2H), 1.15-1.21 (m, 1H), 3.17 (s, 3H), 3.39 (s, 3H), 3.97 (d, J=7.5 Hz, 2H), 5.32 (s, 2H), 6.23 (s, 2H), 7.35 (s, 1H), 7.60-7.66 (m, 2H), 7.77 (s, 1H), 12.68 (br s, 1H); APCI-MS (m/z) 502.13 (M+H)+.

Example 18

2-(1,3-Dimethyl-2,4-dioxo-1,2,3,4-tetrahydro-5H-pyrrolo[3,2-d]pyrimidin-5-yl)-N-{4-[4-(cyclobutylmethoxy)-3,5-difluorophenyl]-1,3-thiazol-2-yl}acetamide

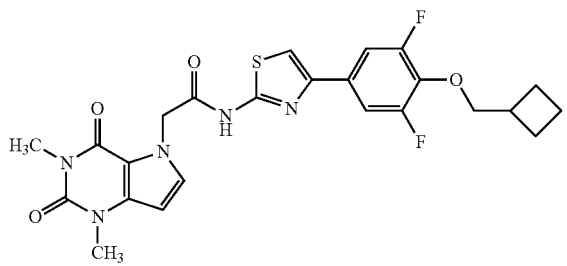 [SMILES: Cn1c(=O)c2c(ccn2CC(=O)Nc2nc(-c3cc(F)c(OCC4CCC4)c(F)c3)cs2)n(C)c1=O]

The title compound was prepared according to the general procedure (Method A) by coupling Intermediate 1 (50 mg, 0.279 mmol) with 2-bromo-N-{4-[4-(cyclobutylmethoxy)-3,5-difluorophenyl]-1,3-thiazol-2-yl}acetamide (139 mg, 0.334 mmol) in the presence of NaH (16 mg, 0.666 mmol) in dry DMF (5.0 mL) to give 44 mg of the product as a white solid; $^1$H NMR (δ ppm, 300 MHz, DMSO-$d_6$) 1.82-1.90 (m, 4H), 2.00-2.06 (m, 2H), 2.65-2.70 (m, 1H), 3.17 (s, 3H), 3.39 (s, 3H), 4.07-4.13 (m, 2H), 5.32 (s, 2H), 6.20-6.26 (m, 1H), 7.34 (s, 1H), 7.63 (d, J=8.7 Hz, 2H), 7.77 (s, 1H), 12.67 (br s, 1H); APCI-MS (m/z) 516.11 (M+H)+.

Example 19

2-(1,3-Dimethyl-2,4-dioxo-1,2,3,4-tetrahydro-5H-pyrrolo[3,2-d]pyrimidin-5-yl)-N-{4-[4-(cyclobutylmethoxy)-3,5-dichlorophenyl]-1,3-thiazol-2-yl}acetamide

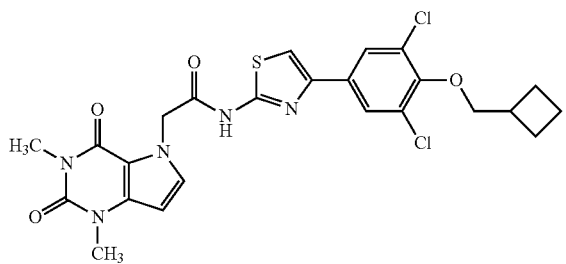 [SMILES: Cn1c(=O)c2c(ccn2CC(=O)Nc2nc(-c3cc(Cl)c(OCC4CCC4)c(Cl)c3)cs2)n(C)c1=O]

The title compound was prepared according to the general procedure (Method A) by coupling Intermediate 1 (45 mg, 0.251 mmol) with 2-bromo-N-{4-[4-(cyclobutylmethoxy)-3,5-dichlorophenyl]-1,3-thiazol-2-yl}acetamide (135 mg, 0.301 mmol) in the presence of NaH (16 mg, 0.666 mmol) in dry DMF (5.0 mL) to give 65 mg of the product as an off-white solid; $^1$H NMR ((δ ppm, 300 MHz, DMSO-$d_6$) 1.90-1.99 (m, 4H), 2.04-2.10 (m, 2H), 2.72-2.80 (m, 1H), 3.17 (s, 3H), 3.39 (s, 3H), 4.00 (d, J=6.3 Hz, 2H), 5.32 (s, 2H), 6.22 (s, 1H), 7.36 (s, 1H), 7.85 (s, 1H), 8.00 (s, 2H), 12.68 (br s, 1H); ESI-MS (m/z) 548.15 (M+H)+.

Example 20

2-(1,3-Dimethyl-2,4-dioxo-1,2,3,4-tetrahydro-5H-pyrrolo[3,2-d]pyrimidin-5-yl)-N-{4-[3,5-difluoro-4-[2-(trifluoromethyl)benzyloxy]phenyl)-1,3-thiazol-2-yl}acetamide

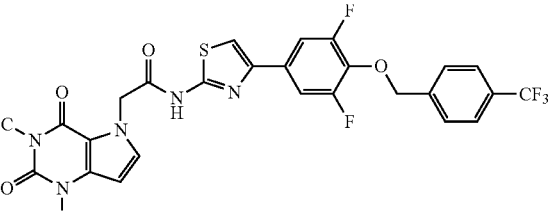

The title compound was prepared according to the general procedure (Method A) by coupling Intermediate 1 (50 mg, 0.279 mmol) with 2-bromo-N-{4,3,5-difluoro-[4-[2-(trifluoromethyl)benzyloxy]phenyl]-1,3-thiazol-2-yl}acetamide (170 mg, 0.335 mmol) in the presence of NaH (17 mg, 0.419 mmol) in dry DMF (5.0 mL) to give 35 mg of the product as a white solid; $^1$H NMR (δ ppm, 300 MHz, DMSO-$d_6$) 3.17 (s, 3H), 3.39 (s, 3H), 5.32 (s, 2H), 5.35 (s, 2H), 6.23 (s, 1H), 7.35 (s, 1H), 7.65-7.68 (m, 3H), 7.84-7.80 (m, 4H), 12.69 (br s, 1H); APCI-MS (m/z) 606.35 (M+H)+.

2-(1,3-Dimethyl-2,4-dioxo-1,2,3,4-tetrahydro-5H-pyrrolo[3,2-d]pyrimidin-5-yl)-N-{4-[3,5-difluoro-4-[4-(trifluoromethyl)benzyloxy]phenyl)-1,3-thiazol-2-yl}acetamide The title compound was prepared according to the general procedure (Method A) by coupling Intermediate 1 (33 mg, 0.184 mmol) with 2-bromo-N-{4-[3,5-difluoro-4-[4-(trifluoromethyl)benzyloxy)phenyl]-1,3-thiazol-2-yl}acetamide (112 mg, 0.221 mmol) in the presence of NaH (11 mg, 0.276 mmol) in dry DMF (3.0 mL) to give 25 mg of the product as a white solid; $^1$H NMR (δ ppm, 300 MHz, DMSO-$d_6$) 3.17 (s, 3H), 3.39 (s, 3H), 5.32 (s, 2H), 6.22 (br s, 4H), 6.22 (s, 1H), 7.35 (s, 1H), 7.70-7.72 (m, 4H), 7.78-7.80 (m, 3H), 12.68 (br s, 1H); ESI-MS (m/z) 606.15 (M+H)+.

Example 22

N-[4-(3-Fluoro-4-trifluoromethylphenyl)-1,3-thiazol-2-yl]-2-(1,3,6-trimethyl-2,4-dioxo-1,2,3,4-tetrahydro-5H-pyrrolo[3,2-d]pyrimidin-5-yl)acetamide

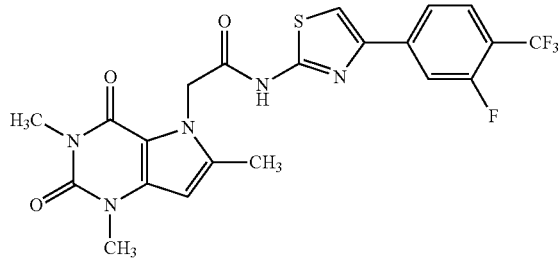 [SMILES: Cc1cc2c(c(=O)n(C)c(=O)n2C)n1CC(=O)Nc1nc(-c2ccc(C(F)(F)F)c(F)c2)cs1]

The title compound was prepared according to the general procedure (Method A) by coupling Intermediate 2 (45 mg, 0.232 mmol) with 2-bromo-N-{4-[3-fluoro-4-trifluoromethylphenyl]-1,3-thiazol-2-yl}acetamide (107 mg, 0.279 mmol) in the presence of NaH (13 mg, 0.555 mmol) in dry DMF (5.0 mL) to give 35 mg of the product as an off-white solid; $^1$H NMR (δ ppm, 300 MHz, DMSO-$d_6$) 2.27 (s, 3H), 3.17 (s, 3H), 3.36 (s, 3H), 5.34 (s, 2H), 6.07 (s, 1H), 7.85-7.91 (m, 1H), 7.94-8.05 (m, 3H), 12.82 (br s, 1H); ESI-MS (m/z) 496.23 (M+H)$^+$.

Example 23

N-{4-[3-Bromo-4-(2,2,2-trifluoroethoxy)phenyl]-1,3-thiazol-2-yl}-2-(1,3-dimethyl-2,4-dioxo-1,2,3,4-tetrahydro-5H-pyrrolo[3,2-d]pyrimidin-5-yl)acetamide

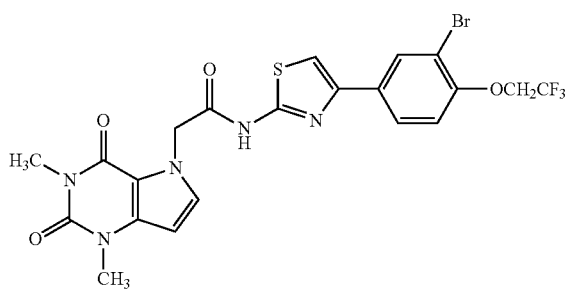

The title compound was prepared according to the general procedure (Method A) by coupling Intermediate 1 (50 mg, 0.279 mmol) with 2-bromo-N-{4-[3-bromo-4-(2,2,2-trifluoroethoxy)phenyl]-1,3-thiazol-2-yl}acetamide (158 mg, 0.333 mmol) in the presence of NaH (10 mg, 0.416 mmol) in dry DMF (5.0 mL) to give 30 mg of the product as a white solid; $^1$H NMR (δ ppm, 300 MHz, DMSO-$d_6$) 3.17 (s, 3H), 3.39 (s, 3H), 4.91 (d, J=8.7 Hz, 2H), 5.32 (s, 2H), 6.22 (s, 1H), 7.30-7.38 (m, 2H), 7.69 (s, 1H), 7.89-7.95 (m, 1H), 8.17 (m, 1H), 12.65 (br s, 1H); APCI-MS (m/z) 572.27 (M+H)$^+$.

Example 24

N1-{4-[3,5-Difluoro-4-(2,2-dimethylpropoxy)phenyl]-1,3-thiazol-2-yl}-2-(1,3,6-trimethyl-2,4-dioxo-1,2,3,4-tetrahydro-5H-pyrrolo[3,2-d]pyrimidin-5-yl)acetamide

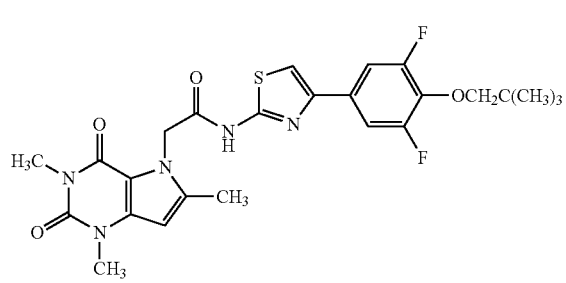

The title compound was prepared according to the general procedure (Method A) by coupling Intermediate 2 (50 mg, 0.258 mmol) with 2-bromo-N-{4-[4-(2,2-dimethylpropoxy)-3,5-difluorophenyl]-1,3-thiazol-2-yl}acetamide (130 mg, 0.310 mmol) in the presence of NaH (15 mg, 0.625 mmol) in dry DMF (5.0 mL) to give 55 mg of the product as a white solid; $^1$H NMR (δ ppm, 300 MHz, DMSO-$d_6$) 1.01 (s, 9H), 2.26 (s, 3H), 3.17 (s, 3H), 3.34 (s, 3H), 3.80 (s, 2H), 5.33 (s, 2H), 6.07 (s, 1H), 7.63 (s, 1H), 7.66 (s, 1H), 7.77 (s, 1H), 12.74 (br s, 1H); ESI-MS (m/z) 532.24 (M+H)$^+$.

Example 25

N-{4-[2,4-Difluoro-3-trifluoromethyl)phenyl]-1,3-thiazol-2-yl}-2-(1,3,6-trimethyl-2,4-dioxo-1,2,3,4-tetrahydro-5H-pyrrolo[3,2-d]pyrimidin-5-yl)acetamide

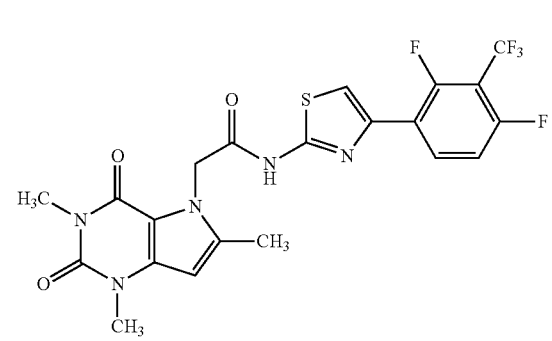 [SMILES: Cc1cc2c(c(=O)n(C)c(=O)n2C)n1CC(=O)Nc1nc(-c2ccc(F)c(C(F)(F)F)c2F)cs1]

The title compound was prepared according to the general procedure (Method A) by coupling Intermediate 2 (50 mg, 0.258 mmol) with 2-bromo-N-{4-[2,4-difluoro-3-trifluoromethyl)phenyl]-1,3-thiazol-2-yl}acetamide (124 mg, 0.310 mmol) in the presence of NaH (15 mg, 0.625 mmol) in dry DMF (5.0 mL) to give 35 mg of the product as a white solid; $^1$H NMR (δ ppm, 300 MHz, DMSO-$d_6$) 2.27 (s, 3H), 3.16 (s, 3H), 3.34 (s, 3H), 5.34 (s, 2H), 6.07 (s, 1H), 7.47-7.57

(m, 1H), 7.66 (s, 1H), 8.28-8.38 (m, 1H), 12.80 (br s, 1H); APCI-MS (m/z) 514.08 (M+H)⁺.

Example 26

N-[4-(3,5-Difluoro-4-(2,2,2-trifluoroethoxy)phenyl)-1,3-thiazol-2-yl]-2-(1,3,6-trimethyl-2,4-dioxo-1,2,3,4-tetrahydro-5H-pyrrolo[3,2-d]pyrimidin-5-yl)acetamide

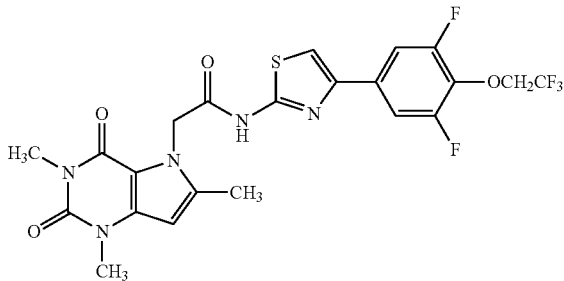

The title compound was prepared according to the general procedure (Method A) by coupling Intermediate 2 (50 mg, 0.258 mmol) with 2-bromo-N-{4-(3,5-difluoro-4-(2,2,2-trifluoroethoxy)phenyl)-1,3-thiazol-2-yl}acetamide (133 mg, 0.308 mmol) in the presence of NaH (16 mg, 0.375 mmol) in dry DMF (5.0 mL) to give 60 mg of the product as a white solid; ¹H NMR (δ ppm, 300 MHz, DMSO-d₆) 2.26 (s, 3H), 3.16 (s, 3H), 3.34 (s, 3H), 4.80-4.90 (m, 2H), 5.33 (s, 2H), 6.07 (s, 1H), 7.71 (d, J=9.3 Hz, 2H), 7.83 (s, 1H), 12.75 (br s, 1H); ESI-MS (m/z) 544.55 (M+H)⁺.

Example 27

N-[4-(4-Cyclobutylmethoxy-3,5-difluorophenyl)-1,3-thiazol-2-yl]-2-(1,3,6-trimethyl-2,4-dioxo-1,2,3,4-tetrahydro-5H-pyrrolo[3,2-d]pyrimidin-5-yl)acetamide

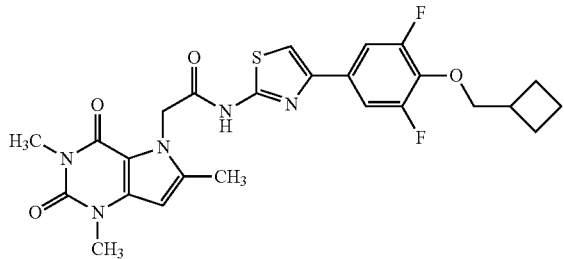 [SMILES: Cc1cc2c(c(=O)n(C)c(=O)n2C)n1CC(=O)Nc1nc(-c2cc(F)c(OCC3CCC3)c(F)c2)cs1]

The title compound was prepared according to the general procedure (Method A) by coupling Intermediate 2 (50 mg, 0.258 mmol) with 2-bromo-N-{4-[4-Cyclobutylmethoxy-3,5-difluorophenyl]-1,3-thiazol-2-yl}acetamide (129 mg, 0.308 mmol) in the presence of NaH (16 mg, 0.375 mmol) in dry DMF (5.0 mL) to give 65 mg of the product as an off-white solid; ¹H NMR (δ ppm, 300 MHz, DMSO-d₆) 1.82-1.88 (m, 4H), 2.00-2.06 (m, 2H), 2.26 (s, 3H), 2.65-2.70 (m, 1H), 3.17 (s, 3H), 3.33 (s, 3H), 4.10 (d, J=6.6 Hz, 2H), 5.33 (s, 2H), 6.06 (s, 1H), 7.63 (d, J=8.7 Hz, 2H), 7.77 (s, 1H), 12.71 (br s, 1H); APCI-MS (m/z) 530.16 (M+H)⁺.

Example 28

N-{4-[3-Chloro-4-(2,2-dimethylpropoxy)-5-fluorophenyl]-1,3-thiazol-2-yl}-2-(1,3,6-trimethyl-2,4-dioxo-1,2,3,4-tetrahydro-5H-pyrrolo[3,2-d]pyrimidin-5-yl)acetamide

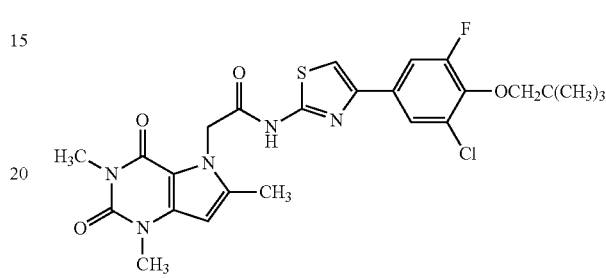

The title compound was prepared according to the general procedure (Method A) by coupling Intermediate 2 (50 mg, 0.258 mmol) with 2-bromo-N-{4-[3-chloro-4-(2,2-dimethylpropoxy)-5-fluorophenyl]-1,3-thiazol-2-yl}acetamide (135 mg, 0.310 mmol) in the presence of NaH (15 mg, 0.375 mmol) in dry DMF (5.0 mL) to give 75 mg of the product as a white solid; ¹H-NMR (δ ppm, DMSO-d₆, 300 MHz) 1.04 (s, 9H), 2.26 (s, 3H), 3.17 (s, 3H), 3.34 (s, 3H), 3.78 (s, 2H), 5.33 (s, 2H), 6.07 (s, 1H), 7.70-7.86 (m, 3H), 12.74 (br s, 1H, exchangeable with D₂O); ESI-MS (m/z) 548.12 (M+H)⁺.

Example 29

N-{4-[3,5-dichloro-4-(2,2-dimethylpropoxy)phenyl]-1,3-thiazol-2-yl}-2-(1,3,6-trimethyl-2,4-dioxo-1,2,3,4-tetrahydro-5H-pyrrolo[3,2-d]pyrimidin-5-yl)acetamide

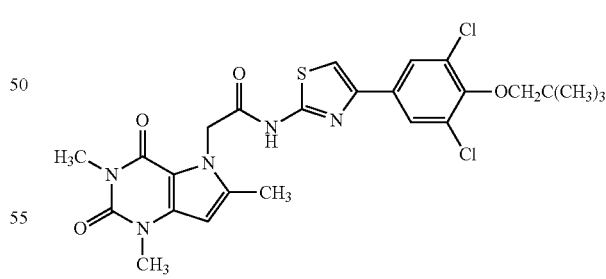

The title compound was prepared according to the general procedure (Method A) by coupling Intermediate 2 (50 mg, 0.258 mmol) with 2-bromo-N-{4-[3,5-dichloro-4-(2,2-dimethylpropoxy)phenyl]-1,3-thiazol-2-yl}acetamide (140 mg, 0.310 mmol) in the presence of NaH (15 mg, 0.375 mmol) in dry DMF (5.0 mL) to give 70 mg of the product as a white solid; ¹H-NMR (δ ppm, DMSO-d₆, 300 MHz) 1.08 (s, 9H), 2.27 (s, 3H), 3.17 (s, 3H), 3.33 (s, 3H), 3.67 (s, 2H), 5.33 (s, 2H), 6.07 (s, 1H), 7.85 (s, 1H), 8.00 (s, 2H), 12.73 (br s, 1H, exchangeable with D$_2$O); ESI-MS (m/z) 564.22 (M+H)$^+$.

(s, 1H), 7.22 (t, J=8.4 Hz, 1H), 7.59 (s, 1H), 7.65-7.75 (m, 2H), 12.77 (br s, 1H, exchangeable with D$_2$O); APCI-MS (m/z) 514.16 (M+H)$^+$.

Example 30

N-{4-[3-Chloro-5-fluoro-4-(2,2,2-trifluoroethoxy) phenyl]-1,3-thiazol-2-yl]}-2-(1,3,6-trimethyl-2,4-dioxo-1,2,3,4-tetrahydro-5H-pyrrolo[3,2-d]pyrimidin-5-yl)acetamide

Example 32

N-{4-[3-Chloro-4-(2,2-dimethylprop oxy)phenyl]-1,3-thiazol-2-yl}-2-(1,3,6-trimethyl-2,4-dioxo-1,2,3,4-tetrahydro-5H-pyrrolo[3,2-d]pyrimidin-5-yl)acetamide

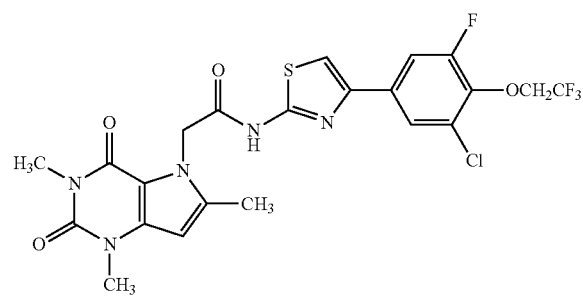

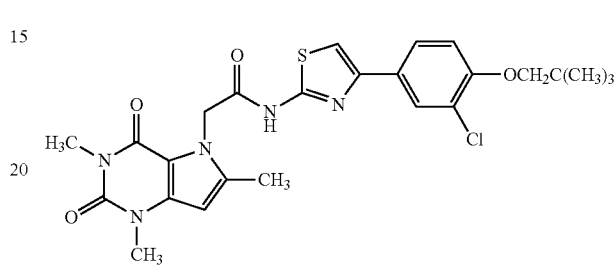

The title compound was prepared according to the general procedure (Method A) by coupling Intermediate 2 (50 mg, 0.258 mmol) with 2-bromo-N-{4-[3-chloro-5-fluoro-4-(2,2,2-trifluoroethoxy)phenyl]-1,3-thiazol-2-yl}acetamide (139 mg, 0.310 mmol) in the presence of NaH (15 mg, 0.375 mmol) in dry DMF (5.0 mL) to give 65 mg of the product as a white solid; $^1$H-NMR (δ ppm, DMSO-d$_6$, 300 MHz) 2.26 (s, 3H), 3.16 (s, 3H), 3.33 (s, 3H), 4.84 (q, J=8.7 Hz, 2H), 5.33 (s, 2H), 6.07 (s, 1H), 7.80-7.90 (m, 3H), 12.75 (br s, 1H, exchangeable with D$_2$O); ESI-MS (m/z) 560.10 (M+H)$^+$.

The title compound was prepared according to the general procedure (Method A) by coupling Intermediate 2 (50 mg, 0.258 mmol) with 2-bromo-N-{4-[3-chloro-4-(2,2-dimethylpropoxy)phenyl]-1,3-thiazol-2-yl}acetamide (129 mg, 0.308 mmol) in the presence of NaH (15 mg, 0.375 mmol) in dry DMF (5.0 mL) to give 85 mg of the product as a white solid; $^1$H-NMR (δ ppm, DMSO-d$_6$, 300 MHz): 1.04 (s, 9H), 2.27 (s, 3H), 3.17 (s, 3H), 3.36 (s, 3H), 3.76 (s, 2H), 5.32 (s, 2H), 6.07 (s, 1H), 7.19 (d, J=8.7 Hz, 1H), 7.62 (s, 1H), 7.82 (d, J=8.4 Hz, 1H), 7.96 (s, 1H), 12.69 (br s, 1H, exchangeable with D$_2$O); APCI-MS (m/z) 530.26 (M+H)$^+$.

Example 31

N-{4-[4-(2,2-Dimethylpropoxy)-3-fluorophenyl]-1,3-thiazol-2-yl}-2-(1,3,6-trimethyl-2,4-dioxo-1,2,3,4-tetrahydro-5H-pyrrolo[3,2-d]pyrimidin-5-yl)acetamide

Example 33

N-[5-(4-bromophenyl)isoxazol-3-yl]-2-(1,3,6-trimethyl-2,4-dioxo-1,2,3,4-tetrahydro-5H-pyrrolo[3,2-d]pyrimidin-5-yl)acetamide

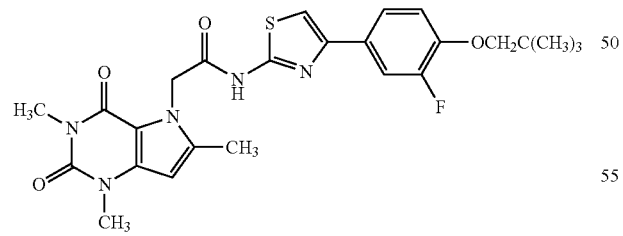

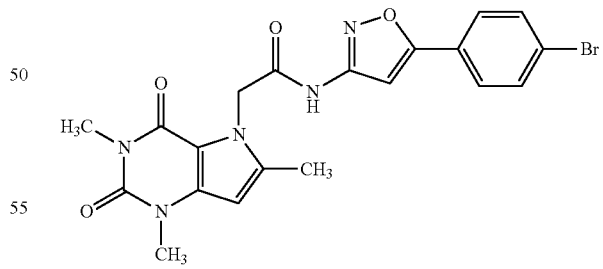

The title compound was prepared according to the general procedure (Method A) by coupling Intermediate 2 (50 mg, 0.258 mmol) with 2-bromo-N-{4-[4-(2,2-dimethylpropoxy)-3-fluorophenyl]-1,3-thiazol-2-yl}acetamide (124 mg, 0.310 mmol) in the presence of NaH (15 mg, 0.375 mmol) in dry DMF (5.0 mL) to give 55 mg of the product as a white solid; $^1$H-NMR (δ ppm, DMSO-d$_6$, 300 MHz) 1.06 (s, 9H), 2.26 (s, 3H), 3.17 (s, 3H), 3.36 (s, 3H), 3.75 (s, 2H), 5.32 (s, 2H), 6.07

The title compound was prepared according to the general procedure (Method A) by coupling Intermediate 2 (50 mg, 0.258 mmol) with 2-bromo-N-[5-(4-bromophenyl)isoxazol-3-yl]acetamide (111 mg, 0.310 mmol) in the presence of NaH (15 mg, 0.375 mmol) in dry DMF (5.0 mL) to give 40 mg of the product as a white solid; $^1$H-NMR (δ ppm, DMSO-d$_6$, 300 MHz) 2.26 (s, 3H), 3.18 (s, 3H), 3.34 (s, 3H), 5.27 (s, 2H), 6.05 (s, 1H), 7.35 (s, 1H), 7.72 (d, J=8.7 Hz, 2H), 7.82 (d, J=8.7 Hz, 2H), 11.56 (br s, 1H, exchangeable with D₂O); ESI-MS (m/z) 472.08 (M+H)⁺.

Example 34

N-{4-[3,5-Difluoro-4-(2,2-dimethylpropoxy)phenyl]-1,3-thiazol-2-yl}-2-(1,3,7-trimethyl-2,4-dioxo-1,2,3,4-tetrahydro-5H-pyrrolo[3,2-d]pyrimidin-5-yl)acetamide

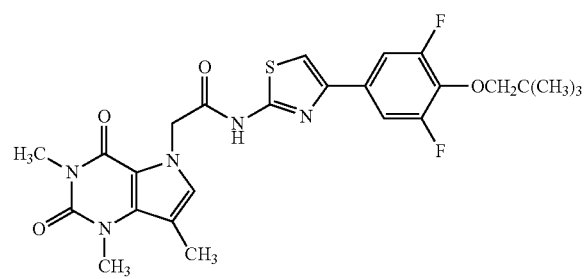

The title compound was prepared according to the general procedure (Method A) by coupling Intermediate 3 (50 mg, 0.258 mmol) with 2-bromo-N-{4-[3,5-difluoro-4-(2,2-dimethylpropoxy)phenyl]-1,3-thiazol-2-yl}acetamide (130 mg, 0.310 mmol) in the presence of NaH (15 mg, 0.375 mmol) in dry DMF (5.0 mL) to give 75 mg of the product as a white solid; ¹H-NMR (δ ppm, DMSO-d₆, 300 MHz) 1.01 (s, 9H), 2.29 (s, 3H), 3.16 (s, 3H), 3.59 (s, 3H), 3.80 (s, 2H), 5.25 (s, 2H), 7.12 (s, 1H), 7.63 (d, J=9.6 Hz, 2H), 7.76 (s, 1H), 12.63 (br s, 1H, exchangeable with D₂O); ESI-MS (m/z) 532.18 (M+H)⁺.

Example 35

N-{4-[3-Fluoro-4-(trifluoromethyl)phenyl]-1,3-thiazol-2-yl}-2-(1,3,7-trimethyl-2,4-dioxo-1,2,3,4-tetrahydro-5H-pyrrolo[3,2-d]pyrimidin-5-yl)acetamide

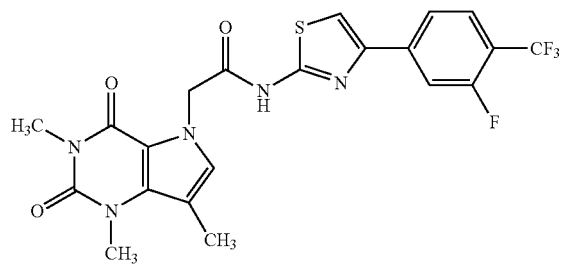 [SMILES: Cc1cn(CC(=O)Nc2nc(-c3ccc(C(F)(F)F)c(F)c3)cs2)c2c(=O)n(C)c(=O)n(C)c12]

The title compound was prepared according to the general procedure (Method A) by coupling Intermediate 3 (50 mg, 0.258 mmol) with 2-bromo-N-{4-[3-fluoro-4-(trifluoromethyl)phenyl]-1,3-thiazol-2-yl}acetamide (119 mg, 0.310 mmol) in the presence of NaH (15 mg, 0.375 mmol) in dry DMF (5.0 mL) to give 90 mg of the product as a white solid; ¹H-NMR (δ ppm, DMSO-d₆, 300 MHz) 2.29 (s, 3H), 3.16 (s, 3H), 3.59 (s, 3H), 5.26 (s, 2H), 7.12 (s, 1H), 7.82-8.00 (m, 4H), 12.71 (br s, 1H, exchangeable with D₂O); APCI-MS (m/z) 494.30 (M−H)⁻.

Example 36

2-(7-Bromo-1,3-dimethyl-2,4-dioxo-1,2,3,4-tetrahydro-5H-pyrrolo[3,2-d]pyrimidin-5-yl)-N-{4-[3,5-difluoro-4-(2,2-dimethylpropoxy)phenyl]-1,3-thiazol-2-yl}acetamide

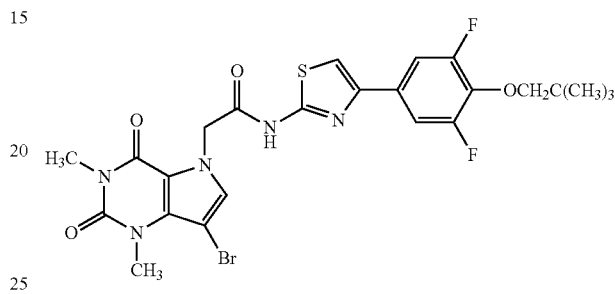

The title compound was prepared according to the general procedure (Method A) by coupling Intermediate 4 (50 mg, 0.193 mmol) with 2-bromo-N-{4-[3,5-difluoro-4-(2,2-dimethylpropoxy)phenyl]-1,3-thiazol-2-yl}acetamide (97 mg, 0.232 mmol) in the presence of NaH (11 mg, 0.289 mmol) in dry DMF (5.0 mL) to give 40 mg of the product as a white solid; ¹H-NMR (δ ppm, DMSO-d₆, 300 MHz) 1.01 (s, 9H), 3.17 (s, 3H), 3.67 (s, 3H), 3.80 (s, 2H), 5.32 (s, 2H), 7.54 (s, 1H), 7.63 (d, J=9.3 Hz, 2H), 7.80 (s, 1H), 12.70 (br s, 1H, exchangeable with D₂O); ESI-MS (m/z) 594.17 (M−H)⁻.

Example 37

2-(7-Bromo-1,3-dimethyl-2,4-dioxo-1,2,3,4-tetrahydro-5H-pyrrolo[3,2-d]pyrimidin-5-yl)-N-{4-[3-fluoro-4-(trifluoromethyl)phenyl]-1,3-thiazol-2-yl}acetamide

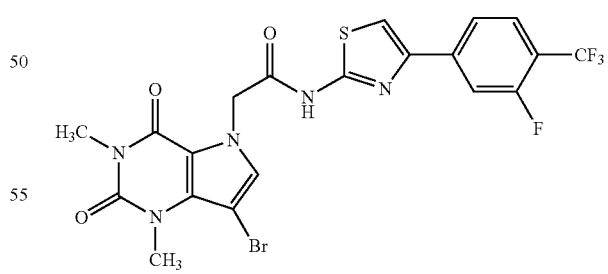

The title compound was prepared according to the general procedure (Method A) by coupling Intermediate 4 (50 mg, 0.193 mmol) with 2-bromo-N-{4-[3-fluoro-4-(trifluoromethyl)phenyl]-1,3-thiazol-2-yl}acetamide (89 mg, 0.232 mmol) in the presence of NaH (11 mg, 0.289 mmol) in dry DMF (5.0 mL) to give 50 mg of the product as a white solid; ¹H-NMR (δ ppm, DMSO-d₆, 300 MHz) 3.17 (s, 3H), 3.68 (s, 3H), 5.33 (s, 2H), 7.55 (s, 1H), 7.87 (d, J=7.8 Hz, 1H), 7.91-8.02 (m, 3H), 12.79 (br s, 1H, exchangeable with D$_2$O); APCI-MS (m/z) 560.12 (M+H)$^+$.

Example 38

N-{4-[3-Fluoro-4-(trifluoromethyl)phenyl]-1,3-thiazol-2-yl}-2-{7-[(dimethylamino)methyl]-1,3-dimethyl-2,4-dioxo-1,2,3,4-tetrahydro-5H-pyrrolo[3,2-d]pyrimidin-5-yl}acetamide

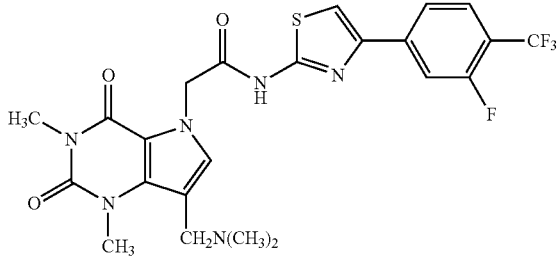

The title compound was prepared according to the general procedure (Method A) by coupling Intermediate 5 (40 mg, 0.169 mmol) with 2-bromo-N-{4-[3-fluoro-4-(trifluoromethyl)phenyl]-1,3-thiazol-2-yl}acetamide (77 mg, 0.203 mmol) in the presence of NaH (10 mg, 0.250 mmol) in dry DMF (4.0 mL) to give 35 mg of the product as a white solid; $^1$H-NMR (δ ppm, DMSO-d$_6$, 300 MHz) 2.15 (s, 3H), 3.17 (s, 3H), 3.32 (s, 2H, overlapped with residual DMSO peak), 3.71 (s, 3H), 5.29 (s, 2H), 7.24 (s, 1H), 7.86-8.01 (m, 4H), 12.84 (br s, 1H, exchangeable with D$_2$O); ESI-MS (m/z) 539.12 (M+H)$^+$.

Example 39

N-{4-[3,5-Difluoro-4-(2,2-dimethylpropoxy)phenyl]-1,3-thiazol-2-yl}-2-{7-[(dimethylamino)methyl]-1,3-dimethyl-2,4-dioxo-1,2,3,4-tetrahydro-5H-pyrrolo[3,2-d]pyrimidin-5-yl}acetamide The title compound was prepared according to the general procedure (Method A) by coupling Intermediate 5 (50 mg, 0.211 mmol) with 2-bromo-N-{-4-[3,5-difluoro-4-(2,2-dimethylpropoxy)phenyl]-1,3-thiazol-2-yl}acetamide (106 mg, 0.253 mmol) in the presence of NaH (15 mg, 0.375 mmol) in dry DMF (5.0 mL) to give 30 mg of the product as a white solid; $^1$H-NMR (δ ppm, DMSO-d$_6$, 300 MHz) 1.01 (s, 9H), 2.16 (s, 3H), 3.17 (s, 3H), 3.34 (s, 2H, overlapped with residual DMSO peak), 3.71 (s, 3H), 3.80 (s, 3H), 5.28 (s, 2H), 7.24 (s, 1H), 7.65 (d, J=9.6 Hz, 2H), 7.76 (s, 1H), 12.66 (br s, 1H, exchangeable with D$_2$O); APCI-MS (m/z) 575.02 (M+H)$^+$.

Example 40

N-{4-[3-Fluoro-4-(trifluoromethyl)phenyl]-1,3-thiazol-2-yl}-2-{7-[(diethylamino)methyl]-1,3-dimethyl-2,4-dioxo-1,2,3,4-tetrahydro-5H-pyrrolo[3,2-d]pyrimidin-5-yl}acetamide

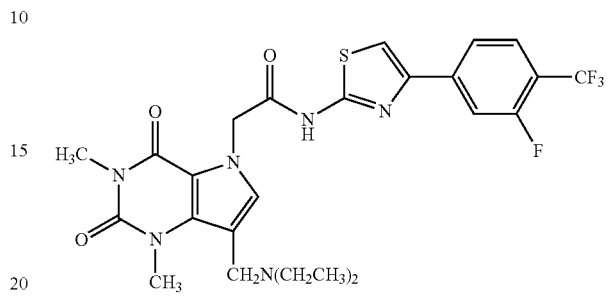

The title compound was prepared according to the general procedure (Method A) by coupling Intermediate 6 (50 mg, 0.189 mmol) with 2-bromo-N-{4-[3-fluoro-4-(trifluoromethyl)phenyl]-1,3-thiazol-2-yl}acetamide (86 mg, 0.224 mmol) in the presence of NaH (11 mg, 0.250 mmol) in dry DMF (5.0 mL) to give 50 mg of the product as a white solid; $^1$H-NMR (δ ppm, DMSO-d$_6$, 300 MHz) 0.96 (t, J=6.9 Hz, 6H), 2.47-2.53 (m, 4H, overlapped with residual DMSO peak), 3.17 (s, 3H), 3.50 (s, 2H), 3.75 (s, 3H), 5.29 (s, 2H), 7.27 (s, 1H), 7.83-8.02 (m, 4H), 12.76 (br s, 1H, exchangeable with D$_2$O); ESI-MS (m/z) 567.00 (M+H)$^+$.

Example 41

N-{4-[3-Fluoro-4-(trifluoromethyl)phenyl]-1,3-thiazol-2-yl}-2-(1,3,7-trimethyl-2,4-dioxo-2,3,4,7-tetrahydro-1H-pyrrolo[2,3-d]pyrimidin-5-yl)acetamide

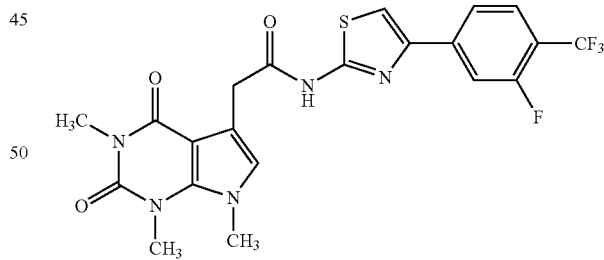

The title compound was prepared according to the general procedure (Method B) by coupling Intermediate 7 (80 mg, 0.318 mmol) with 4-[3-fluoro-4-(trifluoromethyl)phenyl]-1,3-thiazol-2-amine (84 mg, 0.318 mmol) in the presence of EDCI hydrochloride (74 mg, 0.381 mmol), HOBt (13 mg, 0.096 mmol) and DMAP (4 mg, 0.032 mmol) in 1,2-dichloroethane (4 mL) to give 52 mg of the product as an off white solid; $^1$H-NMR (δ ppm, DMSO-d$_6$, 300 MHz) 3.21 (s, 3H), 3.73 (s, 3H), 3.80 (s, 3H), 3.95 (s, 2H), 6.35 (s, 1H), 7.82-8.02 (m, 4H), 12.62 (br s, 1H, exchangeable with D$_2$O); APCI-MS (m/z) 496.26 (M+H)$^+$.

Example 42

N-[4-(3,5-Difluoro-4-(2,2-dimethylprop oxy)phenyl)-1,3-thiazol-2-yl]-2-(1,3,7-trimethyl-2,4-dioxo-2,3,4,7-tetrahydro-1H-pyrrolo[2,3-d]pyrimidin-5-yl)acetamide

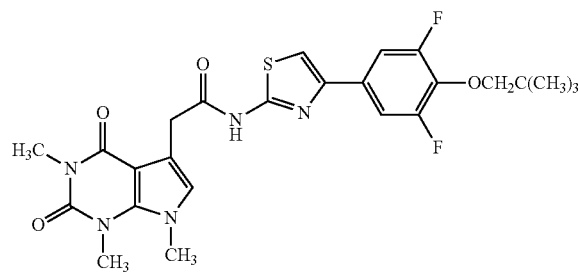

The title compound was prepared according to the general procedure (Method B) by coupling Intermediate 7 (100 mg, 0.398 mmol) with 4-[4-(2,2-dimethylpropoxy)-3,5-difluorophenyl]-1,3-thiazol-2-amine (118 mg, 0.398 mmol) in the presence of EDCI hydrochloride (91 mg, 0.475 mmol), HOBt (16 mg, 0.118 mmol) and DMAP (4 mg, 0.032 mmol) in 1,2-dichloroethane (5 mL) to give 40 mg of the product as an off white solid; $^1$H-NMR (δ ppm, DMSO-$d_6$, 300 MHz) 1.01 (s, 9H), 3.21 (s, 3H), 3.73 (s, 3H), 3.80 (s, 5H), 3.93 (s, 2H), 6.35 (s, 1H), 7.64 (d, J=9.6 Hz, 2H), 7.67 (s, 1H), 12.53 (br s, 1H, exchangeable with $D_2O$); ESI-MS (m/z) 532.24 (M+H)$^+$.

Example 43

N-{4-[2,4-Difluoro-3-(trifluoromethyl)phenyl]-1,3-thiazol-2-yl}-2-(1,3,7-trimethyl-2,4-dioxo-2,3,4,7-tetrahydro-1H-pyrrolo[2,3-d]pyrimidin-5-yl)acetamide

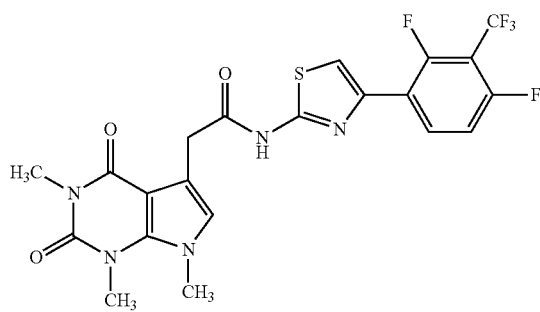 [SMILES: Cn1c(=O)c2c(CC(=O)Nc3nc(-c4ccc(F)c(C(F)(F)F)c4F)cs3)cn(C)c2n(C)c1=O]

The title compound was prepared according to the general procedure (Method B) by coupling Intermediate 7 (100 mg, 0.398 mmol) with 4-[2,4-difluoro-3-(trifluoromethyl)phenyl]-1,3-thiazol-2-amine (111 mg, 0.398 mmol) in the presence of EDCI hydrochloride (91 mg, 0.475 mmol), HOBt (16 mg, 0.118 mmol) and DMAP (4 mg, 0.032 mmol) in 1,2-dichloroethane (5 mL) to give 35 mg of the product as an off white solid; $^1$H-NMR (δ ppm, DMSO-$d_6$, 300 MHz) 3.21 (s, 3H), 3.73 (s, 3H), 3.81 (s, 3H), 3.95 (s, 2H), 6.35 (s, 1H), 7.51 (d, J=9.9 Hz, 1H), 8.32 (q, J=6.3 Hz, 1H), 12.61 (br s, 1H, exchangeable with $D_2O$); ESI-MS (m/z) 514.09 (M+H)$^+$.

Example 44

N-{4-[3,5-Difluoro-4-(2,2,2-trifluoroethoxy)phenyl]-1,3-thiazol-2-yl}-2-(1,3,7-trimethyl-2,4-dioxo-2,3,4,7-tetrahydro-1H-pyrrolo[2,3-d]pyrimidin-5-yl)acetamide

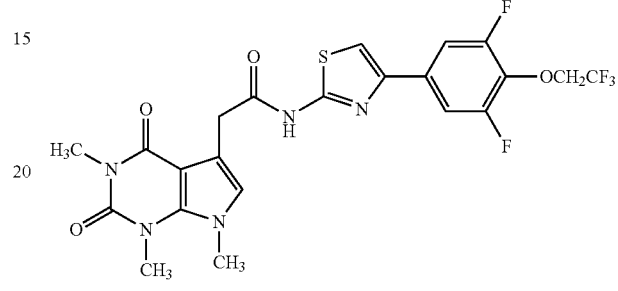

The title compound was prepared according to the general procedure (Method B) by coupling Intermediate 7 (100 mg, 0.398 mmol) with 4-[3,5-difluoro-4-(2,2,2-trifluoroethoxy)phenyl]-1,3-thiazol-2-amine (123 mg, 0.398 mmol) in the presence of EDCI hydrochloride (91 mg, 0.475 mmol), HOBt (16 mg, 0.118 mmol) and DMAP (4 mg, 0.032 mmol) in 1,2-dichloroethane (5 mL) to give 70 mg of the product as an off white solid; $^1$H-NMR (δ ppm, DMSO-$d_6$, 300 MHz) 3.21 (s, 3H), 3.73 (s, 3H), 3.80 (s, 5H), 3.94 (s, 2H), 4.85 (q, J=8.7 Hz, 2H), 6.35 (s, 1H), 7.69 (d, J=9.3 Hz, 2H), 7.82 (s, 1H), 12.55 (br s, 1H, exchangeable with $D_2O$); ESI-MS (m/z) 544.11 (M+H)$^+$.

Example 45

N-[4-(4-Isobutylphenyl)-1,3-thiazol-2-yl]-2-(2,5,7-trimethyl-4,6-dioxo-4,5,6,7-tetrahydro-2H-pyrazolo[3,4-d]pyrimidin-3-yl)acetamide

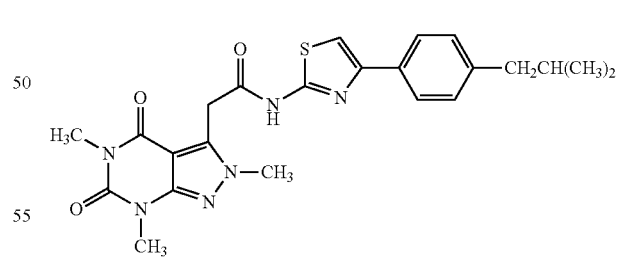

The title compound was prepared according to the general procedure (Method B) by coupling Intermediate 8 (200 mg, 0.793 mmol) with 4-(4-isobutylphenyl)-1,3-thiazol-2-amine (183 mg, 0.793 mmol) in the presence of EDCI hydrochloride (181 mg, 0.952 mmol), HOBt (32 mg, 0.238 mmol) and DMAP (9.6 mg, 0.079 mmol) in 1,2 dichloroethane (8 ml) to give 32 mg of the product as a white solid; $^1$H NMR (300 MHz, CDCl$_3$): δ 0.90 (d, J=6.6 Hz, 6H), 2.49 (d, J=5.1 Hz, 2H), 3.46 (s, 3H), 3.50 (s, 3H), 3.99 (s, 3H), 4.16 (s, 2H), 7.08

(s, 1H), 7.18 (d, J=7.8 Hz, 2H), 7.74 (d, J=8.4, 2H), 11.11 (br s, 1H); APCI-MS (m/z): 513.03 (M+H)⁺.

Example 46

N-[4-(4-Chlorophenyl)-1,3-thiazol-2-yl]-2-(2,5,7-trimethyl-4,6-dioxo-4,5,6,7-tetrahydro-2H-pyrazolo[3,4-d]pyrimidin-3-yl)acetamide

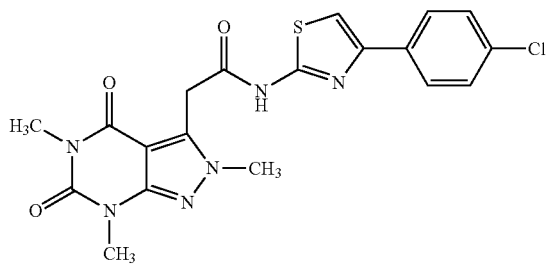 [SMILES: Cn1nc2c(c1CC(=O)Nc1nc(-c3ccc(Cl)cc3)cs1)c(=O)n(C)c(=O)n2C]

The title compound was prepared according to the general procedure (Method B) by coupling Intermediate 8 (250 mg, 0.992 mmol) with 4-(4-chlorophenyl)-1,3-thiazol-2-amine (208 mg, 0.992 mmol) in the presence of EDCI hydrochloride (228 mg, 1.190 mmol), HOBt (40 mg, 0.297 mmol) and DMAP (12.12 mg, 0.099 mmol) in 1,2-dichloroethane (8 ml) to give 35 mg of the product as an off-white solid; ¹H NMR (300 MHz, DMSO-d₆): δ 3.16 (s, 3H), 3.36 (s, 3H), 3.84 (s, 3H), 4.39 (s, 2H), 7.50 (d, J=8.4 Hz, 2H), 7.72 (s, 1H), 7.92 (d, J=9.0 Hz, 2H), 12.74 (br s, 1H); APCI-MS (m/z) 445.08 (M+H)⁺.

Example 47

N-{4-[4-(Trifluoromethyl)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide

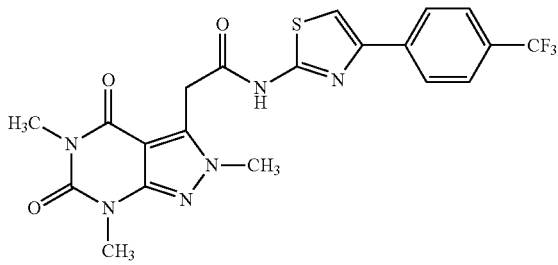 [SMILES: Cn1nc2c(c1CC(=O)Nc1nc(-c3ccc(C(F)(F)F)cc3)cs1)c(=O)n(C)c(=O)n2C]

The title compound was prepared according to the general procedure (Method B) by coupling Intermediate 8 (200 mg, 0.793 mmol) with 4-[4-(trifluoromethyl)phenyl]-1,3-thiazol-2-amine (193 mg, 0.793 mmol) in the presence of EDCI hydrochloride (182 mg, 0.951 mmol), HOBt (32 mg, 0.237 mmol) and DMAP (9.6 mg, 0.079 mmol) in 1,2-dichloroethane (7.9 ml) to give 13.4 mg of the product as an off-white solid; ¹H NMR (300 MHz, CDCl₃): δ 3.48 (s, 3H), 3.50 (s, 3H), 4.01 (s, 3H), 4.16 (s, 2H), 7.24 (s, 1H), 7.65 (d, J=7.8, 2H), 7.95 (d, J=7.8, 2H), 11.21 (br s, 1H); APCI-MS (m/z): 479.08 (M+H)⁺.

Example 48

N-{4-[3-(Trifluoromethyl)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide

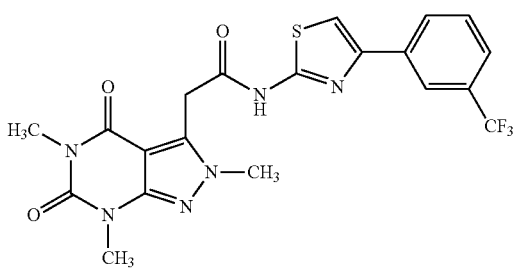 [SMILES: Cn1nc2c(c1CC(=O)Nc1nc(-c3cccc(C(F)(F)F)c3)cs1)c(=O)n(C)c(=O)n2C]

The title compound was prepared according to the general procedure (Method B) by coupling Intermediate 8 (250 mg, 0.992 mmol) with 4-[3-(trifluoromethyl)phenyl]-1,3-thiazol-2-amine (243 mg, 0.992 mmol) in the presence of EDCI hydrochloride (228 mg, 1.190 mmol), HOBt (40 mg, 0.297 mmol) and DMAP (12.12 mg, 0.099 mmol) in 1,2-dichloroethane (8 ml) to give 75 mg of the product as an off-white solid; ¹H NMR (300 MHz, DMSO-d₆): δ 3.17 (s, 3H), 3.37 (s, 3H), 3.85 (s, 3H), 4.40 (s, 2H), 7.70 (s, 2H), 7.91 (s, 1H), 8.23-8.29 (m, 2H), 12.80 (br s, 1H); APCI-MS (m/z) 479.09 (M+H)⁺.

Example 49

N-{4-[3-(Trifluoromethoxy)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide

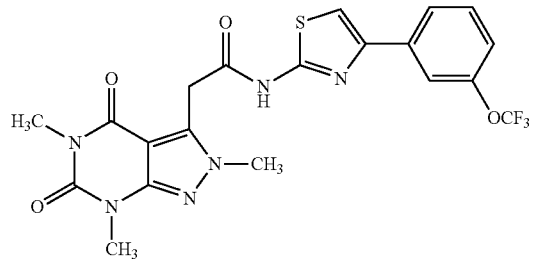 [SMILES: Cn1nc2c(c1CC(=O)Nc1nc(-c3cccc(OC(F)(F)F)c3)cs1)c(=O)n(C)c(=O)n2C]

The title compound was prepared according to the general procedure (Method B) by coupling Intermediate 8 (200 mg, 0.793 mmol) with 4-[3-(trifluoromethoxy)phenyl]-1,3-thiazol-2-amine (206 mg, 0.793 mmol) in the presence of EDCI hydrochloride (181 mg, 0.952 mmol), HOBt (32 mg, 0.238 mmol) and DMAP (9.6 mg, 0.079 mmol) in 1,2 dichloroethane (8 ml) to give 14 mg of the product as a white solid; ¹H NMR (300 MHz, CDCl₃): δ 3.48 (s, 3H), 3.50 (s, 3H), 4.00 (s, 3H), 4.16 (s, 2H), 7.18 (s, 2H), 7.42 (t, J=8.1 Hz, 1H), 7.70-7.80 (m, 2H), 11.24 (br s, 1H); ESI-MS (m/z): 495.06 (M+H)$^+$.

Example 50

N-[4-(2,4-Difluorophenyl)-1,3-thiazol-2-yl]-2-(2,5,7-trimethyl-4,6-dioxo-4,5,6,7-tetrahydro-2H-pyrazolo[3,4-d]pyrimidin-3-yl)acetamide

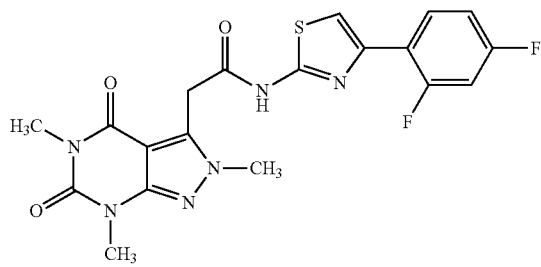 [SMILES: Cn1nc2c(c1CC(=O)Nc1nc(-c3ccc(F)cc3F)cs1)c(=O)n(C)c(=O)n2C]

The title compound was prepared according to the general procedure (Method B) by coupling Intermediate 8 (250 mg, 0.992 mmol) with 4-(2,4-difluorophenyl)-1,3-thiazol-2-amine (210 mg, 0.992 mmol) in the presence of EDCI hydrochloride (228 mg, 1.190 mmol), HOBt (40 mg, 0.297 mmol) and DMAP (12.12 mg, 0.099 mmol) in 1,2-dichloroethane (10 ml) to give 60 mg of the product as an off-white solid; $^1$H NMR (300 MHz, DMSO-d$_6$): δ 3.17 (s, 3H), 3.37 (s, 3H), 3.85 (s, 3H), 4.40 (s, 2H), 7.23 (t, J=8.4 Hz, 1H), 7.39 (t, J=9.0 Hz, 1H), 7.52 (s, 1H), 8.06 (q, J=8.7 Hz, 1H), 12.76 (br s, 1H); APCI-MS (m/z) 447.08 (M+H)$^+$.

Example 51

N-[4-(3,4-Difluorophenyl)-1,3-thiazol-2-yl]-2-(2,5,7-trimethyl-4,6-dioxo-4,5,6,7-tetrahydro-2H-pyrazolo[3,4-d]pyrimidin-3-yl)acetamide

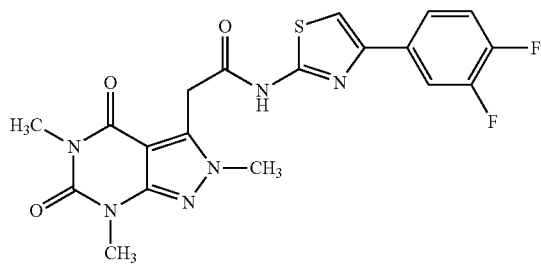 [SMILES: Cn1nc2c(c1CC(=O)Nc1nc(-c3ccc(F)c(F)c3)cs1)c(=O)n(C)c(=O)n2C]

The title compound was prepared according to the general procedure (Method B) by coupling Intermediate 8 (250 mg, 0.992 mmol) with 4-(3,4-difluorophenyl)-1,3-thiazol-2-amine (210 mg, 0.992 mmol) in the presence of EDCI hydrochloride (228 mg, 1.190 mmol), HOBt (40 mg, 0.297 mmol) and DMAP (12.12 mg, 0.099 mmol) in 1,2-dichloroethane (10 ml) to give 26 mg of the product as an off-white solid; $^1$H NMR (300 MHz, DMSO-d$_6$): δ 3.17 (s, 3H), 3.36 (s, 3H), 3.85 (s, 3H), 4.40 (s, 2H), 7.23 (d, J=9.0 Hz, 1H), 7.61 (d, J=7.5 Hz, 2H), 7.91 (s, 1H), 12.79 (br s, 1H); APCI-MS (m/z) 447.00 (M+H)$^+$.

Example 52

N-[4-(3,5-Difluorophenyl)-1,3-thiazol-2-yl]-2-(2,5,7-trimethyl-4,6-dioxo-4,5,6,7-tetrahydro-2H-pyrazolo[3,4-d]pyrimidin-3-yl)acetamide

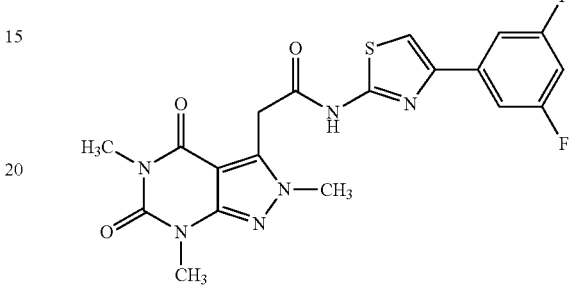

The title compound was prepared according to the general procedure (Method B) by coupling Intermediate 8 (250 mg, 0.992 mmol) with 4-(3,5-difluorophenyl)-1,3-thiazol-2-amine (210 mg, 0.992 mmol) in the presence of EDCI hydrochloride (228 mg, 1.190 mmol), HOBt (40 mg, 0.297 mmol) and DMAP (12.12 mg, 0.099 mmol) in 1,2-dichloroethane (10 ml) to give 36 mg of the product as an off-white solid; $^1$H NMR (300 MHz, DMSO-d$_6$): δ 3.17 (s, 3H), 3.36 (s, 3H), 3.85 (s, 3H), 4.40 (s, 2H), 7.23 (d, J=9.0 Hz, 1H), 7.61 (d, J=7.5 Hz, 2H), 7.91 (s, 1H), 12.79 (br s, 1H); APCI-MS (m/z) 447.00 (M+H)$^+$.

Example 53

N-{4-[4-Fluoro-3-(trifluoromethyl)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide

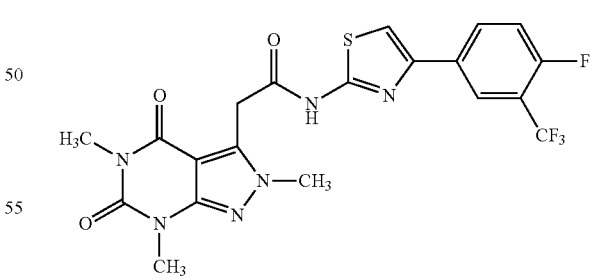

The title compound was prepared according to the general procedure (Method B) by coupling Intermediate 8 (250 mg, 0.992 mmol) with 4-[4-fluoro-3-(trifluoromethyl)phenyl]-1,3-thiazol-2-amine (260 mg, 0.992 mmol) in the presence of EDCI hydrochloride (228 mg, 1.190 mmol), HOBt (40 mg, 0.297 mmol) and DMAP (12.12 mg, 0.099 mmol) in 1,2-dichloroethane (10 ml) to give 45 mg of the product as an off-white solid; $^1$H NMR (300 MHz, DMSO-d$_6$): δ 3.17 (s, 3H), 3.37 (s, 3H), 3.85 (s, 3H), 4.39 (s, 2H), 7.62 (t, J=9.0 Hz, 1H), 7.88 (s, 1H), 8.24-8.30 (m, 2H), 12.80 (br s, 1H); APCI-MS (m/z) 497.05 (M+H)$^+$.

Example 54

N-[4-(3-Fluoro-4-trifluoromethylphenyl)-1,3-thiazol-2-yl]-2-(2,5,7-trimethyl-4,6-dioxo-4,5,6,7-tetrahydro-2H-pyrazolo[3,4-d]pyrimidin-3-yl)acetamide

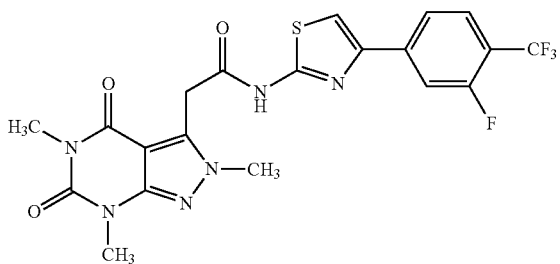 [SMILES: Cn1nc2c(c1CC(=O)Nc1nc(-c3ccc(C(F)(F)F)c(F)c3)cs1)c(=O)n(C)c(=O)n2C]

The title compound was prepared according to the general procedure (Method B) by coupling Intermediate 8 (250 mg, 0.992 mmol) with 4-(3-fluoro-4-trifluoromethylphenyl)-1,3-thiazol-2-amine (259 mg, 0.992 mmol) in the presence of EDCI hydrochloride (228 mg, 1.190 mmol), HOBt (40 mg, 0.297 mmol) and DMAP (12 mg, 0.099 mmol) in 1,2-dichloroethane (9.9 ml) to give 80 mg of the product as an off-white solid; $^1$H NMR (300 MHz, DMSO-d$_6$): δ 3.17 (s, 3H), 3.37 (s, 3H), 3.85 (s, 3H), 4.40 (s, 2H), 7.86-8.05 (m, 4H), 12.84 (br s, 1H); ESI-MS (m/z): 497.09 (M+H)$^+$.

Example 55

N-{4-[2-Fluoro-3-(trifluoromethyl)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide

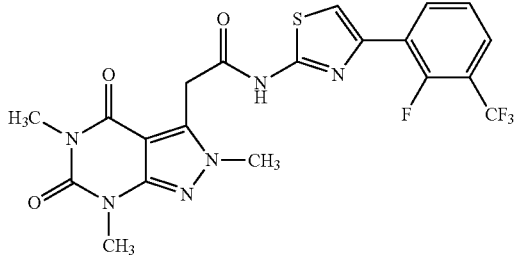 [SMILES: Cn1nc2c(c1CC(=O)Nc1nc(-c3cccc(C(F)(F)F)c3F)cs1)c(=O)n(C)c(=O)n2C]

The title compound was prepared according to the general procedure (Method B) by coupling Intermediate 8 (250 mg, 0.992 mmol) with 4-[2-fluoro-3-(trifluoromethyl)phenyl]-1,3-thiazol-2-amine (260 mg, 0.992 mmol) in the presence of EDCI hydrochloride (228 mg, 1.190 mmol), HOBt (40 mg, 0.297 mmol) and DMAP (12.12 mg, 0.099 mmol) in 1,2-dichloroethane (10 ml) to give 35 mg of the product as an off-white solid; $^1$H NMR (300 MHz, DMSO-d$_6$): δ 3.17 (s, 3H), 3.37 (s, 3H), 3.85 (s, 3H), 4.41 (s, 2H), 7.54 (t, J=7.8 Hz, 1H), 7.72 (s, 1H), 7.78 (t, J=6.9 Hz, 1H), 8.33 (t, J=7.5 Hz, 1H), 12.83 (br s, 1H); APCI-MS (m/z) 497.00 (M+H)$^+$.

Example 56

N-{4-[2-Fluoro-4-(trifluoromethyl)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide

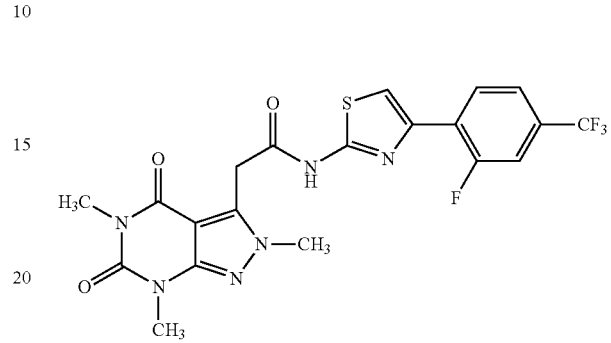

The title compound was prepared according to the general procedure (Method B) by coupling Intermediate 8 (250 mg, 0.992 mmol) with 4-[2-Fluoro-4-(trifluoromethyl)phenyl]-1,3-thiazol-2-amine (260 mg, 0.992 mmol) in the presence of EDCI hydrochloride (228 mg, 1.190 mmol), HOBt (40 mg, 0.297 mmol) and DMAP (12 mg, 0.099 mmol) in 1,2-dichloroethane (9.9 ml) to give 32 mg of the product as an off-white solid; $^1$H NMR (300 MHz, DMSO-d$_6$): δ 3.17 (s, 3H), 3.35 (s, 3H), 3.85 (s, 3H), 4.41 (s, 2H), 7.70-7.86 (m, 3H), 7.26 (t, J=7.8 Hz, 1H), 12.85 (br s, 1H); APCI-MS (m/z) 497.09 (M+H)$^+$.

Example 57

N-{4-[2-Fluoro-5-(trifluoromethyl)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide

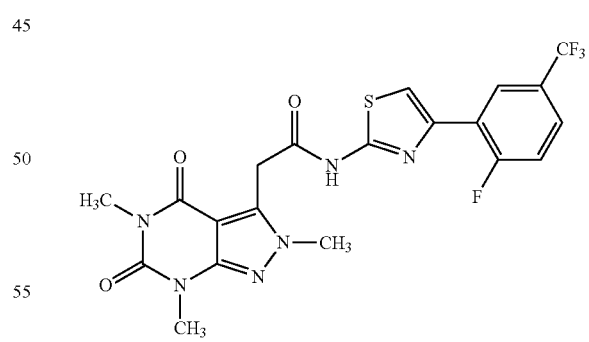

The title compound was prepared according to the general procedure (Method B) by coupling Intermediate 8 (250 mg, 0.992 mmol) with 4-[2-fluoro-5-(trifluoromethyl)phenyl]-1,3-thiazol-2-amine (260 mg, 0.992 mmol) in the presence of EDCI hydrochloride (228 mg, 1.190 mmol), HOBt (40 mg, 0.297 mmol) and DMAP (12.12 mg, 0.099 mmol) in 1,2-dichloroethane (10 ml) to give 80 mg of the product as an off-white solid; $^1$H NMR (300 MHz, DMSO-d$_6$): δ 3.17 (s, 3H), 3.37 (s, 3H), 3.85 (s, 3H), 4.40 (s, 2H), 7.56-7.65 (m, 1H), 7.72 (s, 1H), 7.76-7.82 (m, 1H), 8.38-8.44 (m, 1H), 12.84 (br s, 1H); APCI-MS (m/z) 497.10 (M+H)+.

Example 58

N-{4-[3-Fluoro-5-(trifluoromethyl)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide

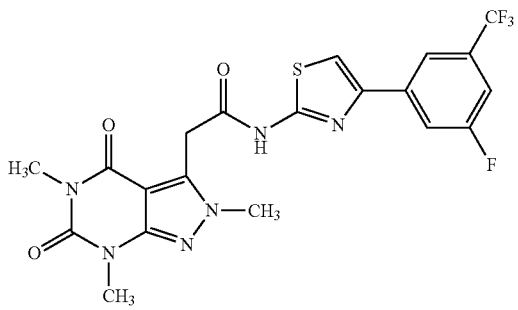 [SMILES: Cn1nc2c(c1CC(=O)Nc1nc(-c3cc(F)cc(C(F)(F)F)c3)cs1)c(=O)n(C)c(=O)n2C]

The title compound was prepared according to the general procedure (Method B) by coupling Intermediate 8 (250 mg, 0.992 mmol) with 4-[3-fluoro-5-(trifluoromethyl)phenyl]-1,3-thiazol-2-amine (275 mg, 0.992 mmol) in the presence of EDCI hydrochloride (228 mg, 1.19 mmol), HOBt (40 mg, 0.297 mmol) and DMAP (12 mg, 0.099 mmol) in 1,2 dichloroethane (8 ml) to give 12 mg of the product as a white solid; $^1$H NMR (300 MHz, DMSO-$d_6$): δ 3.17 (s, 3H), 3.36 (s, 3H), 3.85 (s, 3H), 4.39 (s, 2H), 7.61 (t, J=9.9 Hz, 1H), 7.82 (s, 1H), 8.00-8.06 (m, 2H), 12.78 (br s, 1H); APCI-MS (m/z) 513.11 (M+H)+.

Example 59

N-{4-[3-Fluoro-4-(trifluoromethoxy)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide

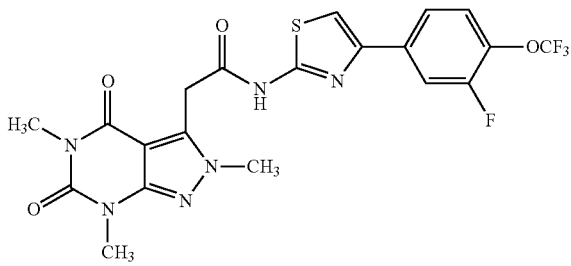 [SMILES: Cn1nc2c(c1CC(=O)Nc1nc(-c3ccc(OC(F)(F)F)c(F)c3)cs1)c(=O)n(C)c(=O)n2C]

The title compound was prepared according to the general procedure (Method B) by coupling Intermediate 8 (200 mg, 0.793 mmol) with 4-[3-fluoro-4-(trifluoromethoxy)phenyl]-1,3-thiazol-2-amine (220 mg, 0.793 mmol) in the presence of EDCI hydrochloride (181 mg, 0.952 mmol), HOBt (32 mg, 0.238 mmol) and DMAP (9.6 mg, 0.079 mmol) in 1,2 dichloroethane (8 ml) to give 16 mg of the product as a white solid; $^1$H NMR (300 MHz, CDCl$_3$): δ 3.49, 3.50 (2s, 6H), 4.01 (s, 3H), 4.15 (s, 2H), 7.15 (s, 1H), 7.27-7.35 (m, 1H), 7.61 (d, J=8.1 Hz, 1H), 7.67-7.73 (m, 1H), 11.18 (br s, 1H); ESI-MS (m/z): 495.06 (M+H)+.

Example 60

N-{4-[4-Fluoro-3-(trifluoromethoxy)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide

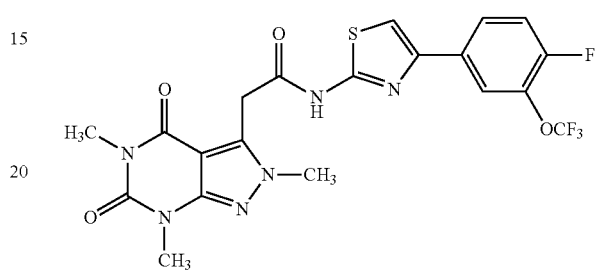

The title compound was prepared according to the general procedure (Method B) by coupling Intermediate 8 (250 mg, 0.992 mmol) with 4-[4-fluoro-3-(trifluoromethoxy)phenyl]-1,3-thiazol-2-amine (275 mg, 0.992 mmol) in the presence of EDCI hydrochloride (228 mg, 1.190 mmol), HOBt (40 mg, 0.297 mmol) and DMAP (12.12 mg, 0.099 mmol) in 1,2-dichloroethane (10 ml) to give 90 mg of the product as an off-white solid; $^1$H NMR (300 MHz, DMSO-$d_6$): δ 3.17 (s, 3H), 3.36 (s, 3H), 3.85 (s, 3H), 4.39 (s, 2H), 7.61 (t, J=8.7 Hz, 1H), 7.82 (s, 1H), 8.00-8.07 (m, 2H), 12.78 (br s, 1H); APCI-MS (m/z) 513.11 (M+H)+.

Example 61

N-{4-[4-(Difluoromethoxy)-3-fluorophenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide

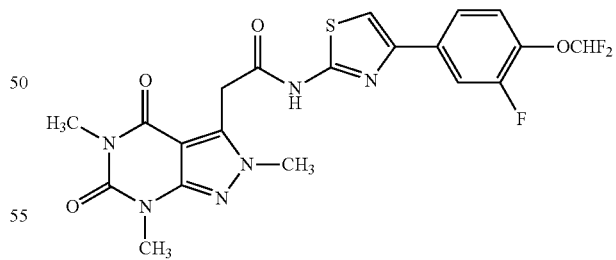

The title compound was prepared according to the general procedure (Method B) by coupling Intermediate 8 (250 mg, 0.992 mmol) with 4-[4-(difluoromethoxy)-3-fluorophenyl]-1,3-thiazol-2-amine (258 mg, 0.992 mmol) in the presence of EDCI hydrochloride (228 mg, 1.190 mmol), HOBt (40 mg, 0.297 mmol) and DMAP (12.12 mg, 0.099 mmol) in 1,2-dichloroethane (10 ml) to give 40 mg of the product as an off-white solid; $^1$H NMR (300 MHz, DMSO-$d_6$): δ 3.17 (s, 3H), 3.37 (s, 3H), 3.85 (s, 3H), 4.39 (s, 2H), 7.29 (t, J=72.9

Hz, 1H), 7.45 (t, J=8.4 Hz, 1H), 7.78 (s, 2H), 7.86-7.92 (m, 1H), 12.77 (br s, 1H); ESI-MS (m/z) 495.08 (M+H)$^+$.

Example 62

N-{4-[2,3-difluoro-4-(trifluoromethyl)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide

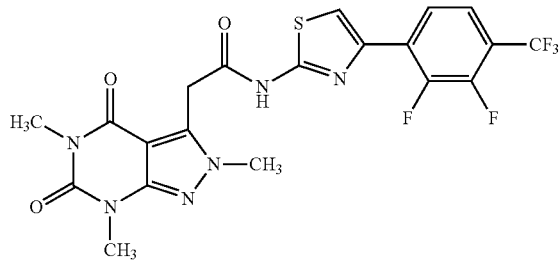

The title compound was prepared according to the general procedure (Method B) by coupling Intermediate 8 (250 mg, 0.992 mmol) with 4-[2,3-difluoro-4-(trifluoromethyl)phenyl]-1,3-thiazol-2-amine (277 mg, 0.992 mmol) in the presence of EDCI hydrochloride (228 mg, 1.190 mmol), HOBt (40 mg, 0.297 mmol) and DMAP (12.12 mg, 0.099 mmol) in 1,2-dichloroethane (10 ml) to give 53 mg of the product as an off-white solid; $^1$H NMR (300 MHz, DMSO-d$_6$): δ 3.17 (s, 3H), 3.33 (s, 3H), 3.85 (s, 3H), 4.41 (s, 2H), 7.72-7.79 (m, 1H), 7.84 (s, 1H), 7.99-8.05 (m, 1H), 12.87 (br s, 1H); ESI-MS (m/z) 515.10 (M+H)

Example 63

N-{4-[2,4-Difluoro-3-(trifluoromethyl)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide

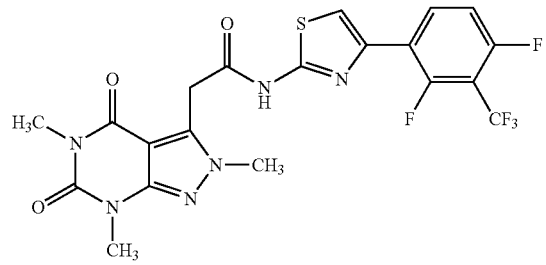

The title compound was prepared according to the general procedure (Method B) by coupling Intermediate 8 (250 mg, 0.992 mmol) with 4-[2,4-difluoro-3-(trifluoromethyl)phenyl]-1,3-thiazol-2-amine (279 mg, 0.992 mmol) in the presence of EDCI hydrochloride (228 mg, 1.190 mmol), HOBt (40 mg, 0.297 mmol) and DMAP (9.69 mg, 0.099 mmol) in 1,2-dichloroethane (8 ml) to give 122 mg of the product as an off-white solid; $^1$H NMR (300 MHz, DMF-d$_7$): δ 3.22 (s, 3H), 3.42 (s, 3H), 3.97 (s, 3H), 4.58 (s, 2H), 7.52 (t, J=8.4 Hz, 1H), 7.71 (s, 1H), 8.43 (q, J=9.0 Hz, 1H), 12.80 (br s, 1H); APCI-MS (m/z) 515.07 (M+H)$^+$.

Example 64

N-{4-[4-(Difluoromethoxy)-3,5-difluorophenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide

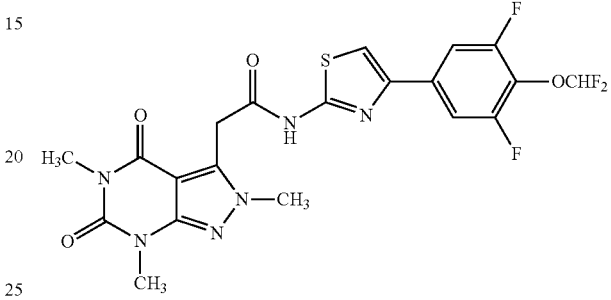

The title compound was prepared according to the general procedure (Method B) by coupling Intermediate 8 (250 mg, 0.992 mmol) with 4-[4-(Difluoromethoxy)-3,5-difluorophenyl]-1,3-thiazol-2-amine (273 mg, 0.992 mmol) in the presence of EDCI hydrochloride (228 mg, 1.190 mmol), HOBt (40 mg, 0.297 mmol) and DMAP (12 mg, 0.099 mmol) in 1,2-dichloroethane (9.9 ml) to give 40 mg of the product as an off-white solid; $^1$H NMR (300 MHz, DMSO-d$_6$) δ 3.17 (s, 3H), 3.36 (s, 3H), 3.85 (s, 3H), 4.40 (s, 2H), 7.28 (t, J=72.3 Hz, 1H), 7.80 (d, J=9.0 Hz, 2H), 7.91 (s, 1H), 12.80 (br s, 1H); APCI-MS (m/z) 513.00 (M+H)$^+$.

Example 65

N-[5-(4-Bromophenyl)isoxazol-3-yl]-2-(2,5,7-trimethyl-4,6-dioxo-4,5,6,7-tetrahydro-2H-pyrazolo[3,4-d]pyrimidin-3-yl)acetamide

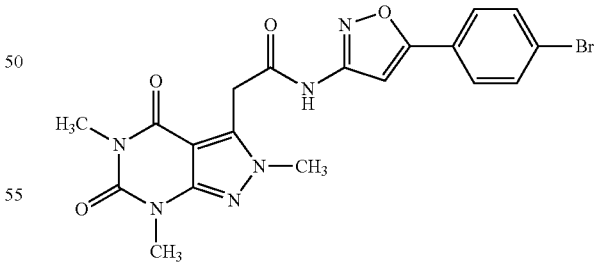

The title compound was prepared according to the general procedure (Method B) by coupling Intermediate 8 (250 mg, 0.992 mmol) with 5-(4-bromophenyl)isoxazol-3-amine (237 mg, 0.992 mmol) in the presence of EDCI hydrochloride (228 mg, 1.190 mmol), HOBt (40 mg, 0.297 mmol) and DMAP (12.12 mg, 0.099 mmol) in 1,2-dichloroethane (10 ml) to give 30 mg of the product as an off-white solid; $^1$H NMR (300 MHz, DMSO-d$_6$): δ 3.18 (s, 3H), 3.34 (s, 3H), 3.84 (s, 3H), 4.33 (s, 2H), 7.35 (s, 1H), 7.73 (d, J=8.1 Hz, 2H), 7.83 (d, J=8.7 Hz, 2H), 11.58 (br s, 1H); APCI-MS (m/z) 473.05 (M+H)$^+$.

Example 66

N-[5-(Trifluoromethoxy)-1,3-benzothiazol-2-yl]-2-(2,5,7-trimethyl-4,6-dioxo-4,5,6,7-tetrahydro-2H-pyrazolo[3,4-d]pyrimidin-3-yl)acetamide

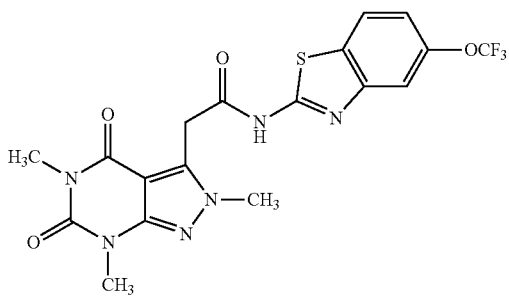 [SMILES: Cn1nc2c(c1CC(=O)Nc1nc3cc(OC(F)(F)F)ccc3s1)c(=O)n(C)c(=O)n2C]

The title compound was prepared according to the general procedure (Method B) by coupling Intermediate 8 (250 mg, 0.992 mmol) with 5-(trifluoromethoxy)-1,3-benzothiazol-2-amine (234 mg, 0.992 mmol) in the presence of EDCI hydrochloride (458 mg, 2.389 mmol), HOBt (40 mg, 0.297 mmol) and DMAP (12.12 mg, 0.099 mmol) in 1,2-dichloroethane (10 ml) to give 200 mg of the product as an off-white solid; $^1$H NMR (300 MHz, DMSO-d$_6$): δ 3.17 (s, 3H), 3.37 (s, 3H), 3.86 (s, 3H), 4.45 (s, 2H), 7.44 (d, J=8.7 Hz, 1H), 7.86 (d, J=8.7 Hz, 1H), 8.13 (s, 1H), 12.94 (br s, 1H); APCI-MS (m/z) 469.10 (M+H)$^+$.

Example 67

N-[4-(4-Chlorophenyl)-1,3-thiazol-2-yl]-2-(4,6-dimethyl-5,7-dioxo-4,5,6,7-tetrahydro-1H-pyrazolo[4,3-d]pyrimidin-1-yl)acetamide

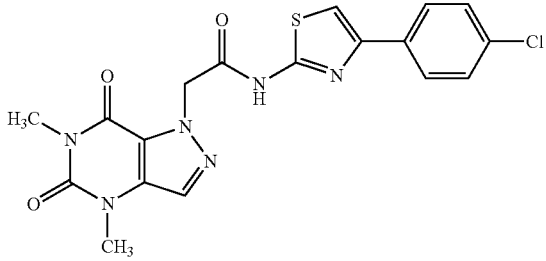 [SMILES: Cn1c(=O)c2c(cnn2CC(=O)Nc2nc(-c3ccc(Cl)cc3)cs2)n(C)c1=O]

The title compound was prepared according to the general procedure (Method A) by coupling Intermediate 9 (150 mg, 0.823 mmol) with 2-bromo-N-[4-(4-chlorophenyl)-1,3-thiazol-2-yl]acetamide (328 mg, 0.988 mmol) in the presence of NaH (50 mg, 1.235 mmol) in dry DMF (3.0 mL) to give 30 mg of the product as an off-white solid; $^1$H NMR (300 MHz, DMSO-d$_6$): δ 3.22 (s, 3H), 3.44 (s, 3H), 5.50 (s, 2H), 7.51 (d, J=8.1 Hz, 2H), 7.73 (s, 1H), 7.89 (s, 1H), 7.93 (d, J=8.4 Hz, 2H), 12.77 (br s, 1H); APCI-MS (m/z): 431.09 (M+H)$^+$.

Example 68

2-(4,6-Dimethyl-5,7-dioxo-4,5,6,7-tetrahydro-1H-pyrazolo[4,3-d]pyrimidin-1-yl)-N-{4-[3-fluoro-4-(trifluoromethyl)phenyl]-1,3-thiazol-2-yl}acetamide

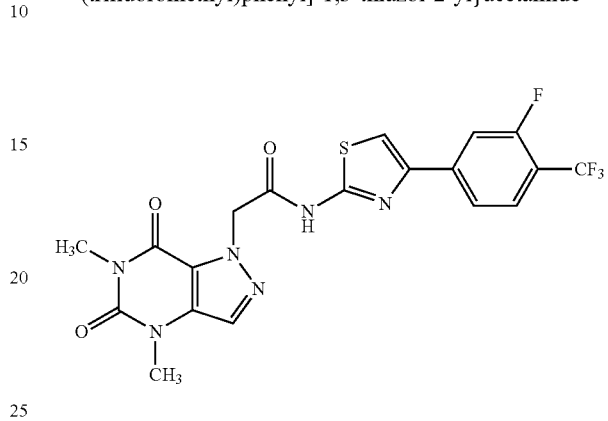

The title compound was prepared according to the general procedure (Method A) by coupling Intermediate 9 (62 mg, 0.344 mmol) with 2-bromo-N-{4-[3-fluoro-4-(trifluoromethyl)phenyl]-1,3-thiazol-2-yl}acetamide (110 mg, 0.287 mmol) in the presence of NaH (17 mg, 0.430 mmol) in dry DMF (5.0 mL) to give 35 mg of the product as an off-white solid; $^1$H NMR (300 MHz, DMSO-d$_6$) δ 3.21 (s, 3H), 3.43 (s, 3H), 5.51 (s, 2H), 7.84-8.02 (m, 5H), 12.85 (br s, 1H); APCI-MS (m/z) 481.22 (M–H)$^-$.

Example 69

N-{4-[4-(2,2-Dimethylpropoxy)-3-fluorophenyl]-1,3-thiazol-2-yl}-2-(4,6-dimethyl-5,7-dioxo-4,5,6,7-tetrahydro-1H-pyrazolo[4,3-d]pyrimidin-1-yl)acetamide

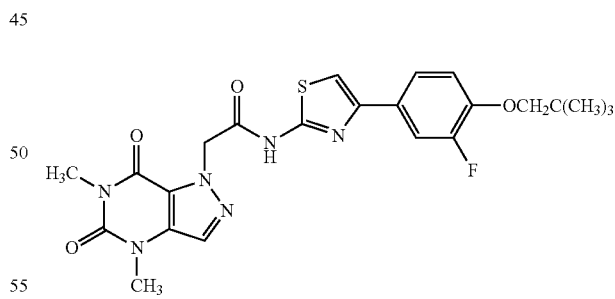

The title compound was prepared according to the general procedure (Method A) by coupling Intermediate 9 (60 mg, 0.333 mmol) with 2-bromo-N-{4-[4-(2,2-dimethylpropoxy)-3-fluorophenyl]-1,3-thiazol-2-yl}acetamide (107 mg, 0.277 mmol) in the presence of NaH (17 mg, 0.415 mmol) in dry DMF (5.0 mL) to give 50 mg of the product as an off-white solid; $^1$H NMR (300 MHz, DMSO-d$_6$) δ 1.02 (s, 9H), 3.22 (s, 3H), 3.44 (s, 3H), 3.75 (s, 2H), 5.49 (s, 2H), 7.22 (t, J=8.4 Hz, 1H), 7.61 (s, 1H), 7.65-7.75 (m, 2H), 7.89 (s, 1H), 12.72 (br s, 1H); APCI-MS (m/z) 501.45 (M+H)$^+$.

Example 70

N-{4-[3-Chloro-4-(2,2-dimethylpropoxy)phenyl]-1,3-thiazol-2-yl}-2-(4,6-dimethyl-5,7-dioxo-4,5,6,7-tetrahydro-1H-pyrazolo[4,3-d]pyrimidin-1-yl)acetamide

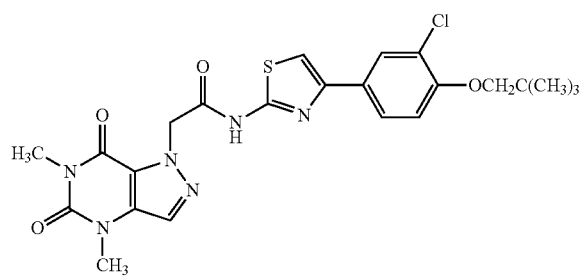

The title compound was prepared according to the general procedure (Method A) by coupling Intermediate 9 (60 mg, 0.333 mmol) with 2-bromo-N-{4-[3-chloro-4-(2,2-dimethylpropoxy)phenyl]-1,3-thiazol-2-yl}acetamide (167 mg, 0.399 mmol) in the presence of NaH (20 mg, 0.499 mmol) in dry DMF (5.0 mL) to give 35 mg of the product as an off-white solid; $^1$H NMR (300 MHz, DMSO-$d_6$) δ 1.04 (s, 9H), 3.22 (s, 3H), 3.43 (s, 3H), 3.76 (s, 2H), 5.49 (s, 2H), 7.19 (d, J=8.7 Hz, 1H), 7.63 (s, 1H), 7.81 (d, J=8.7 Hz, 1H), 7.88 (s, 1H), 7.95 (s, 1H), 12.72 (br s, 1H); APCI-MS (m/z) 517.17 (M+H)$^+$.

Example 71

N-{4-[2,4-Difluoro-3-(trifluoromethyl)phenyl]-1,3-thiazol-2-yl}-2-(4,6-dimethyl-5,7-dioxo-4,5,6,7-tetrahydro-1H-pyrazolo[4,3-d]pyrimidin-1-yl)acetamide

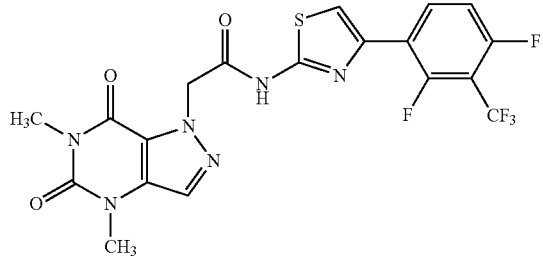 [SMILES: Cn1c(=O)c2c(cnn2CC(=O)Nc2nc(-c3ccc(F)c(C(F)(F)F)c3F)cs2)n(C)c1=O]

The title compound was prepared according to the general procedure (Method A) by coupling with Intermediate 9 (100 mg, 0.600 mmol) with 2-bromo-N-{4-[2,4-difluoro-3-(trifluoromethyl)phenyl]-1,3-thiazol-2-yl}acetamide (289 mg, 0.720 mmol) in the presence of NaH (36 mg, 0.900 mmol) in dry DMF (3.0 mL) to give 38 mg of the product as an off-white solid; $^1$H NMR (300 MHz, DMSO-$d_6$): δ 3.22 (s, 3H), 3.44 (s, 3H), 5.51 (s, 2H), 7.53 (t, J=9.9 Hz, 1H), 7.69 (s, 1H), 7.89 (s, 1H), 8.30-8.38 (m, 1H), 12.84 (br s, 1H); APCI-MS (m/z): 501.24 (M+H)$^+$.

Example 72

N-{4-[4-(Difluoromethoxy)-3,5-difluorophenyl]-1,3-thiazol-2-yl}-2-(4,6-dimethyl-5,7-dioxo-4,5,6,7-tetrahydro-1H-pyrazolo[4,3-d]pyrimidin-1-yl)acetamide

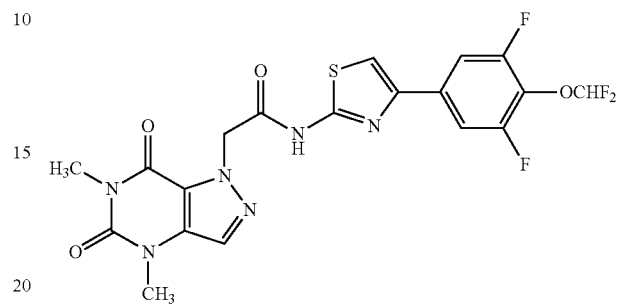

The title compound was prepared according to the general procedure (Method A) by coupling with Intermediate 9 (60 mg, 0.331 mmol) with 2-bromo-N-{4-[4-(difluoromethoxy)-3,5-difluorophenyl]-1,3-thiazol-2-yl}acetamide (110 mg, 0.276 mmol) in the presence of NaH (17 mg, 0.414 mmol) in dry DMF (5.0 mL) to give 40 mg of the product as an off-white solid; $^1$H NMR (300 MHz, DMSO-$d_6$) δ 3.22 (s, 3H), 3.43 (s, 3H), 5.50 (s, 2H), 7.28 (t, J=72.3 Hz, 1H), 7.80 (d, J=9.3 Hz, 1H), 7.89 (s, 1H), 7.92 (s, 1H), 12.82 (br s, 1H); APCI-MS (m/z) 499.20 (M+H)$^+$.

Example 73

N-{4-[3,5-Difluoro-4-(2,2,2-trifluoroethoxy)phenyl]-1,3-thiazol-2-yl}-2-(4,6-dimethyl-5,7-dioxo-4,5,6,7-tetrahydro-1H-pyrazolo[4,3-d]pyrimidin-1-yl)acetamide

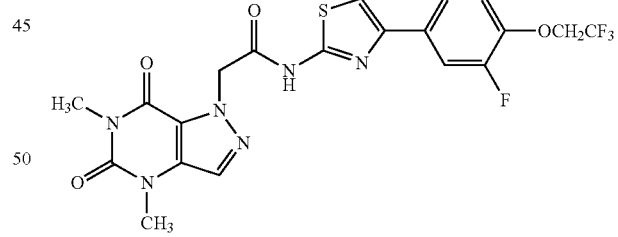

The title compound was prepared according to the general procedure (Method A) by coupling Intermediate 9 (130 mg, 0.700 mmol) with 2-bromo-N-[4-(3,5-Difluoro-4-(2,2,2-trifluoroethoxy)phenyl)-1,3-thiazol-2-yl]acetamide (302 mg, 0.700 mmol) in the presence of NaH (42 mg, 1.050 mmol) in dry DMF (3.0 mL) to give 73 mg of the product as a white solid; $^1$H NMR (300 MHz, DMSO-$d_6$): δ 3.21 (s, 3H), 3.43 (s, 3H), 4.86 (q, J=9.0 Hz, 2H), 5.50 (s, 2H), 7.71 (d, J=9.9 Hz, 2H), 7.85 (s, 1H), 7.89 (s, 1H), 12.80 (br s, 1H); APCI-MS (m/z): 531.11 (M+H)$^+$.

Further eluting gave 30 mg of N-[4-(3,5-Difluoro-4-(2,2,2-trifluoroethoxy)phenyl]-1,3-thiazol-2-yl]-2-(4,6-dimethyl-5,7-dioxo-4,5,6,7-tetrahydro-2H-pyrazolo[4,3-d]pyrimidin-2-yl)acetamide; $^1$H NMR (300 MHz, DMSO-$d_6$): δ 3.26 (s, 3H), 3.36 (s, 3H), 4.86 (q, J=9.0 Hz, 2H), 5.38 (s, 2H), 7.70 (d, J=8.7 Hz, 2H), 7.88 (s, 1H), 8.08 (s, 1H), 12.85 (br s, 1H); APCI-MS (m/z) 529.10 (M−H)$^-$.

Example 74

N-[4-(3,5-Difluoro-4-isobutoxyphenyl)-1,3-thiazol-2-yl]-2-(4,6-dimethyl-5,7-dioxo-4,5,6,7-tetrahydro-1H-pyrazolo[4,3-d]pyrimidin-1-yl)acetamide

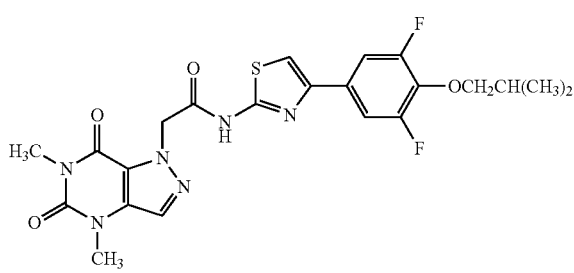

The title compound was prepared according to the general procedure (Method A) by coupling with Intermediate 9 (60 mg, 0.333 mmol) with 2-bromo-N-{4-(3,5-difluoro-4-isobutoxyphenyl)-1,3-thiazol-2-yl}acetamide (162 mg, 0.399 mmol) in the presence of NaH (20 mg, 0.499 mmol) in dry DMF (5.0 mL) to give 25 mg of the product as an off-white solid; $^1$H NMR (300 MHz, DMSO-$d_6$) δ 0.98 (d, J=6.9 Hz, 6H), 1.98-2.04 (m, 1H), 3.22 (s, 3H), 3.43 (s, 3H), 3.91 (d, J=6.6 Hz, 2H), 5.50 (s, 2H), 7.62-7.68 (m, 2H), 7.79 (s, 1H), 7.89 (s, 1H), 12.77 (br s, 1H); APCI-MS (m/z) 505.13 (M+H)$^+$.

Example 75

N-[4-(3,5-Dichloro-4-isobutoxyphenyl)-1,3-thiazol-2-yl]-2-(4,6-dimethyl-5,7-dioxo-4,5,6,7-tetrahydro-1H-pyrazolo[4,3-d]pyrimidin-1-yl)acetamide

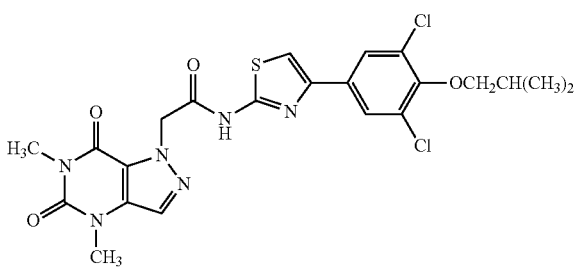

The title compound was prepared according to the general procedure (Method A) by coupling with Intermediate 9 (60 mg, 0.333 mmol) with 2-bromo-N-{4-(3,5-dichloro-4-isobutoxyphenyl)-1,3-thiazol-2-yl}acetamide (175 mg, 0.399 mmol) in the presence of NaH (20 mg, 0.499 mmol) in dry DMF (5.0 mL) to give 45 mg of the product as an off-white solid; $^1$H NMR (300 MHz, DMSO-$d_6$) δ 1.05 (d, J=6.6 Hz, 6H), 2.05-2.15 (m, 1H), 3.25 (s, 3H), 3.35 (s, 3H), 3.79 (d, J=6.0 Hz, 2H), 5.37 (s, 2H), 7.90 (s, 1H), 8.00 (s, 2H), 8.08 (s, 1H), 12.84 (br s, 1H); APCI-MS (m/z) 505.13 (M+H)$^+$.

Example 76

N-{4-[3,5-Difluoro-4-(3-methylbutoxy)phenyl]-1,3-thiazol-2-yl}-2-(4,6-dimethyl-5,7-dioxo-4,5,6,7-tetrahydro-1H-pyrazolo[4,3-d]pyrimidin-1-yl)acetamide

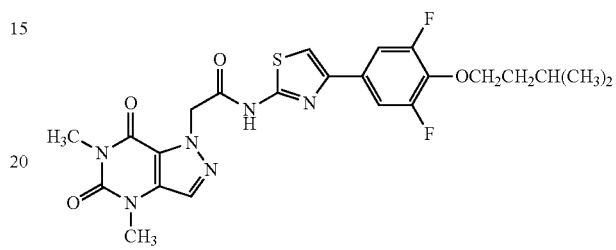

The title compound was prepared according to the general procedure (Method A) by coupling with Intermediate 9 (50 mg, 0.286 mmol) with 2-bromo-N-{4-[3,5-difluoro-4-(3-methylbutoxy)phenyl]-1,3-thiazol-2-yl}acetamide (100 mg, 0.238 mmol) in the presence of NaH (14 mg, 0.357 mmol) in dry DMF (5.0 mL) to give 35 mg of the product as an off-white solid; $^1$H NMR (300 MHz, DMSO-$d_6$) δ 0.92 (d, J=6.9 Hz, 6H), 1.55-1.62 (m, 2H), 1.76-1.86 (m, 1H), 3.22 (s, 3H), 3.43 (s, 3H), 4.15 (t, J=6.6 Hz, 2H), 5.50 (s, 2H), 7.62-7.68 (m, 2H), 7.79 (s, 1H), 7.89 (s, 1H), 12.77 (br s, 1H); APCI-MS (m/z) 519.18 (M+H)$^+$.

Example 77

N-{4-[3,5-Dichloro-4-isobutoxyphenyl]-1,3-thiazol-2-yl}-2-(4,6-dimethyl-5,7-dioxo-4,5,6,7-tetrahydro-1H-pyrazolo[4,3-d]pyrimidin-1-yl)acetamide

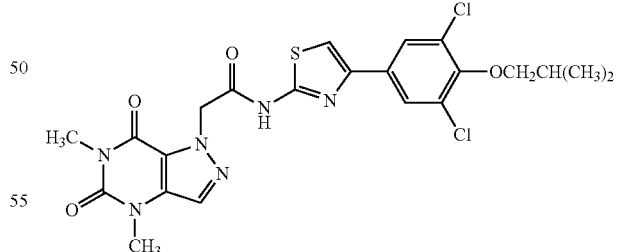

The title compound was prepared according to the general procedure (Method A) by coupling with Intermediate 9 (60 mg, 0.333 mmol) with 2-bromo-N-[4-(3,5-dichloro-4-isobutoxyphenyl)-1,3-thiazol-2-yl]acetamide (180 mg, 0.399 mmol) in the presence of NaH (20 mg, 0.499 mmol) in dry DMF (5.0 mL) to give 45 mg of the product as an off-white solid; $^1$H NMR (300 MHz, DMSO-$d_6$) δ 0.96 (d, J=6.9 Hz, 6H), 1.64-1.73 (m, 2H), 1.83-1.92 (m, 1H), 3.25 (s, 3H), 3.36

(s, 3H), 4.04 (t, J=6.6 Hz, 2H), 5.37 (s, 2H), 7.90 (s, 1H), 8.01 (s, 2H), 8.07 (s, 1H), 12.84 (br s, 1H); APCI-MS (m/z) 551.24 (M+H)⁺.

Example 78

N-{4-[4-(2,2-Dimethylpropoxy)-3,5-difluorophenyl]-1,3-thiazol-2-yl}-2-(4,6-dimethyl-5,7-dioxo-4,5,6,7-tetrahydro-1H-pyrazolo[4,3-d]pyrimidin-1-yl)acetamide

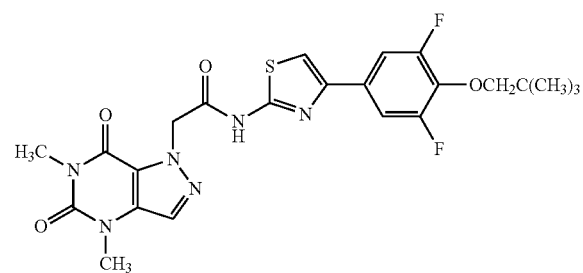

The title compound was prepared according to the general procedure (Method A) by coupling Intermediate 9 (150 mg, 0.800 mmol) with 2-bromo-N-[4-(2,2-dimethylpropoxy)-3,5-difluorophenyl)-1,3-thiazol-2-yl]acetamide (400 mg, 0.96 mmol) in the presence of NaH (48 mg, 1.20 mmol) in dry DMF (3.0 mL) to give 52 mg of the product as an off-white solid; $^1$H NMR (300 MHz, DMSO-$d_6$): δ 3.22 (s, 3H), 3.43 (s, 3H), 3.80 (s, 2H), 5.50 (s, 2H), 7.65 (d, J=9.3 Hz, 2H), 7.79 (s, 1H), 7.89 (s, 1H), 12.78 (br s, 1H); APCI-MS (m/z): 519.14 (M+H)⁺.

Example 79

N-{4-[3,5-Dichloro-4-(2,2-dimethylpropoxy)phenyl]-1,3-thiazol-2-yl}-2-(4,6-dimethyl-5,7-dioxo-4,5,6,7-tetrahydro-1H-pyrazolo[4,3-d]pyrimidin-1-yl)acetamide

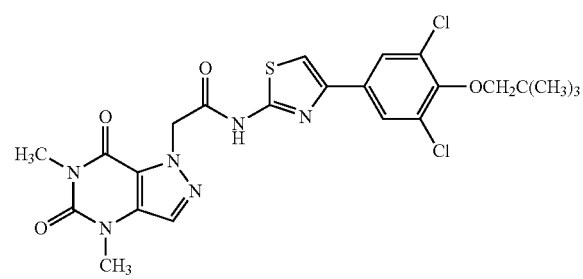

The title compound was prepared according to the general procedure (Method A) by coupling with Intermediate 9 (80 mg, 0.444 mmol) with 2-bromo-N-{4-[3,5-dichloro-4-(2,2-dimethylpropoxy)phenyl]-1,3-thiazol-2-yl}acetamide (219 mg, 0.488 mmol) in the presence of NaH (27 mg, 0.666 mmol) in dry DMF (5.0 mL) to give 65 mg of the product as an off-white solid; $^1$H NMR (300 MHz, DMSO-$d_6$) δ 1.08 (s, 9H), 3.22 (s, 3H), 3.43 (s, 3H), 3.67 (s, 2H), 5.50 (s, 2H), 7.85-7.91 (m, 2H), 8.00 (s, 2H), 12.77 (br s, 1H); APCI-MS (m/z) 551.16 (M+H)⁺.

Example 80

N-{4-[3-Chloro-4-(2,2-dimethylpropoxy)-5-fluorophenyl]-1,3-thiazol-2-yl}-2-(4,6-dimethyl-5,7-dioxo-4,5,6,7-tetrahydro-1H-pyrazolo[4,3-d]pyrimidin-1-yl)acetamide

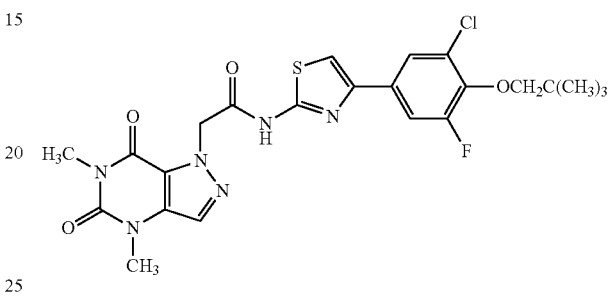

The title compound was prepared according to the general procedure (Method A) by coupling Intermediate 9 (70 mg, 0.389 mmol) with 2-bromo-N-{4-[3-chloro-4-(2,2-dimethylpropoxy)-5-fluorophenyl]-1,3-thiazol-2-yl}acetamide (203 mg, 0.466 mmol) in the presence of NaH (23 mg, 0.586 mmol) in dry DMF (5.0 mL) to give 40 mg of the product as an off-white solid; $^1$H NMR (300 MHz, DMSO-$d_6$) δ 1.04 (s, 9H), 3.21 (s, 3H), 3.43 (s, 3H), 3.78 (s, 2H), 5.49 (s, 2H), 7.75-7.91 (m, 4H), 12.77 (br s, 1H); APCI-MS (m/z) 535.23 (M+H)⁺.

Example 81

N-{4-[4-(Cyclobutylmethoxy)-3,5-difluorophenyl]-1,3-thiazol-2-yl}-2-(4,6-dimethyl-5,7-dioxo-4,5,6,7-tetrahydro-1H-pyrazolo[4,3-d]pyrimidin-1-yl)acetamide

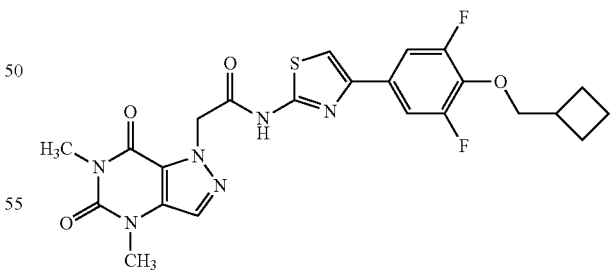

The title compound was prepared according to the general procedure (Method A) by coupling Intermediate 9 (100 mg, 0.555 mmol) with 2-bromo-N-{4-[4-(cyclobutylmethoxy)-3,5-difluorophenyl]-1,3-thiazol-2-yl}acetamide (278 mg, 0.666 mmol) in the presence of NaH (33 mg, 0.832 mmol) in dry DMF (5.0 mL) to give 55 mg of the product as an off-white solid; $^1$H NMR (300 MHz, DMSO-$d_6$) δ 1.78-1.92 (m, 4H), 2.00-2.06 (m, 2H), 2.65-2.72 (m, 1H), 3.22 (s, 3H), 3.43

(s, 3H), 4.10 (d, J=6.9 Hz, 2H), 5.50 (s, 2H), 7.62-7.68 (m, 2H), 7.79 (s, 1H), 7.89 (s, 1H), 12.77 (br s, 1H); APCI-MS (m/z) 517.15 (M+H)⁺.

Example 82

N-[4-(3,5-Difluoro-4-(2,2-dimethylprop oxy)phenyl)-1,3-thiazol-2-yl]-2-(3,4,6-trimethyl-5,7-dioxo-4,5,6,7-tetrahydro-1H-pyrazolo[4,3-d]pyrimidin-1-yl)acetamide

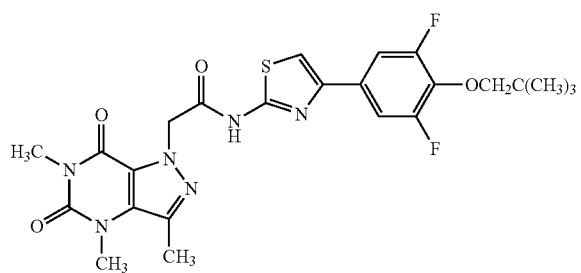

The title compound was prepared according to the general procedure (Method A) by coupling Intermediate 10 (50 mg, 0.257 mmol) with 2-bromo-N-[4-(3,5-difluoro-4-(2,2-dimethylpropoxy)phenyl)]-1,3-thiazol-2-yl}acetamide (118 mg, 0.283 mmol) in the presence of NaH (12 mg, 0.308 mmol) in dry DMF (5.0 mL) to give 19 mg of the product as an off-white solid; ¹H NMR (300 MHz, DMSO-d₆) δ 1.01 (s, 9H), 2.50 (s, 3H), 3.21 (s, 3H), 3.58 (s, 3H), 3.80 (s, 2H), 5.41 (s, 2H), 7.64 (d, J=9.3 Hz, 2H), 7.87 (s, 1H), 12.74 (br s, 1H); APCI-MS (m/z) 533.16 (M+H)⁺.

Example 83

N-[4-(3,5-Dichloro-4-(2,2-dimethylpropoxy)phenyl)-1,3-thiazol-2-yl]-2-(3,4,6-trimethyl-5,7-dioxo-4,5,6,7-tetrahydro-1H-pyrazolo[4,3-d]pyrimidin-1-yl)acetamide

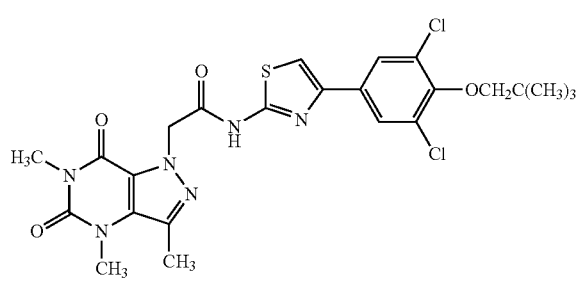

The title compound was prepared according to the general procedure (Method A) by coupling Intermediate 10 (50 mg, 0.257 mmol) with 2-bromo-N-[4-(3,5-dichloro-4-(2,2-dimethylpropoxy)phenyl)]-1,3-thiazol-2-yl}acetamide (127 mg, 0.283 mmol) in the presence of NaH (15 mg, 0.385 mmol) in dry DMF (5.0 mL) to give 25 mg of the product as an off-white solid; ¹H NMR (300 MHz, DMSO-d₆) δ 1.07 (s, 9H), 2.50 (s, 3H), 3.21 (s, 3H), 3.58 (s, 3H), 3.67 (s, 2H), 5.42 (s, 2H), 7.87 (s, 1H), 8.00 (s, 2H), 12.74 (br s, 1H); APCI-MS (m/z) 565.32 (M+H)⁺.

Example 84

N-[5-(4-Bromophenyl)isoxazol-3-yl]-2-(4,6-dimethyl-5,7-dioxo-4,5,6,7,-tetrahydro-1H-pyrazolo[4,3-d]pyrimidin-1-yl)acetamide

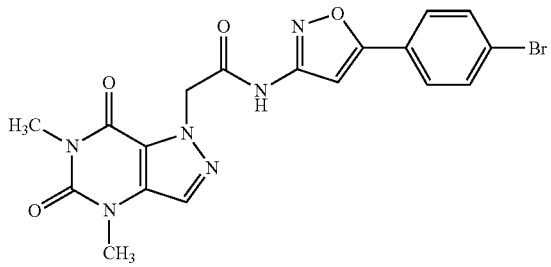 [SMILES: Cn1c(=O)c2c(cnn2CC(=O)Nc2cc(-c3ccc(Br)cc3)on2)n(C)c1=O]

The title compound was prepared according to the general procedure (Method A) by coupling Intermediate 9 (60 mg, 0.333 mmol) with 2-bromo-N-[5-(4-bromophenyl)isoxazol-3-yl]acetamide (144 mg, 0.399 mmol) in the presence of NaH (20 mg, 0.499 mmol) in dry DMF (5.0 mL) to give 40 mg of the product as an off-white solid; ¹H NMR (300 MHz, DMSO-d₆) δ 3.22 (s, 3H), 3.43 (s, 3H), 5.42 (s, 2H), 7.33 (s, 1H), 7.72 (d, J=8.7 Hz, 2H), 7.85 (d, J=8.1 Hz, 2H), 8.88 (s, 1H), 11.60 (br s, 1H); APCI-MS (m/z) 459.08 (M+H)⁺.

Example 85

N-{4-[3-Fluoro-4-(trifluoromethyl)phenyl]-1H-imidazol-2-yl}-2-(2,5,7-trimethyl-4,6-dioxo-4,5,6,7-tetrahydro-2H-pyrazolo[3,4-d]pyrimidin-3-yl)acetamide

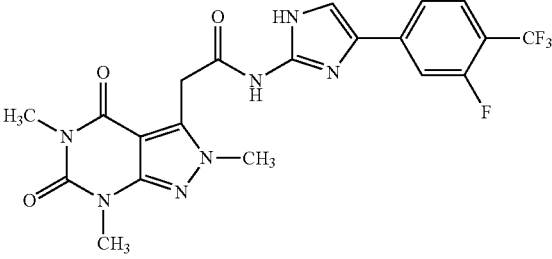 [SMILES: Cn1nc2c(c1CC(=O)Nc1nc(-c3ccc(C(F)(F)F)c(F)c3)c[nH]1)c(=O)n(C)c(=O)n2C]

To a stirred solution of 4-[3-fluoro-4-(trifluoromethyl)phenyl]-1H-imidazol-2-amine (Intermediate 11) (104 mg, 0.428 mmol) in dry toluene (4 ml), sodium hydride (60% dispersion in mineral oil, (12 mg, 1.401 mmol) was added and reaction mixture was stirred for 30 min at room temperature. Step 6 of Intermediate 8 (100 mg, 0.356 mmol) was added to the above reaction mixture and heated to reflux for 48 h. The reaction mixture quenched into water and extracted with ethyl acetate and the combined organic layers were washed with brine, dried over Na₂SO₄. Solvent was evaporated and residue obtained was purified by SiO₂ column chromatography using 2% methanol in chloroform to give 23 mg of the product as off white solid; ¹H NMR (300 MHz, DMSO-d₆): δ 3.18 (s, 3H), 3.36 (s, 3H), 3.85 (s, 3H), 4.30 (s, 2H), 7.62 (s, 1H), 7.70-7.81 (m, 3H), 11.76 (br s, 1H), 11.94 (br s, 1H); APCI-MS (m/z): 480.17 (M+H)$^+$.

Pharmacological Activity

The illustrative examples of the present invention are screened for TRPA1 activity according to a modified procedure described in (a) Tóth, A. et al., *Life Sciences,* 2003, 73, 487-498. (b) McNamara C, R. et al., *Proc. Natl. Acad. Sci. U.S.A.,* 2007, 104, 13525-13530. The screening of the compounds can be carried out by other methods and procedures known to persons skilled in the art.

Screening for TRPA1 Antagonist Using the $^{45}$Calcium Uptake Assay

The inhibition of TRPA1 receptor activation was measured as inhibition of allyl isothiocyanate (AITC) induced cellular uptake of radioactive calcium. Test compounds were dissolved in DMSO to prepare 10 mM stock solution and then diluted using plain medium with 0.1% BSA and 1.8 mM CaCl$_2$ to get desired concentration. Final concentration of DMSO in the reaction was 0.5% (v/v). Human TRPA1 expressing CHO cells were grown in F-12 DMEM medium with 10% FBS, 1% penicillin-streptomycin solution, 400 µg/ml of G-418. Cells were seeded 24 h prior to the assay in 96 well plates so as to get ~50,000 cells per well on the day of experiment. Cells were treated with test compounds for 10 min followed by addition of AITC at a final concentration of 30 µM and 5 µCi/ml $^{45}$Ca$^{+2}$ for 3 min. Cells were washed and lysed using buffer containing 1% Triton X-100, 0.1% deoxycholate and 0.1% SDS. Radioactivity in the lysate was measured in Packard Top count after addition of liquid scintillant. Concentration response curves were plotted as a % of maximal response obtained in the absence of test antagonist. IC$_{50}$ value was calculated from concentration response curve by nonlinear regression analysis using GraphPad PRISM software.

The compounds prepared were tested using the above assay procedure and the results obtained are given in Table 3. Percentage inhibition at concentrations of 1.0 µM and 10.0 µM are given in the table along with IC$_{50}$ (nM) details for selected examples. The IC$_{50}$ (nM) values of the compounds are set forth in Table 3 wherein "A" refers to an IC$_{50}$ value of less than 50 nM, "B" refers to IC$_{50}$ value in range of 50.01 to 100.0 nM and "C" refers to an IC$_{50}$ values above 100.0 nM.

TABLE 3

In-vitro screening results of compounds of invention

| Examples | Percentage inhibition at 1.0 µM | at 10.0 µM | Human IC$_{50}$ value (range) |
|---|---|---|---|
| 1 | 23.05 | 21.39 | — |
| 2 | 35.44 | 79.51 | — |
| 3 | 94.43 | 98.77 | A |
| 4 | 34.39 | 89.77 | — |
| 5 | 55.26 | 82.29 | — |
| 6 | 42.37 | 52.84 | — |
| 7 | 35.52 | 37.28 | — |
| 8 | 91.92 | 100.00 | A |
| 9 | 60.70 | 91.28 | — |
| 10 | 91.00 | 95.30 | B |
| 11 | 96.26 | 98.07 | A |
| 12 | 97.37 | 95.97 | A |
| 13 | 86.45 | 98.82 | B |
| 14 | 92.52 | 92.54 | A |
| 15 | 76.50 | 92.50 | B |
| 16 | 94.96 | 97.14 | A |
| 17 | 33.54 | 49.94 | — |
| 18 | 38.44 | 38.71 | — |
| 19 | 72.12 | 76.86 | — |
| 20 | 22.59 | 67.70 | — |
| 21 | 11.16 | 16.23 | — |
| 22 | 81.41 | 99.41 | A |
| 23 | 87.43 | 92.21 | B |
| 24 | 93.92 | 99.43 | A |
| 25 | 68.31 | 94.76 | — |
| 26 | 95.26 | 98.27 | A |
| 27 | 87.58 | 99.15 | A |
| 28 | 99.51 | 99.68 | A |
| 29 | 95.58 | 97.08 | A |
| 30 | 93.56 | 100.00 | A |
| 31 | 87.44 | 95.35 | B |
| 32 | 92.81 | 96.32 | A |
| 33 | 0.00 | 28.30 | — |
| 34 | 88.81 | 97.01 | C |
| 35 | 64.74 | 96.79 | — |
| 36 | 35.59 | 70.11 | — |
| 37 | 52.90 | 95.44 | — |
| 38 | 57.01 | 97.80 | — |
| 39 | 4.89 | 21.09 | — |
| 40 | 48.49 | 86.22 | — |
| 41 | 37.99 | 86.55 | — |
| 42 | 41.10 | 63.14 | — |
| 43 | 30.13 | 41.58 | — |
| 44 | 27.08 | 77.03 | — |
| 45 | 93.46 | 98.87 | B |
| 46 | 89.26 | 96.58 | C |
| 47 | 98.98 | 99.45 | A |
| 48 | 92.84 | 97.51 | B |
| 49 | 52.26 | 88.46 | — |
| 50 | 0.00 | 19.84 | — |
| 51 | 57.54 | 79.68 | — |
| 52 | 37.75 | 64.81 | — |
| 53 | 97.25 | 98.63 | A |
| 54 | 97.73 | 99.61 | A |
| 55 | 92.23 | 99.15 | B |
| 56 | 96.20 | 98.16 | A |
| 57 | 43.04 | 49.81 | — |
| 58 | 94.63 | 99.25 | A |
| 59 | 97.57 | 99.33 | A |
| 60 | 93.42 | 97.19 | A |
| 61 | 86.05 | 98.33 | B |
| 62 | 90.31 | 95.76 | A |
| 63 | 95.07 | 99.74 | A |
| 64 | 97.78 | 98.29 | A |
| 65 | 12.49 | 24.64 | — |
| 66 | 45.05 | 71.55 | — |
| 67 | 57.60 | 98.43 | — |
| 68 | 91.34 | 99.43 | C |
| 69 | 97.27 | 99.75 | A |
| 70 | 91.47 | 98.76 | A |
| 71 | 78.25 | 99.28 | B |
| 72 | 85.88 | 97.67 | C |
| 73 | 99.06 | 99.91 | A |
| 74 | 92.10 | 98.78 | A |
| 75 | 99.34 | 100 | A |
| 76 | 84.32 | 95.60 | C |
| 77 | 89.48 | 99.58 | B |
| 78 | 100 | 99.65 | A |
| 79 | 100 | 99.99 | A |
| 80 | 99.99 | 100 | A |
| 81 | 93.95 | 99.97 | A |
| 82 | 92.85 | 98.95 | B |
| 83 | 75.59 | 95.02 | A |
| 84 | 17.24 | 83.90 | — |
| 85 | 44.10 | 78.19 | — |

We claim:
1. The compound of the formula:

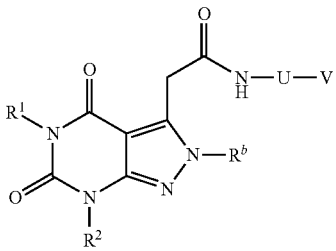

or a pharmaceutically acceptable salt thereof,
wherein,
$R^1$ and $R^2$, which may be same or different, are independently selected from hydrogen and substituted or unsubstituted alkyl;
$R^b$ is selected from hydrogen and substituted or unsubstituted alkyl;
U is substituted or unsubstituted heterocycles selected from the group consisting of thiazole, isoxazole, and imidazole; and
V is substituted or unsubstituted aryl.

2. The compound according to claim 1, wherein $R^1$ and $R^2$ are $(C_1-C_4)$alkyl.

3. The compound according to claim 1, wherein $(C_1-C_4)$ alkyl is methyl.

4. The compound according to claim 1, wherein $R^b$ is hydrogen or methyl.

5. The compound according to claim 1, wherein U is thiazole.

6. The compound according to claim 1, wherein V is phenyl, substituted with one or more substituents selected from halogen, alkyl, haloalkyl and haloalkoxy.

7. The compound according to claim 1, wherein U is thiazole and V is phenyl substituted with one or more substituents selected from fluorine, chlorine, isobutyl, trifluoromethyl, trifluoromethoxy and difluoromethoxy.

8. A compound having the formula:

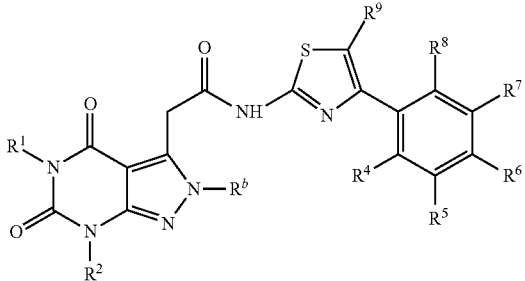

or a pharmaceutically acceptable salt thereof,
wherein,
$R^1$, $R^2$ and $R^b$, which may be the same or different, are each independently hydrogen or $(C_1-C_4)$alkyl;
$R^4$, $R^5$, $R^6$, $R^7$, $R^8$ and $R^9$, which may be same or different, are each independently selected from the group comprising of hydrogen, halogen, substituted or unsubstituted alkyl, haloalkyl, and haloalkoxy.

9. The compound according to claim 8, wherein $R^1$, $R^2$ and $R^b$ are methyl.

10. The compound according to claim 8, wherein $R^9$ is hydrogen.

11. The compound according to claim 8, wherein $R^4$ and $R^8$ are independently selected from hydrogen and fluorine.

12. The compound according to claim 8, wherein $R^5$ and $R^7$ are independently selected from hydrogen, fluorine, trifluoromethyl and trifluoromethoxy.

13. The compound according to claim 8, wherein $R^6$ is selected from hydrogen, fluorine, chlorine, isobutyl, trifluoromethyl, trifluoromethoxy and difluoromethoxy.

14. The compound according to claim 1 selected from:
N-[4-(4-Isobutylphenyl)-1,3-thiazol-2-yl]-2-(2,5,7-trimethyl-4,6-dioxo-4,5,6,7-tetrahydro-2H-pyrazolo[3,4-d]pyrimidin-3-yl)acetamide;
N-[4-(4-Chlorophenyl)-1,3-thiazol-2-yl]-2-(2,5,7-trimethyl-4,6-dioxo-4,5,6,7-tetrahydro-2H-pyrazolo[3,4-d]pyrimidin-3-yl)acetamide;
N-{4-[4-(Trifluoromethyl)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide;
N-{4-[3-(Trifluoromethyl)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide;
N-{4-[3-(Trifluoromethoxy)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide;
N-[4-(2,4-Difluorophenyl)-1,3-thiazol-2-yl]-2-(2,5,7-trimethyl-4,6-dioxo-4,5,6,7-tetrahydro-2H-pyrazolo[3,4-d]pyrimidin-3-yl)acetamide;
N-[4-(3,4-Difluorophenyl)-1,3-thiazol-2-yl]-2-(2,5,7-trimethyl-4,6-dioxo-4,5,6,7-tetrahydro-2H-pyrazolo[3,4-d]pyrimidin-3-yl)acetamide;
N-[4-(3,5-Difluorophenyl)-1,3-thiazol-2-yl]-2-(2,5,7-trimethyl-4,6-dioxo-4,5,6,7-tetrahydro-2H-pyrazolo[3,4-d]pyrimidin-3-yl)acetamide;
N-{4-[4-Fluoro-3-(trifluoromethyl)phenyl]-1,3-thiazol-2-yl}-2-(2,5,7-trimethyl-4,6-dioxo-,5,6,7-tetrahydro-2H-pyrazolo[3,4-d]pyrimidin-3-yl)acetamide;
N-[4-(3-Fluoro-4-trifluoromethylphenyl)-1,3-thiazol-2-yl]-2-(2,5,7-trimethyl-4,6-dioxo-4,5,6,7-tetrahydro-2H-pyrazolo[3,4-d]pyrimidin-3-yl)acetamide;
N-{4-[2-Fluoro-3-(trifluoromethyl)phenyl]-1,3-thiazol-2-yl}-2-(2,5,7-trimethyl-4,6-dioxo-,5,6,7-tetrahydro-2H-pyrazolo[3,4-d]pyrimidin-3-yl)acetamide;
N-{4-[2-Fluoro-4-(trifluoromethyl)phenyl]-1,3-thiazol-2-yl}-2-(2,5,7-trimethyl-4,6-dioxo-,5,6,7-tetrahydro-2H-pyrazolo[3,4-d]pyrimidin-3-yl)acetamide;
N-{4-[2-Fluoro-5-(trifluoromethyl)phenyl]-1,3-thiazol-2-yl}-2-(2,5,7-trimethyl-4,6-dioxo-,5,6,7-tetrahydro-2H-pyrazolo[3,4-d]pyrimidin-3-yl)acetamide;
N-{4-[3-Fluoro-5-(trifluoromethyl)phenyl]-1,3-thiazol-2-yl}-2-(2,5,7-trimethyl-4,6-dioxo-,5,6,7-tetrahydro-2H-pyrazolo[3,4-d]pyrimidin-3-yl)acetamide;
N-{4-[3-Fluoro-4-(trifluoromethoxy)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide;
N-{4-[4-Fluoro-3-(trifluoromethoxy)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide;
N-{4-[4-(Difluoromethoxy)-3-fluorophenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide;
N-{4-[2,3-difluoro-4-(trifluoromethyl)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide;
N-{4-[2,4-Difluoro-3-(trifluoromethyl)phenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide;
N-{4-[4-(Difluoromethoxy)-3,5-difluorophenyl]-1,3-thiazol-2-yl}-2-(2,5,7-trimethyl-4,6-dioxo-4,5,6,7-tetrahydro-2H-pyrazolo[3,4-d]pyrimidin-3-yl)acetamide;

N-[5-(4-Bromophenyl)isoxazol-3-yl]-2-(2,5,7-trimethyl-4,6-dioxo-4,5,6,7-tetrahydro-2H-pyrazolo[3,4-d]pyrimidin-3-yl)acetamide; and N-{4-[3-Fluoro-4-(trifluoromethyl)phenyl]-1H-imidazol-2-yl]-2-(2,5,7-trimethyl-4,6-dioxo-4,5,6,7-tetrahydro-2H-pyrazolo[3,4-d]pyrimidin-3-yl)acetamide;

or a pharmaceutically acceptable salt thereof.

15. A compound having the formula:

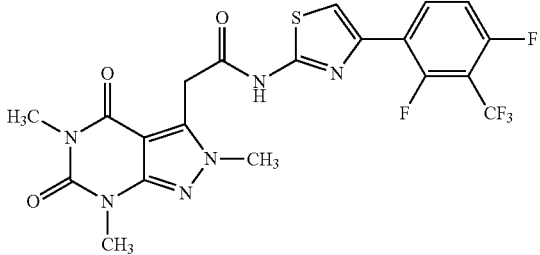 [SMILES: Cn1nc2c(c1CC(=O)Nc1nc(-c3ccc(F)c(C(F)(F)F)c3F)cs1)c(=O)n(C)c(=O)n2C]

or a pharmaceutically acceptable salt thereof.

16. A compound having the formula:

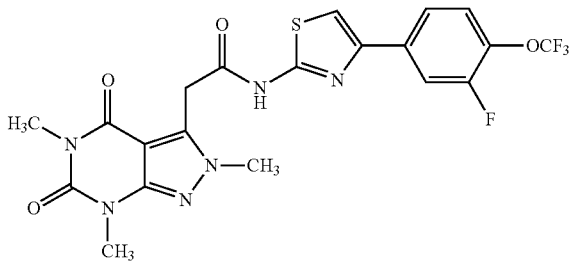 [SMILES: Cn1nc2c(c1CC(=O)Nc1nc(-c3ccc(OC(F)(F)F)c(F)c3)cs1)c(=O)n(C)c(=O)n2C]

or a pharmaceutically acceptable salt thereof.

17. A pharmaceutical composition comprising one or more compound according to claim 1, and one or more pharmaceutically acceptable excipients, carriers, diluents or mixture thereof.

18. A method for treating disease or condition associated with TRPA1 function in a subject in need thereof comprising administering to the subject an effective amount of a compound according to claim 1 wherein the disease or condition is chronic pain, complex regional pain syndrome, neuropathic pain, postoperative pain, rheumatoid arthritic pain, osteoarthritic pain, back pain, visceral pain, cancer pain, or post stroke pain.

19. The method according to claim 18, wherein the disease or condition is chronic pain.

20. The method according to claim 18, wherein the disease or condition is neuropathic pain.

21. The method according to claim 18, wherein the disease or condition is rheumatoid arthritic pain or osteoarthritic pain.

22. A pharmaceutical composition comprising the compound of claim 15, and one or more pharmaceutically acceptable excipients, carriers, diluents or mixture thereof.

23. A method for treating disease or condition associated with TRPA1 function in a subject in need thereof comprising administering to the subject an effective amount of a compound of claim 15 wherein the disease or condition is chronic pain, complex regional pain syndrome, neuropathic pain, postoperative pain, rheumatoid arthritic pain, osteoarthritic pain, back pain, visceral pain, cancer pain, or post stroke pain.

* * * * *